United States Patent
Zhao et al.

(10) Patent No.: US 9,512,121 B2
(45) Date of Patent: Dec. 6, 2016

(54) [1,2,4] TRIAZOL [4,3-A] PYRIDINE DERIVATIVE, PREPARATION METHOD THEREFOR OR MEDICAL APPLICATION THEREOF

(71) Applicant: Jiangsu Hansoh Pharmaceutical Co., Ltd., Lianyungang, Jiangsu (CN)

(72) Inventors: Zhiming Zhao, Jiangsu (CN); Haiyang Wang, Jiangsu (CN); Chenchen Wu, Jiangsu (CN); Qingqing Qi, Jiangsu (CN)

(73) Assignee: Jiangsu Hansoh Pharmaceutical Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 14/889,092

(22) PCT Filed: Mar. 4, 2014

(86) PCT No.: PCT/CN2014/072825
§ 371 (c)(1),
(2) Date: Nov. 4, 2015

(87) PCT Pub. No.: WO2014/180182
PCT Pub. Date: Nov. 13, 2014

(65) Prior Publication Data
US 2016/0122339 A1    May 5, 2016

(30) Foreign Application Priority Data

May 10, 2013   (CN) .......................... 2013 1 0173581

(51) Int. Cl.
*A61K 31/4196* (2006.01)
*C07D 471/04* (2006.01)
*C07D 519/00* (2006.01)

(52) U.S. Cl.
CPC ........... *C07D 471/04* (2013.01); *C07D 519/00* (2013.01)

(58) Field of Classification Search
USPC ................. 514/210.1, 210.21, 233.2, 229.8
See application file for complete search history.

(56) References Cited

U.S. PATENT DOCUMENTS

2006/0287324 A1    12/2006 Sun et al.
2013/0245002 A1*   9/2013 Chen .................... C07D 471/04
                                                514/210.21

FOREIGN PATENT DOCUMENTS

| CN | 101553490 A | 10/2009 | |
| WO | 2007126799 A2 | 11/2007 | |
| WO | 2008051808 A2 | 5/2008 | |
| WO | WO2011/100607 A1 * | 8/2011 | ............ A01N 43/56 |
| WO | 2013038362 A1 | 3/2013 | |

OTHER PUBLICATIONS

Munshi et al., "ARQ 197, a Novel and Selective Inhibitor of the Human c-Met Receptor Tyrosine Kinase with Antitumor Activity," Molecular Cancer Therapeutics, vol. 9, No. 6, pp. 1544-1553 (Jun. 2010).
International Search Report issued Jul. 9, 2014 in International Application No. PCT/CN2014/072825.

* cited by examiner

*Primary Examiner* — Pancham Bakshi
(74) *Attorney, Agent, or Firm* — Panitch Schwarze Belisario & Nadel LLP

(57) ABSTRACT

Provided are [1,2,4]triazol[4,3-a]pyridine derivatives as shown in the general formula (I), a preparation method therefor, and a pharmaceutical composition containing the derivative, wherein the pharmaceutical composition is used as a therapeutic agent, and especially used as a c-Met inhibitor and an immunosuppressant. Each substituent in the general formula (I) is the same as that defined in the specification.

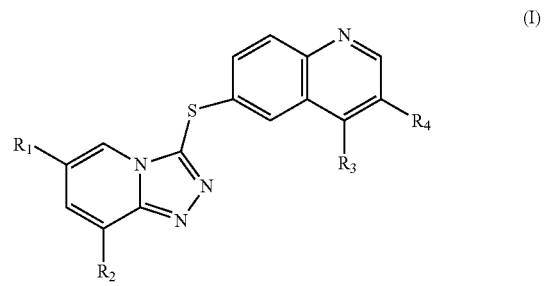

9 Claims, No Drawings

[1,2,4] TRIAZOL [4,3-A] PYRIDINE DERIVATIVE, PREPARATION METHOD THEREFOR OR MEDICAL APPLICATION THEREOF

CROSS-REFERENCE TO RELATED APPLICATION

This application is a Section 371 of International Application No. PCT/CN2014/072825, filed Mar. 4, 2014, which was published in the Chinese language on Nov. 13, 2014 under International Publication No. WO 2014/180182 A1, and the disclosure of which is incorporated herein by reference in its entirety.

FIELD OF THE INVENTION

The present invention relates to novel [1,2,4]triazolo[4,3-a]pyridine derivatives, a preparation method thereof, a pharmaceutical composition containing the derivatives, and their use as a therapeutic agent (especially as a c-Met inhibitor) and in the preparation of immunosuppressant drugs.

BACKGROUND OF THE INVENTION

Hepatocyte growth factor (HGF) receptor, also known as c-Met, is a tyrosine kinase receptor. It is a mature receptor formed by linking α and β subunits which are derived from a single-chain protein precursor by disulfide bonds.

c-Met is a membrane receptor, which is essential to embryonic development and wound healing. Hepatocyte growth factor (HGF) is the only known ligand of c-Met receptor. c-Met is usually expressed in epithelial cells, and the expression of HGF is limited to mesenchymal cells. After excitation by HGF, c-Met can induce some biological responses, these biological responses act synergistically, thereby leading to cell survival and proliferation, cell migration and invasion to other tissues, and blocking apoptosis.

Abnormal activation of c-Met is related to a poor prognosis of cancer. In the face of abnormal activation, c-Met can lead to tumor growth and formation of new blood vessels (angiogenesis, which can provide nutrients to the tumor) which will help the cancer spread to other organs (metastasis). In many types of human malignancies, such as bladder cancer, hepatocellular carcinoma, kidney cancer, stomach cancer, breast cancer, squamous cell carcinoma, and brain cancer, there exists c-Met overexpression or disorder (WO2007/126799).

c-Met abnormality is found in many types of tumors, such as hepatocellular carcinoma (HCC), non-small cell lung cancer (NSCLC), stomach cancer, and colon cancer, etc. c-Met abnormality may manifest as increased expression of c-Met, gene amplification, gene mutation or increased expression of HGF. In these abnormal circumstances, c-Met may be activated in an abnormal state, which contributes to carcinogenesis and poor prognosis. Because of these properties, c-Met is an important target for the treatment of many cancers. In the pharmaceutical industry, drugs that target c-Met can be divided into three categories: c-Met specific drugs, multiple target (including c-Met) selective drugs, and antibody drugs.

Inhibition of c-Met signal pathway is an important therapeutic strategy for cancer. Many small molecule compounds were found to effectively block the HGF/c-Met signal transduction pathway, but so far there is no small molecule inhibitor of c-Met tyrosine kinase on the market.

There is no c-Met specific drug approved by FDA. The compounds in clinical trials intended as C-Met specific drugs include SGX-523, JNJ38877605 (Johnson & Johnson), AMG-208, and INCB28060 (Novartis/InCyte). SNG-523 and JNJ38877605 were discontinued in clinical trials due to renal toxicity. AMG-208 and INCB28060 are currently in clinical phase-I trial.

BRIEF SUMMARY OF THE INVENTION

It's an aim of the present invention to provide a compound of formula (I) or a pharmaceutically acceptable salt thereof, or a metabolite, metabolic precursor or prodrug thereof. The present invention provides a compound of formula (I), having the following structure:

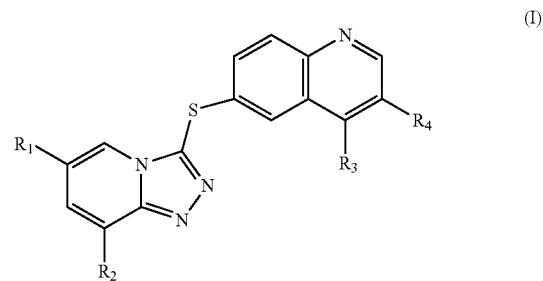

wherein:
$R_1$ is selected from the group consisting of pyrazolyl, alkyl, cycloalkyl, haloalkyl, alkoxyl, aryl, heteroaryl and heterocyclyl, optionally substituted by one or more groups selected from the group consisting of halogen, hydroxy, alkyl, alkoxyl, cycloalkyl, heterocyclyl, aryl, heteroaryl, $-(CH_2)_nC(O)OR_5$, $-C(O)NR_6R_7$, $-NHC(O)R_5$, $-NR_6R_7$, $-NHC(O)NR_6R_7$, $-NHC(O)(O)R_5$ and $-NHS(O)_mR_5$; preferably pyrazolyl;

$R_2$ is selected from the group consisting of hydrogen, halogen, $C_1$-$C_6$ alkoxyl and halo$C_1$-$C_6$ alkoxyl; preferably hydrogen and halogen; and more preferably halogen;

$R_3$ is selected from the group consisting of halogen, $C_1$-$C_6$ alkyl, $C_1$-$C_6$ alkoxyl, halo$C_1$-$C_6$ alkoxyl, 3 to 8-membered heterocyclyl, $-NHR_8$ and $NR_8R_9$, optionally substituted by one or more groups selected from the group consisting of halogen, hydroxy, alkyl, alkoxyl, cycloalkyl, heterocyclyl, aryl, heteroaryl, $-(CH_2)_nC(O)OR_5$, $-C(O)NR_6R_7$, $-NHC(O)R_5$, $-NR_6R_7$, $-NHC(O)NR_6R_7$, $-NHC(O)(O)R_5$ and $-NHS(O)_mR_5$; preferably alkoxyl and halogen; and more preferably halogen;

$R_4$ is selected from the group consisting of hydrogen, pyrazolyl, $C_1$-$C_6$ alkyl, $C_3$-$C_{10}$ cycloalkyl, $C_1$-$C_6$ alkoxyl, aryl, heteroaryl, 3 to 8-membered heterocyclyl, $-NHR_8$ and $NR_8R_9$, optionally substituted by one or more groups selected from the group consisting of halogen, hydroxy, alkyl, alkoxyl, cycloalkyl, heterocyclyl, aryl, heteroaryl, $-(CH_2)_nC(O)OR_5$, $-C(O)NR_6R_7$, $-NHC(O)R_5$, $-NR_6R_7$, $-NHC(O)NR_6R_7$, $-NHC(O)(O)R_5$ and $-NHS(O)_mR_5$;

or $R_3$ and $R_4$ are taken together with the attached carbon atoms to form a $C_5$-$C_{10}$ aliphatic ring, heterocyclyl comprising 1 to 3 heteroatoms selected from the group consisting of O, N and S, lactone, lactam, thiolactam, urea and thiourea, optionally substituted by one or more groups selected from the group consisting of halogen, hydroxy, alkyl, alkoxyl, alkoxylalkyl, cycloalkyl, heterocyclyl, aryl, heteroaryl, —C(O)R$_5$, —C(O)NR$_6$R$_7$, —NHC(O)R$_5$, —NR$_6$R$_7$, —OC(O)NR$_6$R$_7$, —NHC(O)NR$_6$R$_7$, —NHC(O)(O)R$_5$ and —NHS(O)$_m$R$_5$; more preferably, R$_3$ and R$_4$ are taken together with the attached carbon atoms to form a C$_5$-C$_8$ lactam;

R$_5$ is selected from the group consisting of hydrogen, C$_1$-C$_6$ alkyl, C$_3$-C$_{10}$ cycloalkyl, 3 to 8-membered heterocyclyl, C$_2$-C$_6$ alkenyl, C$_2$-C$_6$ alkynyl, aryl and heteroaryl, wherein the alkyl, cycloalkyl, heterocyclyl, aryl and heteroaryl are each optionally substituted by one or more groups independently selected from the group consisting of alkyl, halogen, hydroxy, amino, alkoxyl, cycloalkyl, heterocyclyl, aryl, heteroaryl, —(CH$_2$)$_n$C(O)OR$_8$, —C(O)NR$_9$R$_{10}$, —NHC(O)R$_8$, —NR$_9$R$_{10}$, —NHC(O)NR$_9$R$_{10}$, —NHC(O)OR$_8$ and —NHS(O)$_m$R$_8$;

R$_6$ and R$_7$ are each independently selected from the group consisting of hydrogen, C$_1$-C$_6$ alkyl, C$_3$-C$_{10}$ cycloalkyl, 3 to 8-membered heterocyclyl, aryl and heteroaryl, wherein the alkyl, cycloalkyl, heterocyclyl, aryl and heteroaryl are each optionally substituted by one or more groups independently selected from the group consisting of alkyl, halogen, hydroxy, amino, alkoxyl, cycloalkyl, heterocyclyl, hydroxyalkyl, alkynyl, aryl, heteroaryl, and —OR$_8$;

R$_8$ is selected from the group consisting of hydrogen, C$_1$-C$_6$ alkyl, C$_3$-C$_{10}$ cycloalkyl, C$_1$-C$_6$ alkoxyl, 3 to 8-membered heterocyclyl, hydroxyalkyl, aryl and heteroaryl;

R$_9$ and R$_{10}$ are each independently selected from the group consisting of hydrogen, C$_1$-C$_6$ alkyl, C$_3$-C$_{10}$ cycloalkyl, 3 to 8-membered heterocyclyl, aryl and heteroaryl; and m and n are each independently selected from 0, 1 and 2.

In one preferred embodiment of the present invention, the compound of formula (I) or the pharmaceutically acceptable salt thereof is a compound of formula (II) or a pharmaceutically acceptable salt thereof:

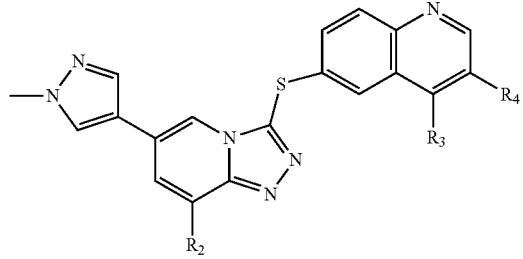

(II)

wherein R$_2$, R$_3$ and R$_4$ are as defined in formula (I).

In another preferred embodiment of the present invention, the compound of formula (I) or the pharmaceutically acceptable salt thereof is a compound of formula (IIIA) or (IIIB) or a pharmaceutically acceptable salt thereof:

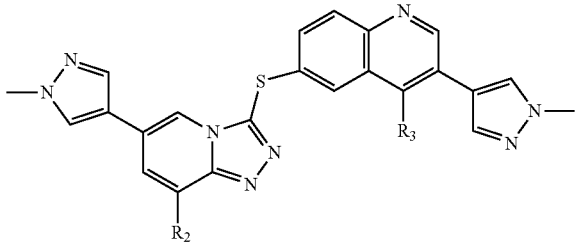

(IIIA)

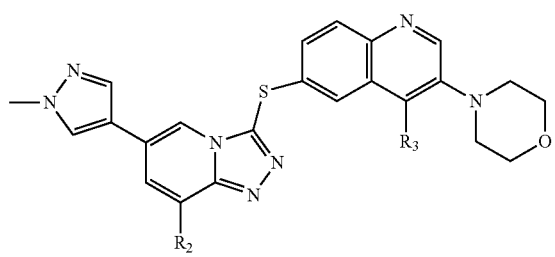

(IIIB)

wherein R$_2$ and R$_3$ are as defined in formula (I).

Preferably, in the compound of formula (IIIA) or (IIIB) or the pharmaceutically acceptable salt thereof, R$_2$ is selected from the group consisting of hydrogen, halogen, C$_1$-C$_6$ alkoxyl and haloC$_1$-C$_6$ alkoxyl, preferably hydrogen and halogen.

Preferably, in the compound of formula (IIIA) or (IIIB) or the pharmaceutically acceptable salt thereof, R$_3$ is selected from the group consisting of hydrogen, halogen, C$_1$-C$_6$ alkyl, C$_1$-C$_6$ alkoxyl, haloC$_1$-C$_6$ alkoxyl, —NHR$_8$ and NR$_8$R$_9$, preferably halogen and C$_1$-C$_6$ alkoxyl; and R$_8$ and R$_9$ are as defined in formula (I).

In another preferred embodiment of the present invention, the compound of formula (I) or the pharmaceutically acceptable salt thereof is a compound of formula (IV) or a pharmaceutically acceptable salt thereof:

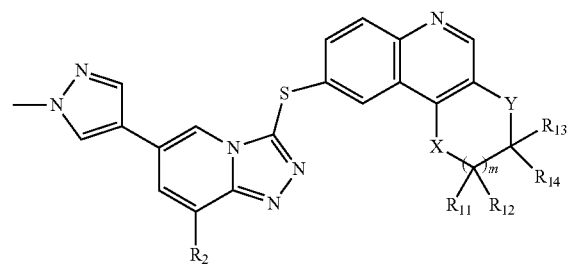

(IV)

wherein R$_2$ is as defined in formula (I);
X=O, N or S, preferably O;
Y=O, N or S, preferably O;
m=0, 1 or 2;
R$_{11}$, R$_{12}$, R$_{13}$ and R$_{14}$ are each independently selected from the group consisting of hydrogen, C$_1$-C$_6$ alkyl, C$_3$-C$_{10}$ cycloalkyl, 3 to 8-membered heterocyclyl, C$_2$-C$_6$ alkenyl, C$_2$-C$_6$ alkynyl, aryl and heteroaryl; wherein R$_{11}$ or R$_{12}$ and R$_{13}$ or R$_{14}$ are taken together with the attached carbon atoms to form a 5 to 10-membered ring or heterocyclyl, or, R$_{11}$, R$_{12}$ or R$_{13}$, R$_{14}$ are taken together with the attached carbon atoms to form a 5 to 10-membered ring or heterocyclyl;

wherein the alkyl, cycloalkyl, heterocyclyl, aryl or heteroaryl are each optionally substituted by one or more groups independently selected from the group consisting of alkyl, halogen, hydroxy, amino, alkoxyl, cycloalkyl, heterocyclyl, aryl, and heteroaryl.

Preferably, in the compound of formula (IV) or the pharmaceutically acceptable salt thereof, $R_2$ is selected from the group consisting of hydrogen, halogen, $C_1$-$C_6$ alkoxyl and halo$C_1$-$C_6$ alkoxyl, preferably hydrogen and halogen.

In another preferred embodiment of the present invention, the compound of formula (I) or the pharmaceutically acceptable salt thereof is a compound of formula (V) or a pharmaceutically acceptable salt thereof:

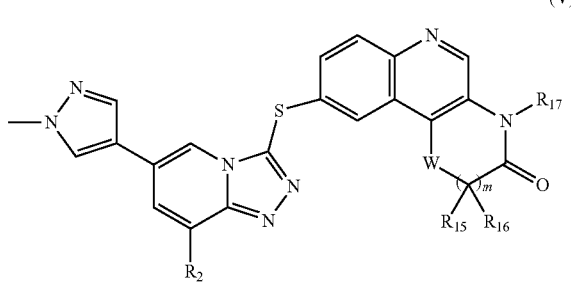

(V)

wherein $R_2$ is as defined in formula (I);

W is selected from the group consisting of $CH_2$, O, N and S, preferably O and N, and more preferably O;

$R_{15}$ and $R_{16}$ are independently selected from the group consisting of hydrogen, halogen, $C_1$-$C_6$ alkyl and alkoxyl;

$R_{17}$ is selected from the group consisting of hydrogen, $C_1$-$C_6$ alkyl, $C_1$-$C_6$ alkoxyl, $C_1$-$C_6$ alkoxylalkyl, C(O)$R_5$, $C_3$-$C_{10}$ cycloalkyl and 3 to 8-membered heterocyclyl;

m=0 or 1.

Preferably, in the compound of formula (V) or the pharmaceutically acceptable salt thereof, $R_2$ is selected from the group consisting of hydrogen, halogen, $C_1$-$C_6$ alkoxyl and halo$C_1$-$C_6$ alkoxyl, preferably hydrogen and halogen.

Preferably, in the compound of formula (V) or the pharmaceutically acceptable salt thereof, $R_{17}$ is selected from the group consisting of hydrogen, $C_1$-$C_6$ alkyl, $C_1$-$C_6$ alkoxyl, $C_1$-$C_6$ alkoxylalkyl, C(O)$R_5$, $C_3$-$C_{10}$ cycloalkyl and 3 to 8-membered heterocyclyl; preferably $C_1$-$C_6$ alkyl and $C_3$-$C_{10}$ cycloalkyl.

A pharmaceutically acceptable salt described in the present invention is formed by a compound of the present invention and an acid selected from the group consisting of: hydrochloric acid, p-toluenesulfonic acid, tartaric acid, maleic acid, lactic acid, methanesulfonic acid, sulfuric acid, phosphoric acid, citric acid, acetic acid and trifluoroacetic acid; preferably hydrochloric acid, p-toluenesulfonic acid, tartaric acid and trifluoroacetic acid.

In particular, the present invention includes, but is not limited to, the following exemplary compounds:

| Example No. | Structure and Name |
|---|---|
| 2 | 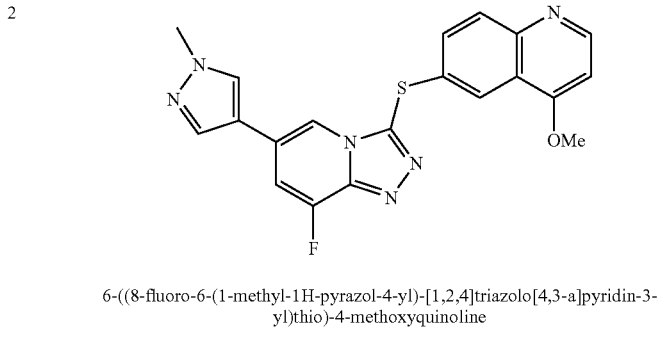<br>6-((8-fluoro-6-(1-methyl-1H-pyrazol-4-yl)-[1,2,4]triazolo[4,3-a]pyridin-3-yl)thio)-4-methoxyquinoline |
| 3 | 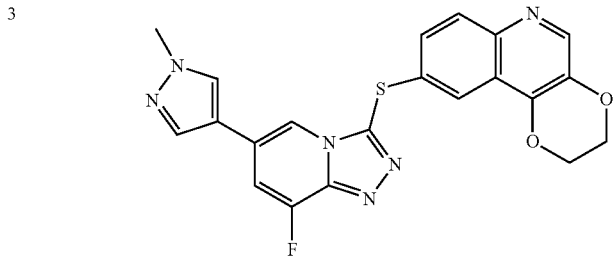<br>9-((8-fluoro-6-(1-methyl-1H-pyrazol-4-yl)-[1,2,4]triazolo[4,3-a]pyridin-3-yl)thio)-2,3-dihydro-[1,4]dioxino[2,3-c]quinoline |

| Example No. | Structure and Name |
|---|---|
| 4 | 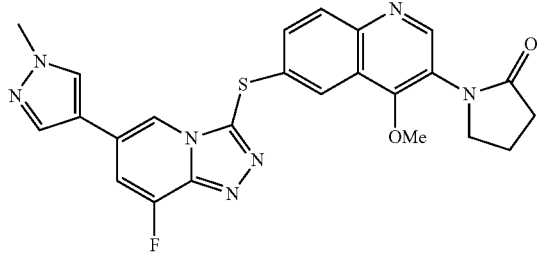 [SMILES: COc1c(N2CCCC2=O)cnc2ccc(Sc3nnc4c(F)cc(-c5cnn(C)c5)cn34)cc12]<br>1-(6-((8-fluoro-6-(1-methyl-1H-pyrazol-4-yl)-[1,2,4]triazolo[4,3-a]pyridin-3-yl)thio)-4-methoxyquinolin-3-yl)pyrrolidin-2-one |
| 5 | 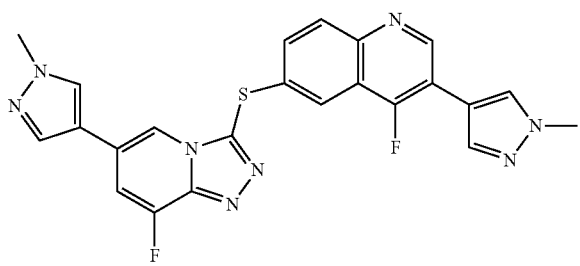 [SMILES: Cn1cc(-c2cc(F)c3nnc(Sc4ccc5ncc(-c6cnn(C)c6)c(F)c5c4)n3c2)cn1]<br>4-fluoro-6-((8-fluoro-6-(1-methyl-1H-pyrazol-4-yl)-[1,2,4]triazolo[4,3-a]pyridin-3-yl)thio)-3-(1-methyl-1H-pyrazol-4-yl)quinoline |
| 6 | 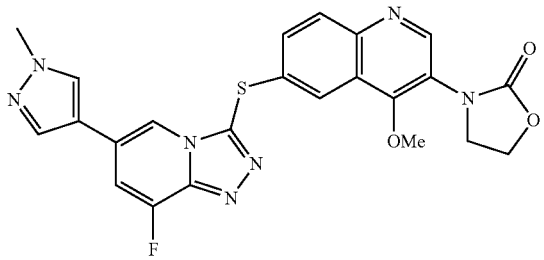 [SMILES: COc1c(N2CCOC2=O)cnc2ccc(Sc3nnc4c(F)cc(-c5cnn(C)c5)cn34)cc12]<br>3-(6-((8-fluoro-6-(1-methyl-1H-pyrazol-4-yl)-[1,2,4]triazolo[4,3-a]pyridin-3-yl)thio)-4-methoxyquinolin-3-yl)oxazolidin-2-one |
| 7 | 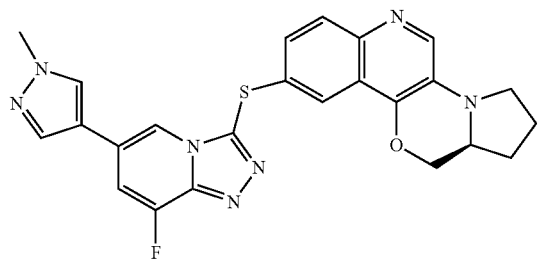 [SMILES: Cn1cc(-c2cc(F)c3nnc(Sc4ccc5ncc6c(c5c4)OC[C@@H]4CCCN64)n3c2)cn1]<br>(S)-9-((8-fluoro-6-(1-methyl-1H-pyrazol-4-yl)-[1,2,4]triazolo[4,3-a]pyridin-3-yl)thio)-2,3,12,12a-tetrahydro-1H-pyrrolo[1',2':4,5][1,4]oxazino[3,2-c]quinoline |

| Example No. | Structure and Name |
|---|---|
| 8 | 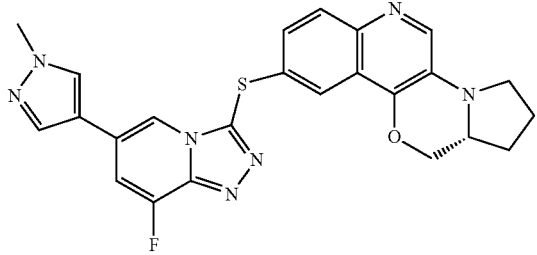 [SMILES: Cn1cc(-c2cc(F)c3nnc(Sc4ccc5ncc6c(c5c4)OC[C@H]4CCCN64)n3c2)cn1]<br>(R)-9-((8-fluoro-6-(1-methyl-1H-pyrazol-4-yl)-[1,2,4]triazolo[4,3-a]pyridin-3-yl)thio)-2,3,12,12a-tetrahydro-1H-pyrrolo[1',2':4,5][1,4]oxazino[3,2-c]quinoline |
| 9 | 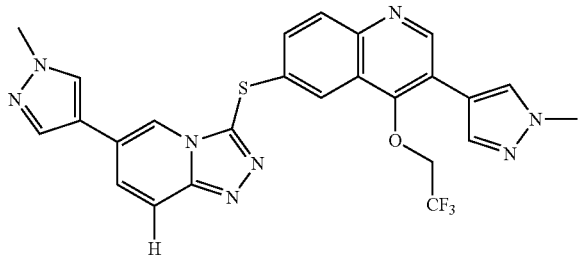 [SMILES: Cn1cc(-c2ccc3nnc(Sc4ccc5ncc(-c6cnn(C)c6)c(OCC(F)(F)F)c5c4)n3c2)cn1]<br>3-(1-methyl-1H-pyrazol-4-yl)-6-((6-(1-methyl-1H-pyrazol-4-yl)-[1,2,4]triazolo[4,3-a]pyridin-3-yl)thio)-4-(2,2,2-trifluoroethoxy)quinoline |
| 10 | 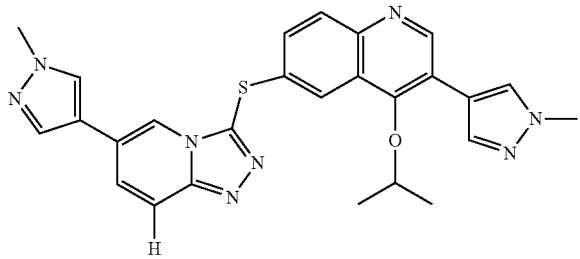 [SMILES: CC(C)Oc1c(-c2cnn(C)c2)cnc2ccc(Sc3nnc4ccc(-c5cnn(C)c5)cn34)cc12]<br>4-isopropoxy-3-(1-methyl-1H-pyrazol-4-yl)-6-((6-(1-methyl-1H-pyrazol-4-yl)-[1,2,4]triazolo[4,3-a]pyridin-3-yl)thio)quinoline |
| 11 | 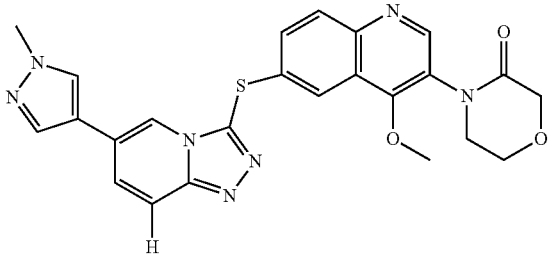 [SMILES: COc1c(N2CCOCC2=O)cnc2ccc(Sc3nnc4ccc(-c5cnn(C)c5)cn34)cc12]<br>4-(4-methoxy-6-((6-(1-methyl-1H-pyrazol-4-yl)-[1,2,4]triazolo[4,3-a]pyridin-3-yl)thio)quinolin-3-yl)morpholin-3-one |

-continued

| Example No. | Structure and Name |
|---|---|
| 12 | 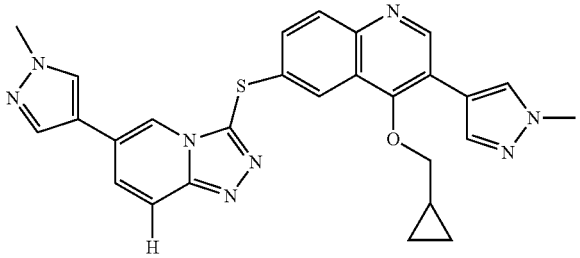 [SMILES: Cn1cc(-c2ccc3nnc(Sc4ccc5ncc(-c6cnn(C)c6)c(OCC6CC6)c5c4)n3c2)cn1]
4-(cyclopropylmethoxy)-3-(1-methyl-1H-pyrazol-4-yl)-6-((6-(1-methyl-1H-pyrazol-4-yl)-[1,2,4]triazolo[4,3-a]pyridin-3-yl)thio)quinoline |
| 13 | 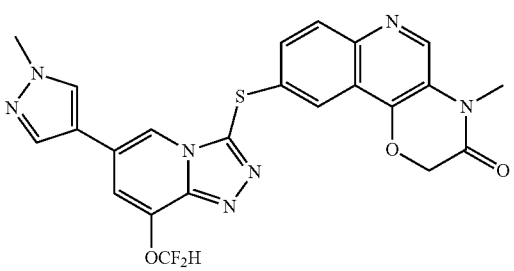
9-((8-(difluoromethoxy)-6-(1-methyl-1H-pyrazol-4-yl)-[1,2,4]triazolo[4,3-a]pyridin-3-yl)thio)-4-methyl-2H-[1,4]oxazino[3,2-c]quinolin-3(4H)-one |
| 14 | 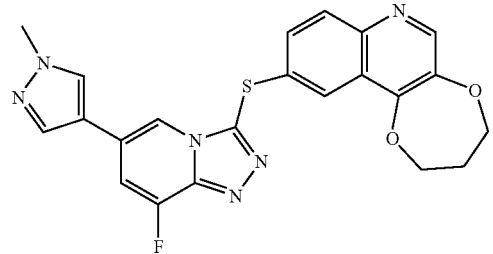 [SMILES: Cn1cc(-c2cc(F)c3nnc(Sc4ccc5ncc6c(c5c4)OCCCO6)n3c2)cn1]
10-((8-fluoro-6-(1-methyl-1H-pyrazol-4-yl)-[1,2,4]triazolo[4,3-a]pyridin-3-yl)thio)-3,4-dihydro-2H-[1,4]dioxepino[2,3-c]quinoline |
| 15 | 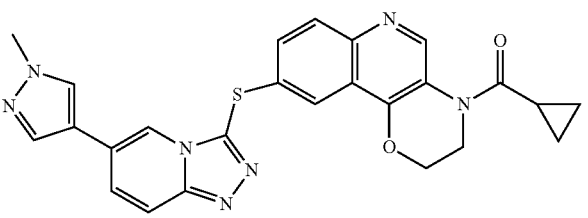 [SMILES: Cn1cc(-c2ccc3nnc(Sc4ccc5ncc6c(c5c4)OCCN6C(=O)C4CC4)n3c2)cn1]
cyclopropyl(9-((6-(1-methyl-1H-pyrazol-4-yl)-[1,2,4]triazolo[4,3-a]pyridin-3-yl)thio)-2,3-dihydro-4H-[1,4]oxazino[3,2-c]quinolin-4-yl)methanone |
| 16 | 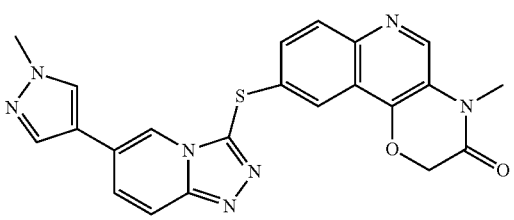 [SMILES: CN1C(=O)COc2c1cnc1ccc(Sc3nnc4ccc(-c5cnn(C)c5)cn34)cc21]
4-methyl-9-((6-(1-methyl-1H-pyrazol-4-yl)-[1,2,4]triazolo[4,3-a]pyridin-3-yl)thio)-2H-[1,4]oxazino[3,2-c]quinolin-3(4H)-one |

| Example No. | Structure and Name |
|---|---|
| 17 | 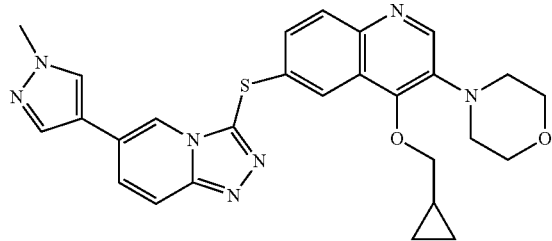 [SMILES: Cn1cc(-c2ccc3nnc(Sc4ccc5ncc(N6CCOCC6)c(OCC6CC6)c5c4)n3c2)cn1]<br>4-(4-(cyclopropylmethoxy)-6-((6-(1-methyl-1H-pyrazol-4-yl)-[1,2,4]triazolo[4,3-a]pyridin-3-yl)thio)quinolin-3-yl)morpholine |
| 18 | 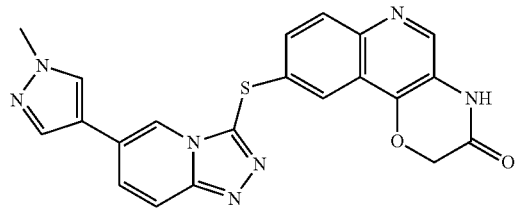 [SMILES: Cn1cc(-c2ccc3nnc(Sc4ccc5ncc6c(c5c4)OCC(=O)N6)n3c2)cn1]<br>9-((6-(1-methyl-1H-pyrazol-4-yl)-[1,2,4]triazolo[4,3-a]pyridin-3-yl)thio)-2H-[1,4]oxazino[3,2-c]quinolin-3(4H)-one |
| 19 | 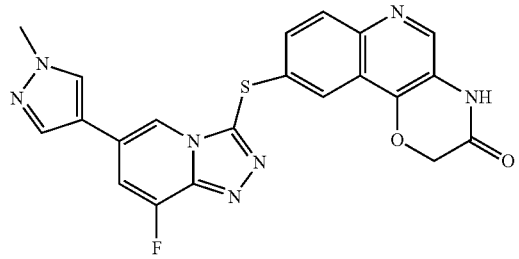 [SMILES: Cn1cc(-c2cc(F)c3nnc(Sc4ccc5ncc6c(c5c4)OCC(=O)N6)n3c2)cn1]<br>9-((8-fluoro-6-(1-methyl-1H-pyrazol-4-yl)-[1,2,4]triazolo[4,3-a]pyridin-3-yl)thio)-2H-[1,4]oxazino[3,2-c]quinolin-3(4H)-one |
| 20 | 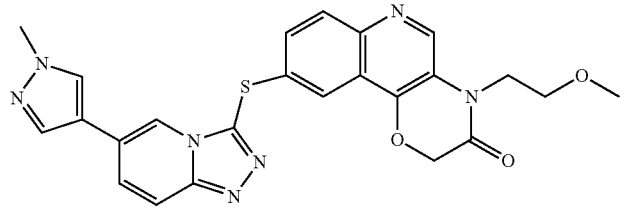 [SMILES: COCCN1C(=O)COc2c1cnc1ccc(Sc3nnc4ccc(-c5cnn(C)c5)cn34)cc21]<br>4-(2-methoxyethyl)-9-((6-(1-methyl-1H-pyrazol-4-yl)-[1,2,4]triazolo[4,3-a]pyridin-3-yl)thio)-2H-[1,4]oxazino[3,2-c]quinolin-3(4H)-one |
| 21 | 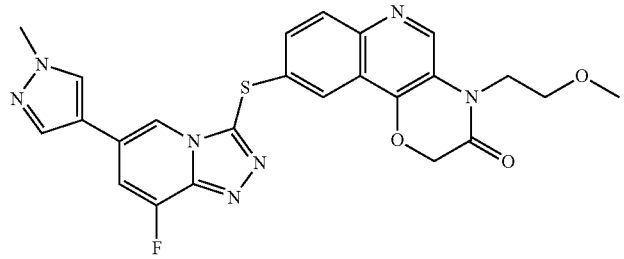 [SMILES: COCCN1C(=O)COc2c1cnc1ccc(Sc3nnc4c(F)cc(-c5cnn(C)c5)cn34)cc21]<br>9-((8-fluoro-6-(1-methyl-1H-pyrazol-4-yl)-[1,2,4]triazolo[4,3-a]pyridin-3-yl)thio)-4-(2-methoxyethyl)-2H-[1,4]oxazino[3,2-c]quinolin-3(4H)-one |

| Example No. | Structure and Name |
|---|---|
| 22 | 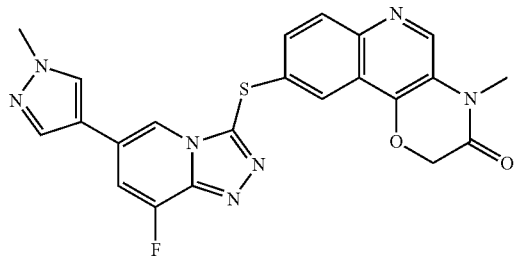 [SMILES: CN1C(=O)COc2c1cnc1ccc(Sc3nnc4c(F)cc(-c5cnn(C)c5)cn34)cc21]
9-((8-fluoro-6-(1-methyl-1H-pyrazol-4-yl)-[1,2,4]triazolo[4,3-a]pyridin-3-yl)thio)-4-methyl-2H-[1,4]oxazino[3,2-c]quinolin-3(4H)-one |
| 23 | 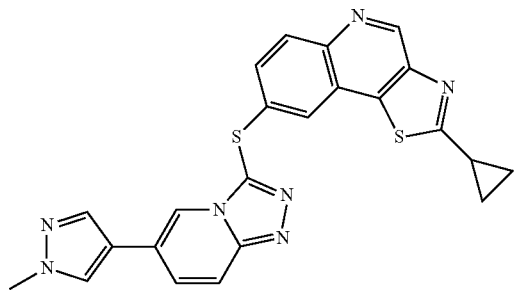 [SMILES: Cn1cc(-c2ccc3nnc(Sc4ccc5ncc6nc(C7CC7)sc6c5c4)n3c2)cn1]
2-cyclopropyl-8-((6-(1-methyl-1H-pyrazol-4-yl)-[1,2,4]triazolo[4,3-a]pyridin-3-yl)thio)thiazolo[4,5-c]quinoline |
| 24 | 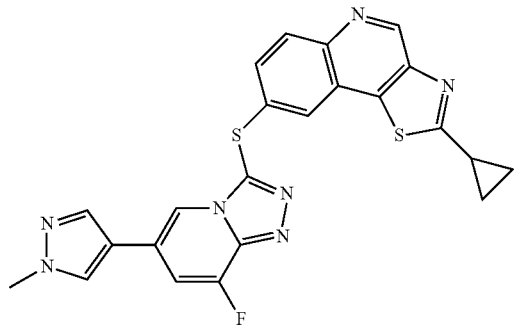 [SMILES: Cn1cc(-c2cc(F)c3nnc(Sc4ccc5ncc6nc(C7CC7)sc6c5c4)n3c2)cn1]
2-cyclopropyl-8-((8-fluoro-6-(1-methyl-1H-pyrazol-4-yl)-[1,2,4]triazolo[4,3-a]pyridin-3-yl)thio)thiazolo[4,5-c]quinoline |
| 25 | 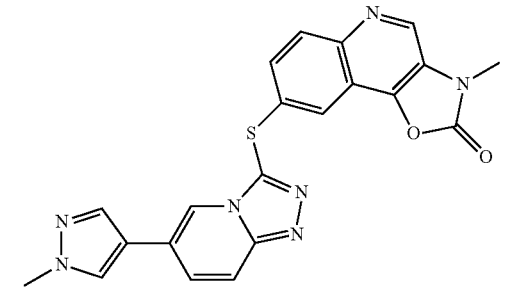
3-methyl-8-((6-(1-methyl-1H-pyrazol-4-yl)-[1,2,4]triazolo[4,3-a]pyridin-3-yl)thio)oxazolo[4,5-c]quinolin-2(3H)-one |

-continued

| Example No. | Structure and Name |
|---|---|
| 26 | 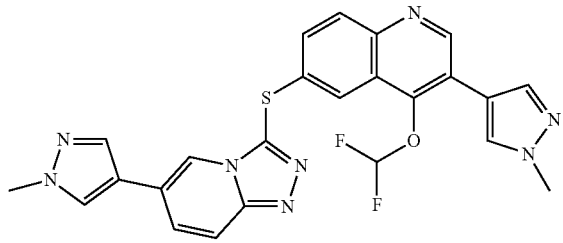 [SMILES: Cn1cc(-c2ccc3nnc(Sc4ccc5ncc(-c6cnn(C)c6)c(OC(F)F)c5c4)n3c2)cn1]

4-(difluoromethoxy)-3-(1-methyl-1H-pyrazol-4-yl)-6-((6-(1-methyl-1H-pyrazol-4-yl)-[1,2,4]triazolo[4,3-a]pyridin-3-yl)thio)quinoline |
| 27 | 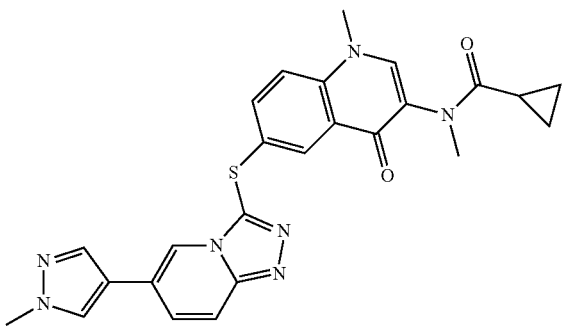 [SMILES: CN(C(=O)C1CC1)c1cn(C)c2ccc(Sc3nnc4ccc(-c5cnn(C)c5)cn34)cc2c1=O]

N-methyl-N-(1-methyl-6-((6-(1-methyl-1H-pyrazol-4-yl)-[1,2,4]triazolo[4,3-a]pyridin-3-yl)thio)-4-oxo-1,4-dihydroquinolin-3-yl)cyclopropanecarboxamide |
| 28 | 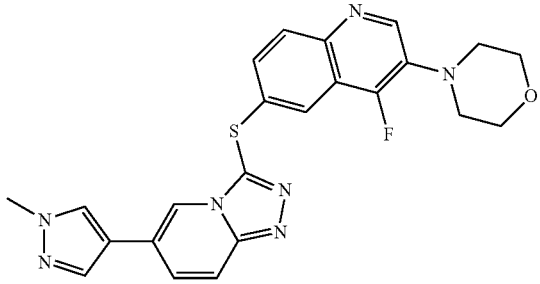 [SMILES: Cn1cc(-c2ccc3nnc(Sc4ccc5ncc(N6CCOCC6)c(F)c5c4)n3c2)cn1]

4-(4-fluoro-6-((6-(1-methyl-1H-pyrazol-4-yl)-[1,2,4]triazolo[4,3-a]pyridin-3-yl)thio)quinolin-3-yl)morpholine |
| 29 | 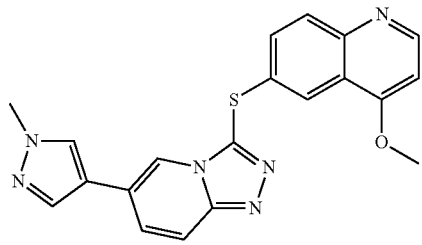

4-methoxy-6-((6-(1-methyl-1H-pyrazol-4-yl)-[1,2,4]triazolo[4,3-a]pyridin-3-yl)thio)quinoline |

| Example No. | Structure and Name |
|---|---|
| 30 | 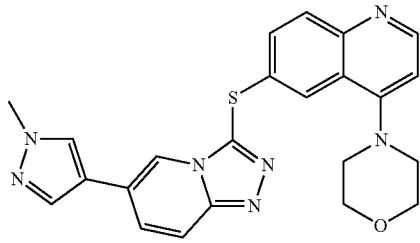 [SMILES: Cn1cc(-c2ccc3nnc(Sc4ccc5nccc(N6CCOCC6)c5c4)n3c2)cn1]<br>4-(6-((6-(1-methyl-1H-pyrazol-4-yl)-[1,2,4]triazolo[4,3-a]pyridin-3-yl)thio)quinolin-4-yl)morpholine |
| 31 | 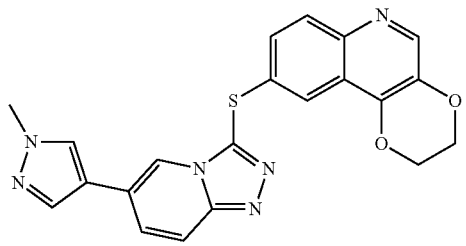 [SMILES: Cn1cc(-c2ccc3nnc(Sc4ccc5ncc6c(c5c4)OCCO6)n3c2)cn1]<br>9-((6-(1-methyl-1H-pyrazol-4-yl)-[1,2,4]triazolo[4,3-a]pyridin-3-yl)thio)-2,3-dihydro-[1,4]dioxino[2,3-c]quinoline |
| 32 | 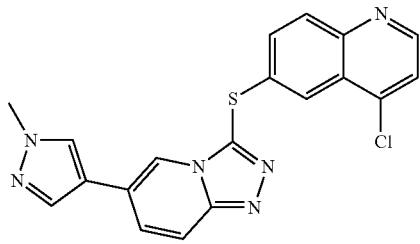 [SMILES: Cn1cc(-c2ccc3nnc(Sc4ccc5nccc(Cl)c5c4)n3c2)cn1]<br>4-chloro-6-((6-(1-methyl-1H-pyrazol-4-yl)-[1,2,4]triazolo[4,3-a]pyridin-3-yl)thio)quinoline |
| 33 | 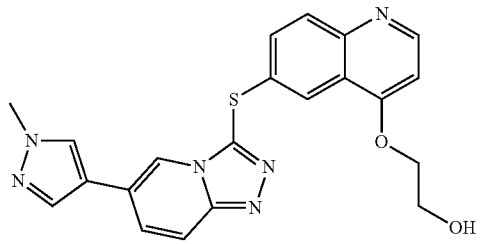 [SMILES: Cn1cc(-c2ccc3nnc(Sc4ccc5nccc(OCCO)c5c4)n3c2)cn1]<br>2-((6-((6-(1-methyl-1H-pyrazol-4-yl)-[1,2,4]triazolo[4,3-a]pyridin-3-yl)thio)quinolin-4-yl)oxy)ethan-1-ol |
| 34 | 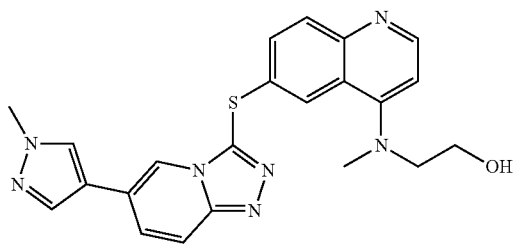 [SMILES: CN(CCO)c1ccnc2ccc(Sc3nnc4ccc(-c5cnn(C)c5)cn34)cc12]<br>2-(methyl(6-((6-(1-methyl-1H-pyrazol-4-yl)-[1,2,4]triazolo[4,3-a]pyridin-3-yl)thio)quinolin-4-yl)amino)ethan-1-ol |

| Example No. | Structure and Name |
|---|---|
| 35 | 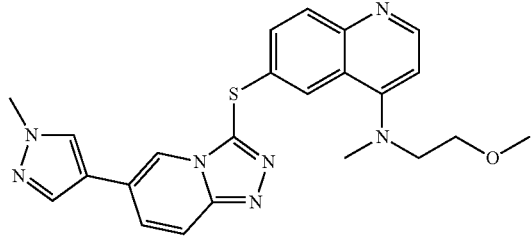<br>N-(2-methoxyethyl)-N-methyl-6-((6-(1-methyl-1H-pyrazol-4-yl)-[1,2,4]triazolo[4,3-a]pyridin-3-yl)thio)quinolin-4-amine |
| 36 | 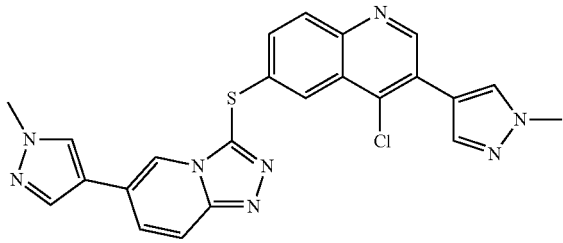<br>4-chloro-3-(1-methyl-1H-pyrazol-4-yl)-6-((6-(1-methyl-1H-pyrazol-4-yl)-[1,2,4]triazolo[4,3-a]pyridin-3-yl)thio)quinoline |
| 37 | 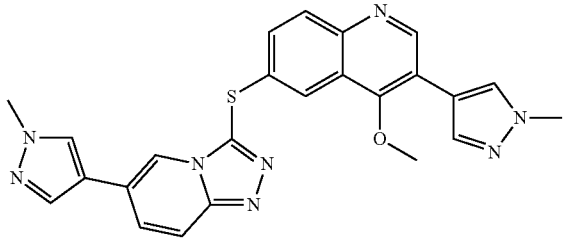<br>4-methoxy-3-(1-methyl-1H-pyrazol-4-yl)-6-((6-(1-methyl-1H-pyrazol-4-yl)-[1,2,4]triazolo[4,3-a]pyridin-3-yl)thio)quinoline |
| 38 | 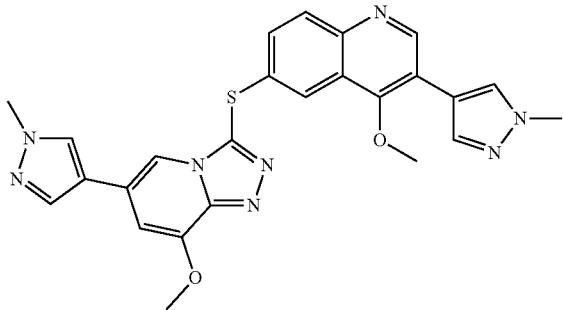<br>4-methoxy-6-((8-methoxy-6-(1-methyl-1H-pyrazol-4-yl)-[1,2,4]triazolo[4,3-a]pyridin-3-yl)thio)-3-(1-methyl-1H-pyrazol-4-yl)quinoline |

| Example No. | Structure and Name |
|---|---|
| 39 | 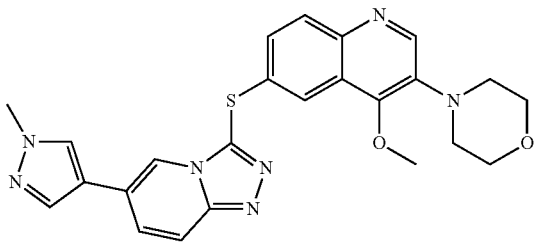 [SMILES: COc1c(N2CCOCC2)cnc2ccc(Sc3nnc4ccc(-c5cnn(C)c5)cn34)cc12]<br>4-(4-methoxy-6-((6-(1-methyl-1H-pyrazol-4-yl)-[1,2,4]triazolo[4,3-a]pyridin-3-yl)thio)quinolin-3-yl)morpholine |
| 40 | 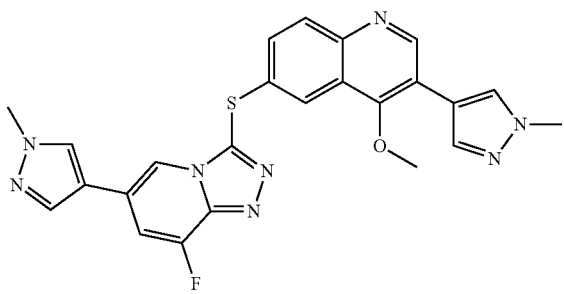<br>6-((8-fluoro-6-(1-methyl-1H-pyrazol-4-yl)-[1,2,4]triazolo[4,3-a]pyridin-3-yl)thio)-4-methoxy-3-(1-methyl-1H-pyrazol-4-yl)quinoline |
| 41 | 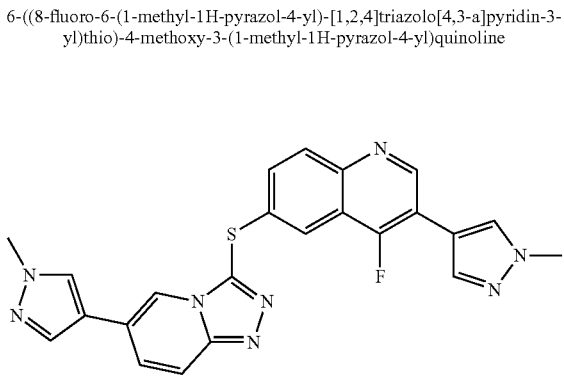<br>4-fluoro-3-(1-methyl-1H-pyrazol-4-yl)-6-((6-(1-methyl-1H-pyrazol-4-yl)-[1,2,4]triazolo[4,3-a]pyridin-3-yl)thio)quinoline |
| 42 | 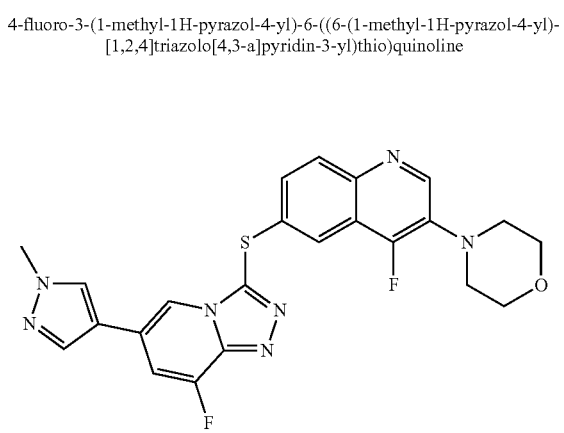<br>4-(4-fluoro-6-((8-fluoro-6-(1-methyl-1H-pyrazol-4-yl)-[1,2,4]triazolo[4,3-a]pyridin-3-yl)thio)quinolin-3-yl)morpholine |

| Example No. | Structure and Name |
|---|---|
| 43 | 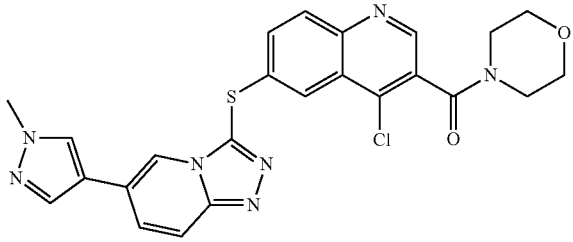 [SMILES: Cn1cc(-c2ccc3nnc(Sc4ccc5ncc(C(=O)N6CCOCC6)c(Cl)c5c4)n3c2)cn1]<br>(4-chloro-6-((6-(1-methyl-1H-pyrazol-4-yl)-[1,2,4]triazolo[4,3-a]pyridin-3-yl)thio)quinolin-3-yl)(morpholino)methanone |
| 44 | 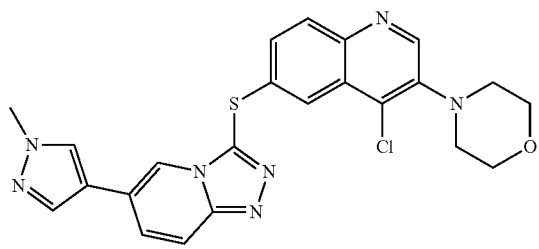 [SMILES: Cn1cc(-c2ccc3nnc(Sc4ccc5ncc(N6CCOCC6)c(Cl)c5c4)n3c2)cn1]<br>4-(4-chloro-6-((6-(1-methyl-1H-pyrazol-4-yl)-[1,2,4]triazolo[4,3-a]pyridin-3-yl)thio)quinolin-3-yl)morpholine |
| 45 | 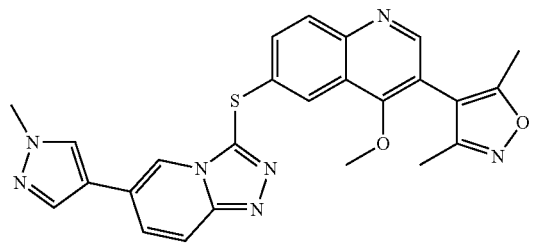 [SMILES: COc1c(-c2c(C)noc2C)cnc2ccc(Sc3nnc4ccc(-c5cnn(C)c5)cn34)cc12]<br>4-(4-methoxy-6-((6-(1-methyl-1H-pyrazol-4-yl)-[1,2,4]triazolo[4,3-a]pyridin-3-yl)thio)quinolin-3-yl)-3,5-dimethylisoxazole |
| 46 | 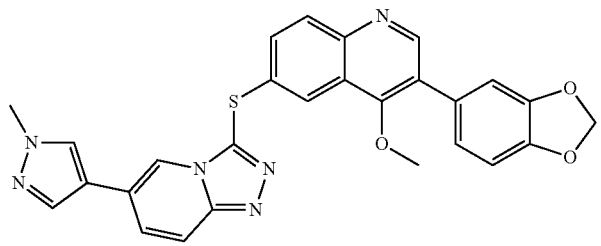 [SMILES: COc1c(-c2ccc3c(c2)OCO3)cnc2ccc(Sc3nnc4ccc(-c5cnn(C)c5)cn34)cc12]<br>3-(benzo[d][1,3]dioxol-5-yl)-4-methoxy-6-((6-(1-methyl-1H-pyrazol-4-yl)-[1,2,4]triazolo[4,3-a]pyridin-3-yl)thio)quinoline |
| 47 | 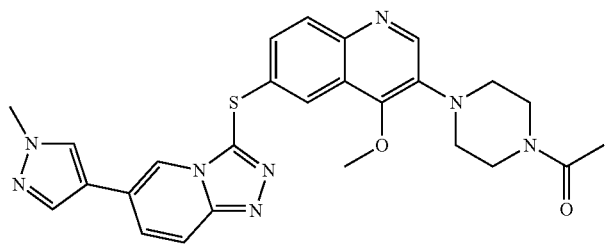 [SMILES: COc1c(N2CCN(C(C)=O)CC2)cnc2ccc(Sc3nnc4ccc(-c5cnn(C)c5)cn34)cc12]<br>1-(4-(4-methoxy-6-((6-(1-methyl-1H-pyrazol-4-yl)-[1,2,4]triazolo[4,3-a]pyridin-3-yl)thio)quinolin-3-yl)piperazin-1-yl)ethan-1-one |

| Example No. | Structure and Name |
|---|---|
| 48 | 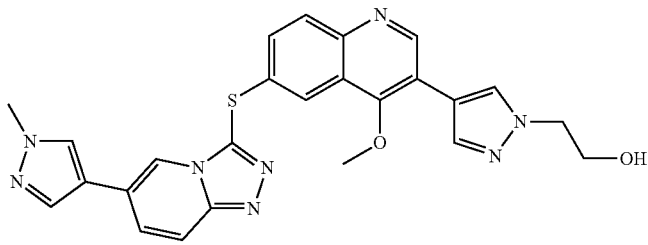 [SMILES: COc1c(-c2cnn(CCO)c2)cnc2ccc(Sc3nnc4ccc(-c5cnn(C)c5)cn34)cc12]<br>2-(4-(4-methoxy-6-((6-(1-methyl-1H-pyrazol-4-yl)-[1,2,4]triazolo[4,3-a]pyridin-3-yl)thio)quinolin-3-yl)-1H-pyrazol-1-yl)ethan-1-ol | or a pharmaceutically acceptable salt thereof.

Furthermore, the present invention relates to a process for preparing the compound of formula (I) or the pharmaceutically acceptable salt thereof, comprising a step of:

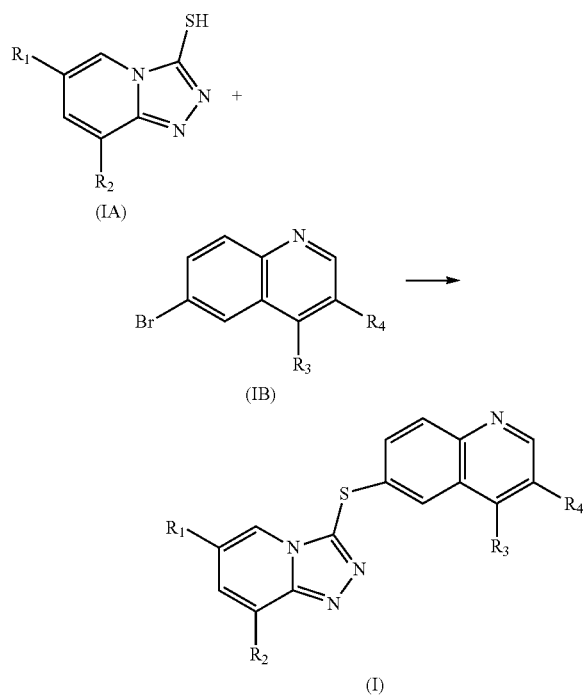

reacting a compound of formula (IA) with a compound of formula (IB) under an alkaline condition by a S-arylation coupling reaction to give the compound of formula (I); wherein $R_1$, $R_2$, $R_3$ and $R_4$ are as defined in formula (I).

The solvent used in this reaction is selected from the group consisting of 1,4-dioxane, acetonitrile, N,N-dimethylformamide, dimethyl sulfoxide, and N-methylpyrrolidone, preferably 1,4-dioxane, N,N-dimethylformamide or dimethyl sulfoxide.

The reaction is carried out in the presence of a base, which is selected from the group consisting of an inorganic base (such as sodium carbonate, potassium carbonate, sodium hydrogen carbonate, potassium phosphate, sodium tert-butoxide, potassium tert-butoxide) or an organic base (such as triethylamine, pyridine, piperidine, t-butylamine, diethylisopropylamine), preferably sodium tert-butoxide, potassium tert-butoxide or diethylisopropylamine.

One aspect of the invention provides a pharmaceutical composition comprising a therapeutically effective amount of a compound of formula (I) or a pharmaceutically acceptable salt thereof, and a pharmaceutically acceptable carrier or excipient. The invention also provides use of the pharmaceutical composition in the preparation of a medicament for the treatment of a protein kinase-related disease, wherein the protein kinase is selected from the group consisting of c-Met and VEGFR receptor tyrosine kinase. The invention also provides use of the pharmaceutical composition in the preparation of a medicament for the treatment of cancer, preferably in the preparation of a medicament for the treatment of lung cancer, breast cancer, squamous cell carcinoma or stomach cancer.

Another aspect of the invention provides a method of modulating protein kinase catalytic activity, comprising a step of contacting the protein kinase with a compound of formula (I) or a pharmaceutically acceptable salt thereof or a pharmaceutical composition comprising the same, wherein the protein kinase is selected from the group consisting of c-Met and VEGFR receptor tyrosine kinase.

Another aspect of the invention provides use of a compound of formula (I) or a pharmaceutically acceptable salt thereof or a pharmaceutical composition comprising the same in the preparation of a medicament as a protein kinase inhibitor, wherein the protein kinase is selected from the group consisting of c-Met and VEGFR receptor tyrosine kinase.

Another aspect of the invention provides use of a compound of formula (I) or a pharmaceutically acceptable salt thereof in the preparation of a medicament for the treatment of a protein kinase-related disease, wherein the protein kinase is selected from the group consisting of c-Met and VEGFR receptor tyrosine kinase.

Another aspect of the invention provides a compound of formula (I) or a pharmaceutically acceptable salt thereof or a pharmaceutical composition comprising the same, for use as a medicament in the treatment of a protein kinase-related disease, wherein the protein kinase is selected from the group consisting of c-Met and VEGFR receptor tyrosine kinase.

Another aspect of the invention provides a compound of formula (I) or a pharmaceutically acceptable salt thereof or a pharmaceutical composition comprising the same, for use as a medicament in the treatment of cancer, preferably as a medicament in the treatment of lung cancer, breast cancer, squamous cell carcinoma or stomach cancer.

Another aspect of the invention provides use of a compound of formula (I) or a pharmaceutically acceptable salt thereof in the preparation of a medicament for the treatment of cancer, preferably for the treatment of lung cancer, breast cancer, squamous cell carcinoma or stomach cancer.

The compounds of the invention may be used in the treatment of neoplasia, including cancer and metastasis including, but not limited to: cancer, such as bladder cancer, breast cancer, colon cancer, kidney cancer, hepatocellular carcinoma, lung cancer (NSCLC), and skin cancer; hematopoietic tumors of the lymphatic system (such as leukemia, acute lymphocytic leukemia, etc.); hematopoietic tumors of the marrow system (such as acute and chronic myelogenous leukemia, myelodysplastic syndrome and promyelocytic leukemia); tumors caused by mesenchyme (such as fibrosarcoma and rhabdomyosarcoma or other sarcomas such as soft tissue sarcoma and osteosarcoma); tumors of the central and peripheral nervous systems (such as astrocytoma, neuroblastoma, glioma tumor and nerve endings tumor); or other tumors (including malignant melanoma, seminoma, teratocarcinoma, thyroid follicular cancer and Kaposi's sarcoma etc.).

Preferably, the compounds of the present invention are used for the treatment of lung cancer, breast cancer, squamous cell carcinoma or stomach cancer.

A "pharmaceutical composition" as used herein means a mixture comprising one or more of the compounds described in the present invention or physiologically/pharmaceutically acceptable salts or prodrugs thereof and other chemical components, and other ingredients such as physiologically/pharmaceutically acceptable carriers and excipients. The purpose of a pharmaceutical composition is to facilitate administration of a compound to an organism, which will help absorption of the active ingredient, and then to exert biological activity.

It is known to those skilled in the art that the dosage of a drug depends on a variety of factors including, but not limited to, the following factors: the activity of the specific compound, the age of the patient, the weight of the patient, the general health of the patient, the behavior of the patient, diet of the patient, time of drug administration, route of drug administration, rate of excretion, drug combination etc. In addition, the best treatment route, such as mode of therapy, a daily dose of the compound of formula (I) or the type of pharmaceutically acceptable salt thereof can be verified by conventional treatment programs.

Unless otherwise stated, the terms used in the specification and claims have the following meanings.

"Alkyl" refers to a saturated aliphatic hydrocarbon group including $C_1$-$C_{20}$ straight-chain and branched-chain groups. Preferably, an alkyl is an alkyl having 1 to 10 carbon atoms, such as methyl, ethyl, propyl, 2-propyl, n-butyl, isobutyl, tert-butyl or pentyl, etc. More preferably, an alkyl is a lower alkyl having 1 to 4 carbon atoms, such as methyl, ethyl, propyl, 2-propyl, n-butyl, isobutyl or tert-butyl, etc. The alkyl may be substituted or unsubstituted. When substituted, the substituent is preferably one or more groups independently selected from the group consisting of alkoxyl, halogen, hydroxy, nitro, cyano, cycloalkyl, heterocyclyl, aryl, heteroaryl, —C(O)OR$_9$, —OC(O)R$_9$, —O(CH$_2$)$_n$C(O)OR$_9$, —OC(O)NR$_{10}$R$_{11}$, carbonyl, —S(O)$_n$R$_9$, —OSO$_2$R$_9$, —SO$_2$NR$_{10}$R$_{11}$, —NHC(O)R$_9$ and —NR$_{10}$R$_{11}$.

"Cycloalkyl" refers to a 3 to 8 membered all-carbon monocyclic ring group, wherein the 3 to 8 membered all-carbon monocyclic ring can comprise one or more double bonds, but the ring does not have a completely conjugated π-electron system. Examples of cycloalkyl include cyclopropyl, cyclobutyl, cyclopentyl, cyclopentenyl, cyclohexyl, cyclohexadienyl, cycloheptyl, cycloheptatrienyl, etc. The cycloalkyl can be substituted or unsubstituted. When substituted, the substituent is preferably one or more groups independently selected from the group consisting of alkyl, alkoxyl, halogen, hydroxy, nitro, cyano, cycloalkyl, heterocyclyl, aryl, heteroaryl, —C(O)OR$_9$, —OC(O)R$_9$, —O(CH$_2$)$_n$C(O)OR$_9$, —OC(O)NR$_{10}$R$_{11}$, carbonyl, —S(O)$_n$R$_9$, —OSO$_2$R$_9$, —SO$_2$NR$_{10}$R$_{11}$, —NHC(O)R$_9$ and —NR$_{10}$R$_{11}$.

"Alkenyl" refers to an alkyl group as defined above having at least two carbon atoms and at least one carbon-carbon double bond. Examples of alkenyl include vinyl, 1-propenyl, 2-propenyl, 1-, 2- or 3-butenyl etc. The alkenyl can be substituted or unsubstituted. When substituted, the substituent is preferably one or more groups independently selected from the group consisting of alkyl, alkoxyl, halogen, hydroxy, nitro, cyano, cycloalkyl, heterocyclyl, aryl, heteroaryl, —C(O)OR$_9$, —OC(O)R$_9$, —O(CH$_2$)$_n$C(O)OR$_9$, —OC(O)NR$_{10}$R$_{11}$, carbonyl, —S(O)$_n$R$_9$, —OSO$_2$R$_9$, —SO$_2$NR$_{10}$R$_{11}$, —NHC(O)R$_9$, and —NR$_{10}$R$_{11}$.

"Alkynyl" refers to an alkyl group as defined above having at least two carbon atoms and at least one carbon-carbon triple bond. Examples of alkynyl include ethynyl, 1-propynyl, 2-propynyl, 1-, 2- or 3-butynyl etc. The alkynyl can be substituted or unsubstituted. When substituted, the substituent is preferably one or more groups independently selected from the group consisting of alkyl, alkoxyl, halogen, hydroxy, nitro, cyano, cycloalkyl, heterocyclyl, aryl, heteroaryl, —C(O)OR$_9$, —OC(O)R$_9$, —O(CH$_2$)$_n$C(O)OR$_9$, —OC(O)NR$_{10}$R$_{11}$, carbonyl, —S(O)$_n$R$_9$, —OSO$_2$R$_9$, —SO$_2$NR$_{10}$R$_{11}$, —NHC(O)R$_9$, and —NR$_{10}$R$_{11}$.

"Heterocyclyl" refers to a 3 to 8 membered monocyclic ring group, in which one or more ring atoms are heteroatoms selected from the group consisting of nitrogen, oxygen or S(O)$_n$ (wherein n is an integer from 0 to 2), and the remaining ring atoms are carbon. The ring can also have one or more double bonds, but the ring does not have a completely conjugated π-electron system. Examples of heterocyclyl are pyrrolidinyl, piperidinyl, piperazinyl, morpholinyl, thiomorpholinyl, homopiperazinyl, etc. The heterocyclyl can be substituted or unsubstituted. When substituted, the substituent is preferably one or more groups independently selected from the group consisting of alkyl, alkoxyl, halogen, hydroxy, nitro, cyano, cycloalkyl, heterocyclyl, aryl, heteroaryl, —C(O)OR$_9$, —OC(O)R$_9$, —O(CH$_2$)$_n$C(O)OR$_9$, —OC(O)NR$_{10}$R$_{11}$, carbonyl, —S(O)$_n$R$_9$, —OSO$_2$R$_9$, —SO$_2$NR$_{10}$R$_{11}$, —NHC(O)R$_9$ and —NR$_{10}$R$_{11}$.

"Bicyclic cycloalkyl" refers to a 5 to 14 membered all-carbon fused ring group (a "fused" ring system means that each ring in the system shares a pair of adjacent carbon atoms with another ring in the system), wherein one or more rings can contain one or more double bonds, but none of the rings has a completely conjugated π-electron system. For example, bicyclic cycloalkyl includes

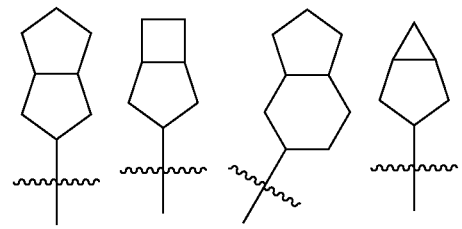

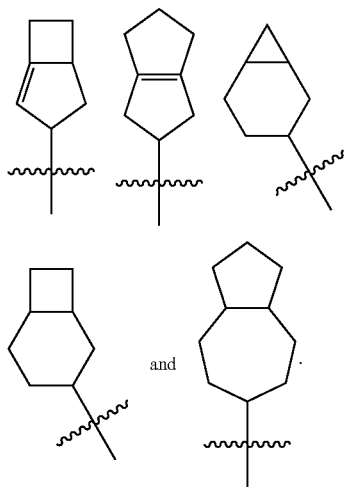

Preferably, a bicyclic cycloalkyl is 5/5 or 5/6 membered, and more preferably is 5/5 membered. The bicyclic cycloalkyl can be substituted or unsubstituted. When substituted, the substituent is preferably one or more groups independently selected from the group consisting of alkyl, alkoxyl, halogen, hydroxy, nitro, cyano, cycloalkyl, heterocyclyl, aryl, heteroaryl, —C(O)OR$_9$, —OC(O)R$_9$, —O(CH$_2$)$_n$C(O)OR$_9$, —OC(O)NR$_{10}$R$_{11}$, carbonyl, —S(O)$_n$R$_9$, —OSO$_2$R$_9$, —SO$_2$NR$_{10}$R$_{11}$, —NHC(O)R$_9$ and —NR$_{10}$R$_{11}$.

"Bicyclic heterocyclyl" refers to a 5 to 14 membered fused ring group (a "fused" ring system means that each ring in the system shares a pair of adjacent carbon atoms with another ring in the system), wherein one or more ring atoms are heteroatoms selected from the group consisting of nitrogen, oxygen, and S(O)$_n$ (where n is an integer from 0 to 2), and the remaining ring atoms are carbon. These rings can contain one or more double bonds, but the ring does not have a completely conjugated π-electron system. Preferably, a bicyclic heterocyclyl is 7 to 10 membered. For example, bicyclic heterocyclyl includes

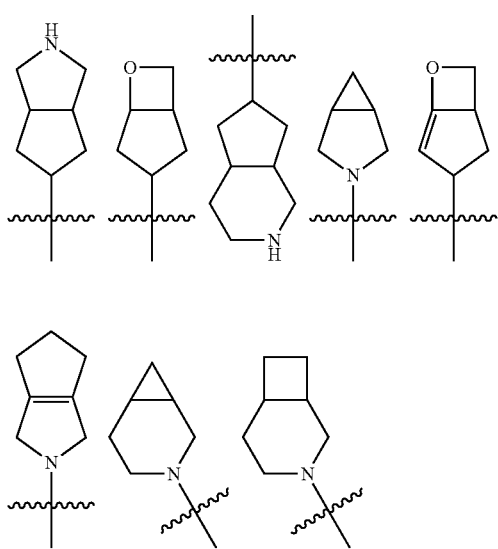

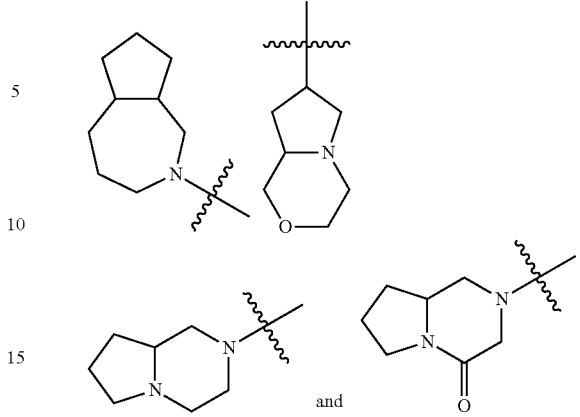

Further preferably, a bicyclic heterocyclyl is 5/5 or 5/6 membered, and more preferably is 5/5 membered. The bicyclic heterocyclyl can be substituted or unsubstituted. When substituted, the substituent is preferably one or more groups independently selected from the group consisting of alkyl, alkoxyl, halogen, hydroxy, nitro, cyano, cycloalkyl, heterocyclyl, aryl, heteroaryl, —C(O)OR$_9$, —OC(O)R$_9$, —O(CH$_2$)$_n$C(O)OR$_9$, —OC(O)NR$_{10}$R$_{11}$, carbonyl, —S(O)$_n$R$_9$, —OSO$_2$R$_9$, —SO$_2$NR$_{10}$R$_{11}$, —NHC(O)R$_9$ and —NR$_{10}$R$_{11}$.

"Bridged cycloalkyl" refers to a 5 to 14 membered all-carbon polycyclic group, wherein every two rings in the system share two disconnected carbon atoms. The rings can contain one or more double bonds, but the ring does not have a completely conjugated π-electron system. Preferably, a bridged cycloalkyl is 7 to 10 membered. For example, bridged cycloalkyl includes

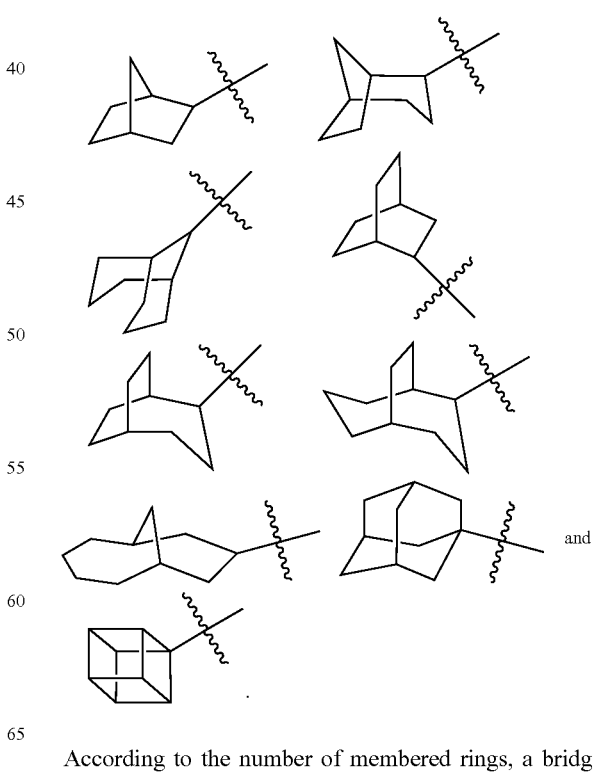

According to the number of membered rings, a bridged cycloalkyl is divided into bicyclic, tricyclic, tetracyclic or polycyclic bridged cycloalkyl, preferably bicyclic, tricyclic or tetracyclic bridged cycloalkyl, and more preferably bicyclic or tricyclic bridged cycloalkyl. The bridged cycloalkyl group can be substituted or unsubstituted. When substituted, the substituent is preferably one or more groups independently selected from the group consisting of alkyl, alkoxyl, halogen, hydroxy, nitro, cyano, cycloalkyl, heterocyclyl, aryl, heteroaryl, —C(O)OR$_9$, —OC(O)R$_9$, —O(CH$_2$)$_n$C(O)OR$_9$, —OC(O)NR$_{10}$R$_{11}$, carbonyl, —S(O)$_n$R$_9$, —OSO$_2$R$_9$, —SO$_2$NR$_{10}$R$_{11}$, —NHC(O)R$_9$, and —NR$_{10}$R$_{11}$.

"Bridged heterocyclyl" refers to a 5 to 14 membered polycyclic group, wherein every two rings in the system share two disconnected carbon atoms, wherein one or more ring atoms are heteroatoms selected from the group of nitrogen, oxygen, and S(O)$_n$ (where n is an integer from 0 to 2), and the remaining ring atoms are carbon. The rings can contain one or more double bonds, but the ring does not have a completely conjugated π electronic system. Preferably, a bridged heterocyclyl is 7 to 10 membered. For example, bridged heterocyclyl includes

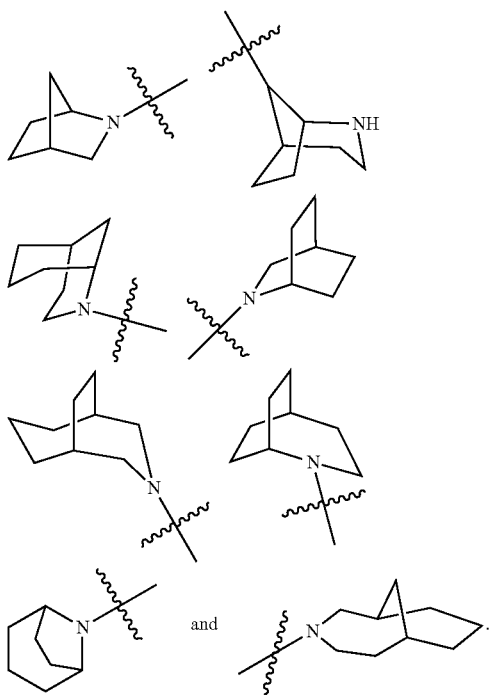

According to the number of membered rings, a bridged heterocyclyl is divided into bicyclic, tricyclic, tetracyclic or polycyclic bridged heterocyclyl, preferably bicyclic, tricyclic or tetracyclic bridged heterocyclyl, and more preferably bicyclic or tricyclic bridged heterocyclyl. The bridged heterocyclyl can be substituted or unsubstituted. When substituted, the substituent is preferably one or more groups independently selected from the group consisting of alkyl, alkoxyl, halogen, hydroxy, nitro, cyano, cycloalkyl, heterocyclyl, aryl, heteroaryl, —C(O)OR$_9$, —OC(O)R$_9$, —O(CH$_2$)$_n$C(O)OR$_9$, —OC(O)NR$_{10}$R$_{11}$, carbonyl, —S(O)$_n$R$_9$, —OSO$_2$R$_9$, —SO$_2$NR$_{10}$R$_{11}$, —NHC(O)R$_9$, and —NR$_{10}$R$_{11}$.

"Spiro cycloalkyl" refers to a 5 to 14 membered polycyclic group with rings connected through one common carbon atom (called a spiro atom), wherein these rings can contain one or more double bonds, but the ring does not have a completely conjugated π-electron system. Preferably, a spiro cycloalkyl is 7 to 10 membered. For example, spiro cycloalkyl includes

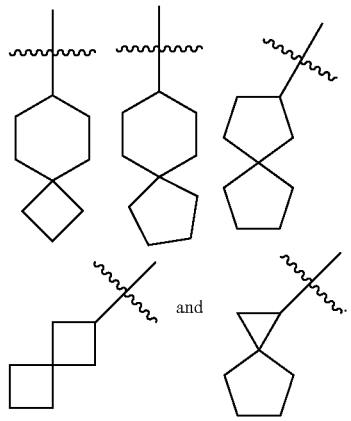

According to the number of common spiro atoms, a spiro cycloalkyl is divided into mono-spiro cycloalkyl, di-spiro cycloalkyl or poly-spiro cycloalkyl, preferably mono-spiro cycloalkyl and di-spiro cycloalkyl, and more preferably 4/4 membered, 4/5 membered, 4/6 membered, 5/5 or 5/6 membered mono-spiro cycloalkyl. The spiro cycloalkyl can be substituted or unsubstituted. When substituted, the substituent is preferably one or more groups independently selected from the group consisting of alkyl, alkoxyl, halogen, hydroxy, nitro, cyano, cycloalkyl, heterocyclyl, aryl, heteroaryl, —C(O)OR$_9$, —OC(O)R$_9$, —O(CH$_2$)$_m$C(O)OR$_9$, —OC(O)NR$_{10}$R$_{11}$, carbonyl, —S(O)$_n$R$_9$, —OSO$_2$R$_9$, —SO$_2$NR$_{10}$R$_{11}$, —NHC(O)R$_9$, and —NR$_{10}$R$_{11}$.

"Spiro heterocyclyl" refers to a 5 to 14 membered polycyclic hydrocarbon group with rings connected through one common carbon atom (called a spiro atom), wherein one or more ring atoms are heteroatoms selected from the group consisting of nitrogen, oxygen, and S(O)$_n$ (where n is an integer from 0 to 2), and the remaining ring atoms are carbon. These rings can contain one or more double bonds, but the ring does not have a completely conjugated π-electron system. Preferably, a spiro heterocyclyl is 7 to 10 membered. For example, spiro heterocyclyl includes

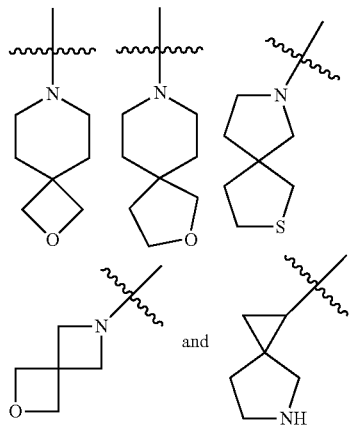

According to the number of common Spiro atoms, a spiro heterocyclyl is divided into monospirocheteroyclic, bispiroheterocyclic or polyspiroheterocyclic, preferably monospiro heterocyclyl and di-spiro heterocyclyl, and more preferably 4/4 membered, 4/5 membered, 4/6 membered, 5/5 or 5/6 membered mono-spiro heterocyclyl. The spiro heterocyclyl can be substituted or unsubstituted. When substituted, the substituent is preferably one or more groups independently selected from the group consisting of alkyl, alkoxyl, halogen, hydroxy, nitro, cyano, cycloalkyl, heterocyclyl, aryl, heteroaryl, —C(O)OR$_9$, —OC(O)R$_9$, —O(CH$_2$)$_n$C(O)OR$_9$, —OC(O)NR$_{10}$R$_{11}$, carbonyl, —S(O)$_n$R$_9$, —OSO$_2$R$_9$, —SO$_2$NR$_{10}$R$_{11}$, —NHC(O)R$_9$, and —NR$_{10}$R$_{11}$.

p/q membered bicyclic cycloalkyl, bicyclic heterocyclyl, mono-spiro cycloalkyl or mono-spiro heterocyclyl means that the number of ring atoms in two rings of bicyclic cycloalkyl, bicyclic heterocyclyl, mono-spiro cycloalkyl or mono-spiro heterocyclyl are respectively p and q, wherein p and q are each independently selected from the group consisting of an integer from 3 to 8, and preferably an integer from 4 to 7.

"3 to 8 membered heterocyclyl" refers to a monocyclic or bicyclic non-aromatic cyclic group, wherein the number of ring atoms is 3 to 8 membered, one or more ring atoms are heteroatoms selected from the group consisting of nitrogen, oxygen, and S(O)$_n$ (where n is an integer from 0 to 2), the ring can contain 1 to 2 double bonds, and when the ring atom is a nitrogen atom, a bond can be extended from the nitrogen atom. Preferably, it is a 4 to 6 membered heterocyclyl, and more preferably a 5 to 6 membered heterocyclyl, such as pyrrolidinyl, piperidinyl or piperazinyl, etc. The 3 to 8-membered heterocyclyl can be substituted or unsubstituted. When substituted, the substituent is preferably one or more groups independently selected from the group consisting of alkyl, alkoxyl, halogen, hydroxy, nitro, cyano, cycloalkyl, heterocyclyl, aryl, heteroaryl, —C(O)OR$_9$, —OC(O)R$_9$, —O(CH$_2$)$_m$C(O)OR$_9$, —OC(O)NR$_{10}$R$_{11}$, carbonyl, —S(O)$_n$R$_9$, —OSO$_2$R$_9$, —SO$_2$NR$_{10}$R$_{11}$, —NHC(O)R$_9$, and —NR$_{10}$R$_{11}$.

"Aryl" refers to a 6 to 14 membered all-carbon monocyclic ring or polycyclic fused ring (a "fused" ring system means that each ring in the system shares an adjacent pair of carbon atoms with another ring in the system), which has a completely conjugated π-electron system. Preferably, an aryl is 6-10 membered, such as phenyl, naphthyl and anthryl. The aryl can be substituted or unsubstituted. When substituted, the substituent is preferably one or more groups independently selected from the group consisting of alkyl, alkoxyl, halogen, hydroxy, nitro, cyano, cycloalkyl, heterocyclyl, aryl, heteroaryl, —C(O)OR$_9$, —OC(O)R$_9$, —O(CH$_2$)$_n$C(O)OR$_9$, —OC(O)NR$_{10}$R$_{11}$, carbonyl, —S(O)$_n$R$_9$, —OSO$_2$R$_9$, —SO$_2$NR$_{10}$R$_{11}$, —NHC(O)R$_9$, and —NR$_{10}$R$_{11}$.

"Heteroaryl" refers to a heteroaromatic system comprising 5 to 14 ring atoms and 1 to 4 heteroatoms, wherein the heteroatom is oxygen, sulfur or nitrogen. Preferably, a heteroaryl is 5- or 6-membered, such as furyl, thienyl, pyridyl, pyrrolyl, N-alkylpyrrolyl, pyrimidinyl, pyrazinyl, imidazolyl, tetrazolyl etc. The heteroaryl can be substituted or unsubstituted. When substituted, the substituent preferably is one or more groups independently selected from the group consisting of alkyl, alkoxyl, halogen, hydroxy, nitro, cyano, cycloalkyl, heterocyclyl, aryl, heteroaryl, —C(O)OR$_9$, —OC(O)R$_9$, —O(CH$_2$)$_n$C(O)OR$_9$, —OC(O)NR$_{10}$R$_{11}$, carbonyl, —S(O)$_n$R$_9$, —OSO$_2$R$_9$, —SO$_2$NR$_{10}$R$_{11}$, —NHC(O)R$_9$, and —NR$_{10}$R$_{11}$.

"Aryloxyl" refers to —O-aryl and —O-heteroaryl, wherein aryl and heteroaryl are as defined above, such as phenoxyl, pyridinyloxyl, furyloxyl, thienyloxyl, pyrimidinyloxyl, pyrazinyloxyl or derivatives thereof etc.

"Alkoxyl" refers to —O-(alkyl) and —O-(unsubstituted cycloalkyl), such as C$_{1-6}$ alkoxyl, specifically methoxyl, ethoxyl, propoxyl, butoxyl, cyclopropyloxyl, cyclobutyloxyl, cyclopentyloxyl, cyclohexyloxyl, etc. The alkoxyl can be substituted or unsubstituted. When substituted, the substituent is preferably one or more groups independently selected from the group consisting of halogen, alkoxyl, hydroxy, amino, cyano, nitro, cycloalkyl or heterocyclyl.

"Hydroxyl" refers to —OH group.
"Halogen" refers to fluorine, chlorine, bromine or iodine.
"Amino" refers to —NH$_2$.
"Cyano" refers to —CN.
"Nitro" refers to —NO$_2$.
"Bicyclic octyl" refers to

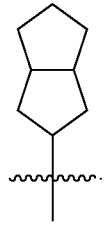 [SMILES: *C1CC2CCCC2C1]

"Azabicyclo octyl" refers to

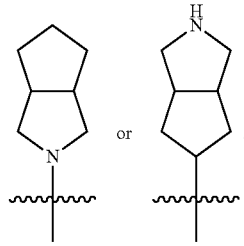

"Optional" or "optionally" means that the subsequently described event or circumstance can, but need not, occur, including the instances in which the event or circumstance does or does not occur. For example, "heterocyclyl optionally substituted by alkyl" means that the alkyl can be, but need not be, present, including the instances when heterocyclyl is substituted or unsubstituted by alkyl.

A "pharmaceutical composition" as used herein means a mixture comprising one or more compounds described in the present invention or physiologically/pharmaceutically acceptable salts or prodrugs thereof, and optionally comprising other components such as physiologically/pharmaceutically acceptable carriers and excipients. The purpose of a pharmaceutical composition is to facilitate administration of a compound to an organism, which will help absorption of the active ingredient, and then to exert biological activity.

m, n and R$_9$~R$_{11}$ are as defined in the compound of formula (I).

Synthesis Method of the Compounds of the Invention

In order to complete the purpose of the present invention, the present invention provides, but is not limited to, the following technical solutions:

A process of preparing a compound of formula (I) or a pharmaceutically acceptable salt thereof of the present invention, comprises a step of:

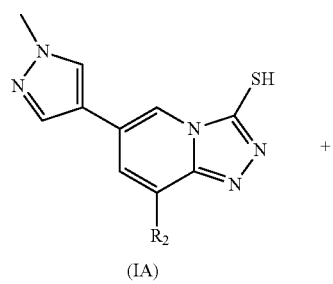

(IA)

+

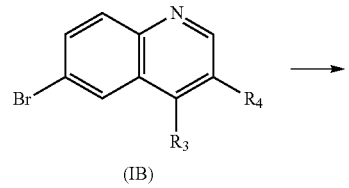

(IB)

→

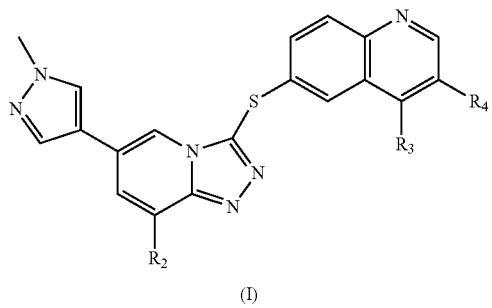

(I)

reacting a compound of formula (IA) with a compound of formula (IB) under an alkaline condition by a S-arylation coupling reaction to give the compound of formula (I); wherein $R_1$, $R_2$, $R_3$ and $R_4$ are as defined previously.

The solvent used in this reaction is selected from the group consisting of 1,4-dioxane, acetonitrile, N,N-dimethylformamide, dimethyl sulfoxide, and N-methylpyrrolidone, preferably 1,4-dioxane, N,N-dimethylformamide, or dimethyl sulfoxide.

The reaction is carried out in the presence of a base, which is selected from the group consisting of an inorganic base (such as sodium carbonate, potassium carbonate, sodium hydrogen carbonate, potassium phosphate, sodium tert-butoxide, potassium tert-butoxide) or an organic base (such as triethylamine, pyridine, piperidine, t-butylamine, diethylisopropylamine), preferably sodium tert-butoxide, potassium tert-butoxide or diethylisopropylamine.

The palladium catalyst used in this reaction can comprise allylpalladium chloride dimer, bis(benzonitrile)palladium chloride, palladium acetate, palladium chloride, tetrakis(triphenylphosphine)palladium, tris(dibenzylideneacetone)dipalladium, or tris(dibenzylideneacetone)dipalladium-chloroform adduct; preferably tris(dibenzylideneacetone)dipalladium, or tris(dibenzylideneacetone)dipalladium-chloroform adduct.

A process of preparing a compound of formula (I) or a pharmaceutically acceptable salt thereof of the present invention, comprises the steps of:

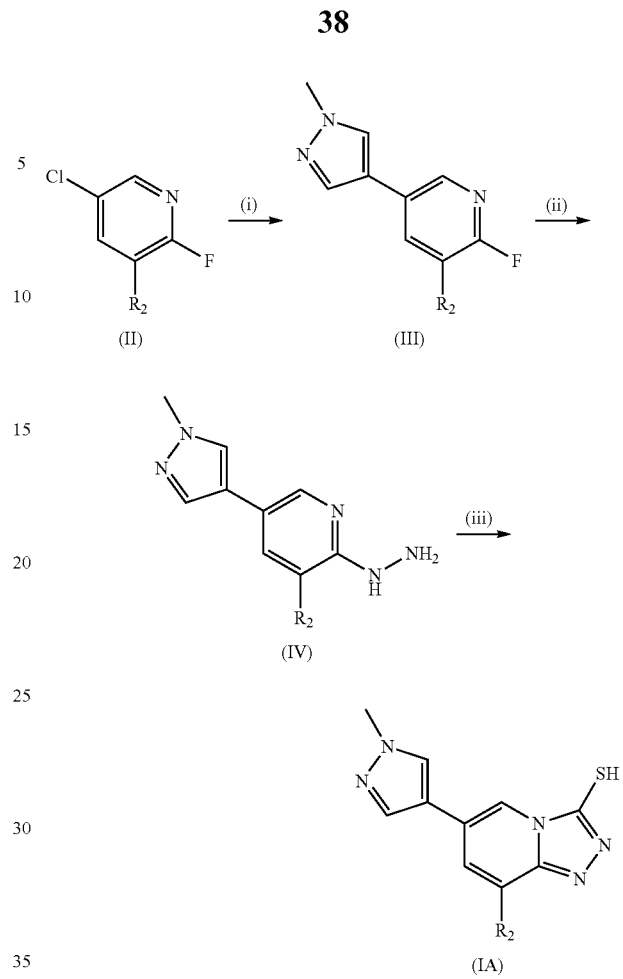

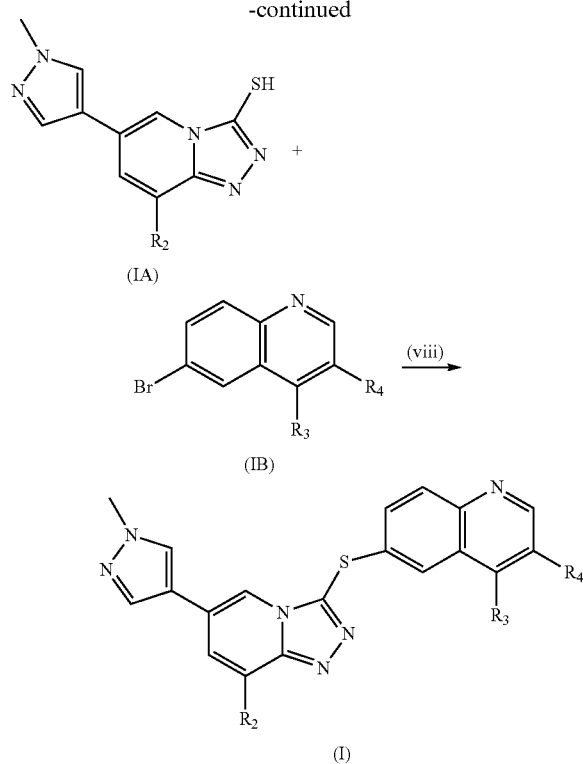

using 1-methyl-4-(4,4,5,5-tetramethyl-1,3,2-dioxaborolan-2-yl)-1H-pyrazole as a raw material of the present synthetic route, via Suzuki reaction, hydrazine substitution, cyclization, to give an intermediate compound (IA); using 6-bromo-4-hydroxy quinoline as a raw material for another fragment, via iodide substitution, chloride substitution, amine substitution, alkoxyl substitution or halogen exchange, to give an intermediate (IB), and then reacting the intermediate compound (IA) with the intermediate compound (IB) by a S-arylation coupling reaction to give the target compound (I).

DETAILED DESCRIPTION OF THE INVENTION

The following examples are used to further describe the invention, but these examples are not intended to limit the scope of the invention.

Structures of compounds were identified by nuclear magnetic resonance (NMR) and/or mass spectrometry (MS). NMR chemical shifts (δ) are given in $10^{-6}$ (ppm). NMR was determined by a Bruker AVANCE-400 instrument. The solvents were deuterated dimethyl sulfoxide (DMSO-$d_6$) and deuterated chloroform (CDCl$_3$). The internal standard was tetramethylsilane (TMS).

MS was determined by a FINNIGAN LCQAd (ESI) mass spectrometer (Manufacturer: Thermo, Model: Finnigan LCQ advantage MAX).

High performance liquid chromatography (HPLC) was determined by an Agilent 1200DAD high pressure liquid chromatography spectrometer (Sunfire C18 150×4.6 mm chromatographic column) and a Waters 2695-2996 high pressure liquid chromatography spectrometer (Gimini C18 150×4.6 mm chromatographic column).

The average inhibition rate of kinase and IC$_{50}$ values were determined by a NovoStar microplate reader (BMG Co., Germany).

For thin-layer silica gel chromatography (TLC) Yantai Huanghai HSGF254 or Qingdao GF254 silica gel plate was used. The dimension of the plates used in TLC was 0.15 mm to 0.2 mm, and the dimension of the plates used in product purification was 0.4 mm to 0.5 mm.

Column chromatography generally used Yantai Huanghai 200 to 300 mesh silica gel as a carrier.

The known starting materials used in the examples of the present invention can be commercially available, or can be synthesized by methods known in the field.

Unless otherwise stated, all the reactions of the present invention were under continuous magnetic stirring and under dry nitrogen or argon atmosphere.

Argon or nitrogen atmosphere means that a reaction flask is equipped with about 1 L volume argon or nitrogen balloon.

Hydrogen atmosphere means that a reaction flask is equipped with about 1 L hydrogen balloon.

Unless otherwise stated in the examples, the solution refers to an aqueous solution.

Unless otherwise stated in the examples, the reaction temperature was room temperature.

Room temperature is the optimum reaction temperature, and ranged from 20° C. to 30° C.

The reaction progress in the examples was monitored by thin layer chromatography (TLC), and the system of developing solvent included: dichloromethane and methanol system, n-hexane and ethyl acetate system, petroleum ether and ethyl acetate system, and acetone. The volume ratio of solvent was adjusted according to the polarity of the compound.

The elution system for column chromatography included: A: dichloromethane and methanol system, B: n-hexane and ethyl acetate system, C: dichloromethane and ethyl acetate system, D: ethyl acetate and methanol system. The volume ratio of solvent was adjusted according to the polarity of the compound, and a small amount of ammonia and acetic acid can be added.

EXAMPLES

Example 1

8-fluoro-6-(1-methyl-1H-pyrazol-4-yl)-[1,2,4]triazolo[4,3-a]pyridin-3-thiol (1)

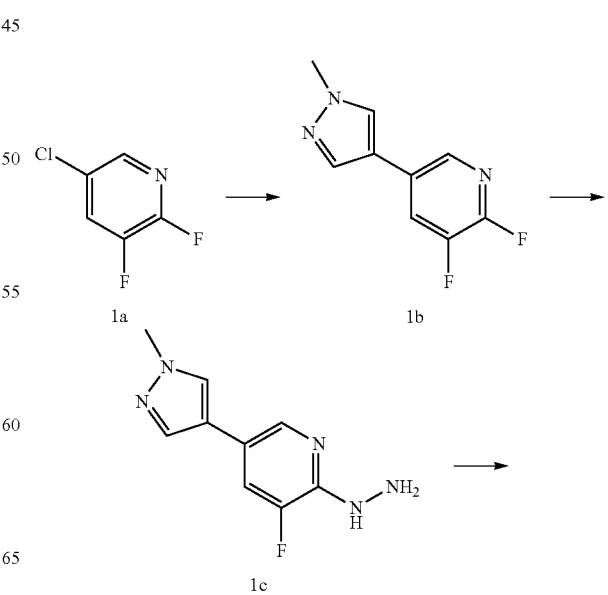

-continued

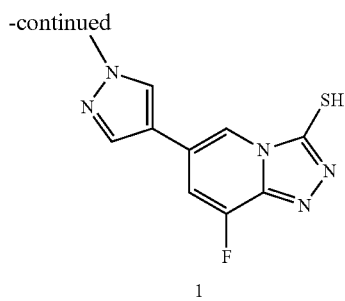

1

Step 1:
2,3-difluoro-5-(1-methyl-1H-pyrazol-4-yl)pyridine
1b

To a 250 mL one-necked flask, 5-chloro-2,3-difluoropyridine (6.16 g, 41.2 mmol), 1-methyl-4-(4,4,5,5-tetramethyl-1,3,2-dioxaborolan-2-yl)-1H-pyrazole (10.26 g, 49.4 mmol), palladium acetate (464 mg, 2.06 mmol), 2-dicyclohexylphosphoro-2,4,6-triisopropylbiphenyl (1.96 g, 4.12 mmol), potassium phosphate (26.24 g, 123.6 mmol), and dioxane/water (80 mL/8 mL) were added. The reaction mixture was purged with $N_2$ three times, and then heated to 100° C. overnight under $N_2$. After LC-MS showed completion of the reaction, silica was added. The solvent was directly removed by rotary evaporation, and the residue was purified by column chromatography using petroleum ether/ethyl acetate (5/1 to 3/1) as elution to give 2,3-difluoro-5-(1-methyl-1H-pyrazol-4-yl)pyridine 1b (6.1 g, yield 76%) as a white solid.

MS m/z (ESI): 196.0

$^1$H NMR (400 MHz, CDCl$_3$, ppm) δ 8.32-8.25 (m, 3H), 8.01 (d, J=0.4 Hz, 1H), 3.88 (s, 3H).

Step 2: 3-fluoro-2-hydrazinyl-5-(1-methyl-1H-pyrazol-4-yl)pyridine 1c

To a 50 mL one-necked flask, 2,3-difluoro-5-(1-methyl-1H-pyrazol-4-yl)pyridine (1.8 g, 9.2 mmol), 85% hydrazine hydrate (1.8 g, 46 mmol) and ethanol (25 mL) were added. The reaction mixture was heated to reflux overnight under $N_2$. Then the reaction mixture was cooled to room temperature, and the resulting white solid was filtered and washed with cold ethanol to give 3-fluoro-2-hydrazinyl-5-(1-methyl-1H-pyrazol-4-yl)pyridine 1c (1.4 g, yield 73%) as a white needle solid.

MS m/z (ESI): 208.0

Step 3: 8-fluoro-6-(1-methyl-1H-pyrazol-4-yl)-[1,2,4]triazolo[4,3-a]pyridin-3-thiol 1

To a 50 mL one-necked flask, 3-fluoro-2-hydrazinyl5-(1-methyl-1H-pyrazol-4-yl)pyridine (1.4 g, 6.7 mmol), carbon disulfide (1.0 g, 13.4 mmol), potassium hydroxide (395 mg, 7.0 mmol) and ethanol/water (20 mL/5 mL) were added. The reaction mixture was heated to reflux for 46 hours under $N_2$. The solvent was removed by rotary evaporation, and the residue was dissolved in sodium hydroxide aqueous solution (1 M, 30 mL), then water was added until the solids dissolved. The aqueous phase was extracted twice with dichloromethane, and then the aqueous phase was separated and acidified with hydrochloric acid (1 M). A lot of yellow solid was precipitated, and the solution was left to stand for 1 hour, then filtered by slow filter paper and washed with water to give the product 8-fluoro-6-(1-methyl-1H-pyrazol-4-yl)-[1,2,4]triazolo[4,3-a]pyridin-3-thiol (1.1 g, yield 68%) as a pale yellow solid.

MS m/z (ESI): 249.96

$^1$H NMR (400 M, DMSO-d$_6$, ppm) δ 14.89 (s, 1H), 8.39 (s, 1H), 8.23 (s, 1H), 8.04 (s, 1H), 7.81 (dd, J=1.2, 12.4 Hz, 1H), 3.88 (s, 3H).

Example 2

6-((8-fluoro-6-(1-methyl-1H-pyrazol-4-yl)-[1,2,4]triazolo[4,3-a]pyridin-3-yl)thio)-4-methoxy-2-quinoline (2)

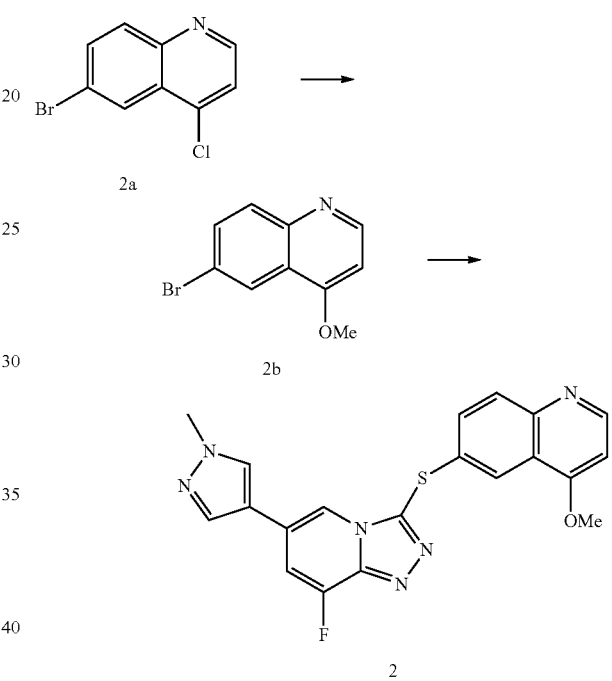

Step 1: 6-bromo-4-methoxy-quinoline 2b

To a 10 mL one-necked flask, 6-bromo-4-chloro-quinoline (0.50 g, 2.06 mmol), methanol (5 mL) and sodium methoxide (0.56 g, 10.3 mmol) were added successively, and the reaction mixture was heated to 50° C. overnight. After TLC showed completion of the reaction, silica was added. The solvent was removed by rotary evaporation, and the residue was purified by silica gel chromatography (petroleum ether/acetone=10/1) to give 6-bromo-4-methoxy-quinoline 2b (0.25 g, yield 51%) as a white solid.

MS m/z (ESI): 238.0

Step 2: 6-((8-fluoro-6-(1-methyl-1H-pyrazol-4-yl)-[1,2,4]triazolo[4,3-a]pyridin-3-yl)thio)-4-methoxy-2-quinoline (2)

To a 25 mL one-necked flask, 8-fluoro-6-(1-methyl-1H-pyrazol-4-yl)-[1,2,4]triazolo[4,3-a]pyridin-3-thiol (100 mg, 0.4 mmol), 6-bromo-4-methoxy-quinoline (95 mg, 0.4 mmol), tris(dibenzylideneacetone)dipalladium (37 mg, 0.04 mmol), 4,5-bis(diphenylphosphino)-9,9-dimethylxanthene (46 mg, 0.08 mmol) and anhydrous N,N-dimethylformamide (5 mL) were added. The reaction mixture was purged with N₂ 3 times and stirred for 5 minutes at room temperature under N₂ until the solids were dissolved, and then N,N-diisopropylethylamine (162 mg, 1.6 mmol) was added. The reaction mixture was heated to 100° C. overnight. After LC-MS showed completion of the reaction, N,N-dimethylformamide was removed by rotary evaporation, and the residue was purified by column chromatography (dichloromethane/methanol=20/1) to give 6-((8-fluoro-6-(1-methyl-1H-pyrazol-4-yl)-[1,2,4]triazolo[4,3-a]pyridin-3-yl) thio)-4-methoxy-2-quinoline (2.1 mg) as a white solid.

¹H NMR (400 MHz, CDCl₃, ppm): δ 8.76 (s, 1H), 8.26 (s, 1H), 8.09 (m, 2H), 7.65 (m, 3H), 7.19 (dd, J=10.0 Hz, 0.4 Hz, 1H), 6.83 (d, J=5.2 Hz, 1H), 4.09 (s, 3H), 3.97 (s, 3H).

MS m/z (ESI): 407.1.

Example 3

9-((8-fluoro-6-(1-methyl-1H-pyrazol-4-yl)-[1,2,4]-triazolo[4,3-a]pyridin-3-yl)thio)-2,3-dihydro-[1,4] dioxino[2,3-c]quinoline (3)

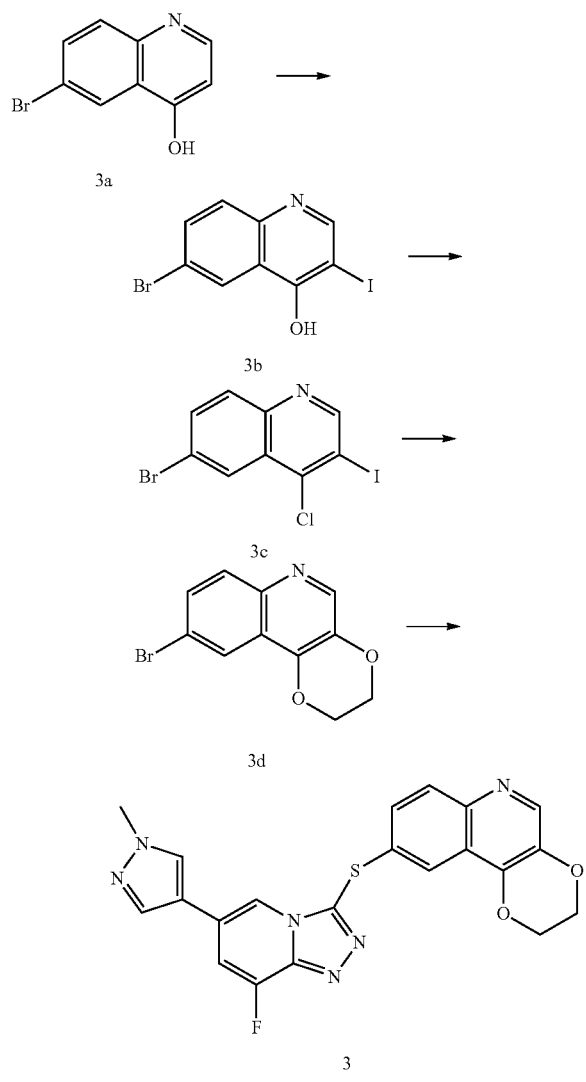

Step 1: 6-bromo-3-iodoquinolin-4-ol 3b

To a 50 mL one-necked flask, 6-bromoquinolin-4-ol (15 g, 66.95 mmol), 1-iodopyrrolidine-2,5-dione (12.05 g, 53.56 mmol) and ethyl acetate (400 mL) were added. The reaction mixture was heated to 60° C. for 4.5 hours, and then cooled to room temperature. The solid was collected by filtration, and placed in a 2 liter beaker. Sodium carbonate aqueous solution was added to adjust the pH to 7, and then sodium bicarbonate aqueous solution was added to adjust the pH to 8-9. The reaction solution was left to stand for 1 hour, and filtered to give an off-white solid. The grey solid was washed with water (it can be washed with cold acetone if a purer product is needed) and dried to give 6-bromo-3-iodoquinolin-4-ol 3b (18 g, yield 77%) as a white solid.

MS m/z (ESI): 349.7

Step 2: 6-bromo-4-chloro-3-iodoquinoline 3c

To a 250 mL sealed tube, 6-bromine-3-iodoquinolin-4-ol (25 g, 71.4 mmol) and phosphorus oxychloride (150 mL) were added. The reaction mixture was heated to 100° C. overnight to give a red solution. After LC-MS showed completion of the reaction, the reaction was cooled to room temperature, then the reaction mixture was added to warm water (35° C., 20 mL) slowly under stirring, and the temperature of the solution was controlled at 30-45° C. by addition of ice and in an ice water bath. When the addition was completed, the mixture was stirred for a further 15 minutes. Then the solid was filtered by a Büchner funnel, and washed with water. The solid was placed in a 2 liter beaker, and sodium carbonate aqueous solution was added to adjust the pH to 8-9. The resulting mixture was stirred for 1 hour, and left to stand for 30 minutes, filtered, washed with water, and dried to give 6-bromo-4-chloro-3-iodoquinoline 3c (22 g, yield 84%) as a pale yellow solid.

MS m/z (ESI): 367.6

Step 3: 9-bromo-2,3-dihydro-[1,4]dioxino[2,3-c]quinoline 3d

To a 250 mL sealed tube, 6-bromo-3-iodo-quinolin-4-ol (3.7 g, 10.0 mmol), cesium carbonate (9.8 g, 30.12 mmol), cuprous iodide (382 mg, 2.0 mmol), and ethylene glycol (100 mL) were added, and then the reaction mixture was heated to 100° C. overnight. After LC-MS showed completion of the reaction, the reaction mixture was cooled to room temperature, most of the solvent was removed by vacuum rotary evaporation, and then the mixture was added to water and extracted with ethyl acetate. The organic phases were combined, washed three times with saturated sodium chloride solution, then the organic phase was dried over potassium carbonate and purified by column chromatography (2% methanol in dichloromethane) to give 9-bromo-2,3-dihydro-[1,4]dioxino[2,3-c]quinoline 3d (800 mg, yield 30%) as a white solid.

MS m/z (ESI): 266.0

Step 4: 9-((8-fluoro-6-(1-methyl-1H-pyrazol-4-yl)-[1,2,4]triazolo[4,3-a]pyridin-3-yl)thio)-2,3-dihydro-[1,4]dioxino[2,3-c]quinoline 3

To a 25 mL one-necked flask, 8-fluoro-6-(1-methyl-1H-pyrazol-4-yl)-[1,2,4]triazolo[4,3-a]pyridin-3-thiol (132 mg, 0.53 mmol), 9-bromo-2,3-dihydro-[1,4]dioxino[2,3-c]quinoline (128 mg, 0.481 mmol), tris(dibenzylideneacetone)

dipalladium (66 mg, 0.072 mmol), 4,5-bis(diphenylphosphino)-9,9-dimethylxanthene (83 mg, 0.144 mmol) and anhydrous N,N-dimethylformamide (8 mL) were added. The reaction mixture was purged with $N_2$ 3 times and stirred for 5 minutes at room temperature under $N_2$ until the solids were dissolved. Sodium tert-butoxide (58 mg, 0.608 mmol) was added, stirred at room temperature for 5 minutes, then heated to 100° C. overnight. After the reaction was stopped, N,N-dimethylformamide was removed by rotary evaporation, the residue was dissolved in dichloromethane, washed twice with water, then concentrated and purified by reverse phase column chromatography to give 9-((8-fluoro-6-(1-methyl-1H-pyrazol-4-yl)-[1,2,4]triazolo[4,3-a]pyridin-3-yl)thio)-2,3-dihydro-[1,4]dioxino[2,3-c]quinoline 3.

MS m/z (ESI): 321.1

$^1$H NMR (400 MHz, CDCl$_3$, ppm): δ 8.52 (s, 1H), 8.04 (s, 1H), 7.99 (s, 1H), 7.95 (d, J=8.8 Hz, 1H), 7.67 (s, 1H), 7.59 (s, 1H), 7.47 (d, J=8.4 Hz, 1H), 7.16 (d, J=10.4 Hz, 1H), 4.49 (s, 2H), 4.39 (s, 2H), 3.95 (s, 3H).

Example 4

1-(6-((8-fluoro-6-(1-methyl-1H-pyrazol-4-yl)-[1,2,4]triazolo[4,3-a]pyridin-3-yl)thio)-4-methoxyquinolin-3-yl)pyrrolidin-2-one (4)

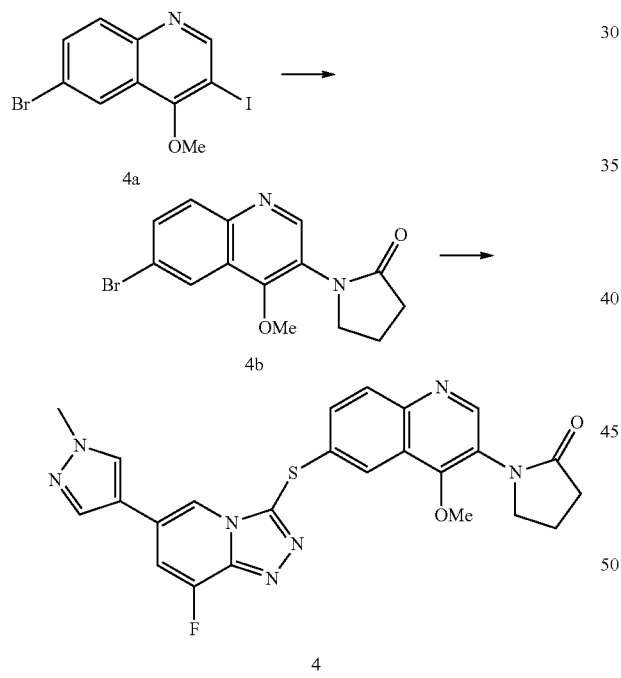

Step 1:
1-(6-bromo-4-methoxyquinolin-3-yl)pyrrolidin-2-one 4b

To a 25 mL one-necked flask, 6-bromo-3-iodo-4-methoxyquinoline (0.6 g, 1.65 mmol), cuprous iodide (0.18 g, 0.19 mmol), potassium phosphate (0.7 g, 3.3 mmol), and dimethyl sulfoxide (10 mL) were added. The reaction mixture was purged with $N_2$ three times, then pyrrolidin-2-one (0.18 g, 2.12 mmol) and N,N'-dimethylethanediamine (36 mg, 0.41 mmol) were added under $N_2$. The reaction mixture was heated to 50° C. overnight, and then ethyl acetate (100 mL) was added. The resulting solution was washed three times with saturated sodium chloride aqueous solution, the organic phase was dried over anhydrous sodium sulfate, and concentrated. The resulting residue was purified by silica gel column chromatography (eluting solvent: ethyl acetate) to give 1-(6-bromo-4-methoxyquinolin-3-yl)pyrrolidin-2-one (0.3 g, yield 56%) as a yellow solid.

MS m/z (ESI): 321.1

Step 2: 1-(6-((8-fluoro-6-(1-methyl-1H-pyrazol-4-yl)-[1,2,4]triazolo[4,3-a]pyridin-3-yl)thio)-4-methoxyquinolin-3-yl)pyrrolidin-2-one 4

To a 25 mL one-necked flask, 1-(6-bromo-4-methoxyquinolin-3-yl)pyrrolidin-2-one (116 mg, 0.47 mmol), 8-fluoro-6-(1-methyl-1H-pyrazol-4-yl)-[1,2,4]triazolo[4,3-a]pyridin-3-thiol (150 mg, 0.47 mmol), tris(dibenzylideneacetone)dipalladium (43 mg, 0.047 mmol), 4,5-bis(diphenylphosphino)-9,9-dimethylxanthene (54 mg, 0.01 mmol) and anhydrous N,N-dimethylformamide (6 mL) were added. The reaction mixture was purged with $N_2$, and stirred for 5 minutes at room temperature until the solids were dissolved. Sodium tert-butoxide (54 mg, 0.56 mmol) was added, stirred at room temperature for 5 minutes, and then heated to 100° C. overnight. After LC-MS showed the reaction was completed. N,N-dimethylformamide was removed by rotary evaporation, the resulting solid was dissolved with dichloromethane, washed twice with water and concentrated. The residue was purified by column chromatography (dichloromethane/methanol=20/1) to give 1-(6-((8-fluoro-6-(1-methyl-1H-pyrazol-4-yl)-[1,2,4]triazolo[4,3-a]pyridin-3-yl)thio)-4-methoxyquinolin-3-yl)pyrrolidin-2-one 4 (10 mg) as a white solid.

MS m/z (ESI): 490.2

$^1$H NMR (400 MHz, CDCl$_3$, ppm): δ 8.71 (s, 1H), 8.12 (s, 1H), 8.06 (m, 2H), 7.68 (s, 1H), 7.60 (m, 1H), 7.27 (s, 1H), 7.19 (d, J=10.4 Hz, 1H), 4.03 (s, 3H), 3.95 (s, 3H), 3.84 (t, J=6.8 Hz, 2H), 2.63 (t, J=8.0 Hz, 2H), 2.32 (m, 2H).

Example 5

4-fluoro-6-((8-fluoro-6-(1-methyl-1H-pyrazol-4-yl)-[1,2,4]triazolo[4,3-a]pyridin-3-yl)thio)-3-(1-methyl-1H-pyrazol-4-yl)quinoline (5)

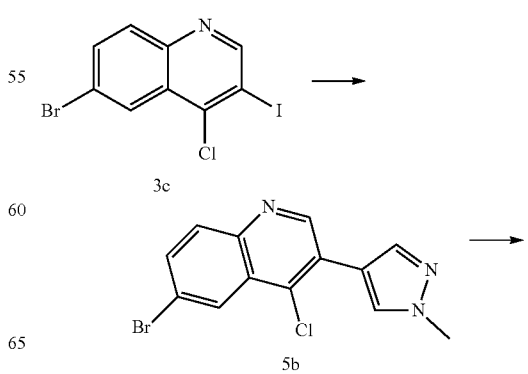

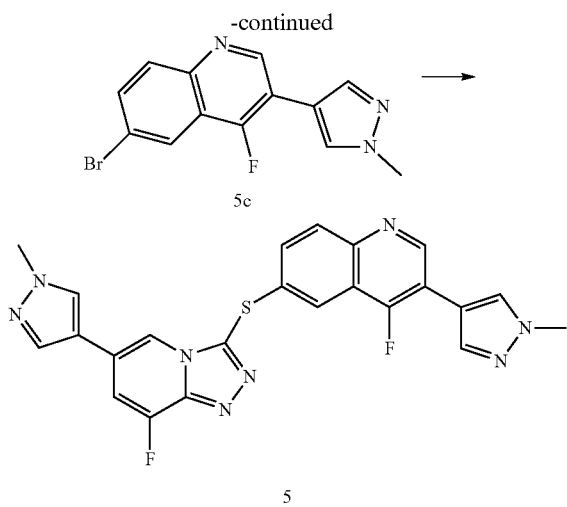

Step 1: 6-bromo-4-chloro-3-(1-methyl-1H-pyrazol-4-yl)quinoline 5b

To a 250 mL one-necked flask, 6-bromo-4-chloro-3-iodoquinoline (1.1 g, 3.0 mmol), 1-methyl-4-(4,4,5,5-tetramethyl-1,3,2-dioxaboronolan-2-yl)-1H-pyrazole (0.75 g, 3.6 mmol), [1,1'-bis(diphenylphosphino)ferrocene]palladium dichloride (0.22 g, 0.3 mmol), potassium carbonate (0.83 g, 6.0 mmol) and dioxane/water (50 mL/10 mL) were added. The reaction mixture was purged with $N_2$ three times, then heated to 35° C. overnight. After LC-MS showed completion of the reaction, silica gel was added to the reaction mixture, and the solvent was directly removed by rotary evaporation, and the residue was purified by column chromatography (petroleum ether/ethyl acetate (10:1 to 1:1)) to give 6-bromo-4-chloro-3-(1-methyl-1H-pyrazol-4-yl)quinoline (0.5 g, yield 52%) as a white solid.

MS m/z (ESI): 322.0

Step 2: 6-bromo-4-fluoro-3-(1-methyl-1H-pyrazol-4-yl)quinoline 5c

To a 15 mL sealed tube, 6-bromo-4-chloro-3-(1-methyl-1H-pyrazol-4-yl)quinoline (0.2 g, 0.62 mmol), cesium fluoride (0.59 g, 3.1 mmol) and dry dimethyl sulfoxide (8 mL) were added, then the reaction mixture was heated to 90° C. for 3 hours. After LC-MS showed completion of the reaction, the reaction mixture was poured into 50 mL ethyl acetate, and washed with saturated sodium chloride three times. The organic phases were combined, dried over anhydrous sodium sulfate and concentrated. The residue was purified by column chromatography (ethyl acetate) to give 6-bromo-4-fluoro-3-(1-methyl-1H-pyrazol-4-yl)quinoline (0.19 g, yield 100%) as a white solid.

MS m/z (ESI): 306.0

Step 3: 4-fluoro-6-((8-fluoro-6-(1-methyl-1H-pyrazol-4-yl)-[1,2,4]triazolo[4,3-a]pyridin-3-yl)thio)-3-(1-methyl-1H-pyrazol-4-yl)quinoline 5

To a 25 mL one-necked flask, 8-fluoro-6-(1-methyl-1H-pyrazol-4-yl)-[1,2,4]triazolo[4,3-a]pyridin-3-thiol (98 mg, 0.39 mmol), 6-bromo-4-fluoro-3-(1-methyl-1H-pyrazol-4-yl)quinoline (120 mg, 0.39 mmol), tris(dibenzylideneacetone)dipalladium (36 mg, 0.039 mmol), 4,5-bis(diphenylphosphino)-9,9-dimethylxanthene (45 mg, 0.078 mmol) and anhydrous N,N-dimethylformamide (5 mL) were added. The reaction mixture was purged with $N_2$ three times, and stirred for 5 minutes at room temperature until the solids were dissolved. Sodium tert-butoxide (41 mg, 0.43 mmol) was added to the reaction mixture, the resulting mixture was stirred at room temperature for 5 minutes, then heated to 100° C. for 6 hours. After LC-MS showed completion of the reaction, N,N-dimethylformamide was removed by rotary evaporation, and the resulting solid was dissolved in dichloromethane, washed twice with water and concentrated. The residue was purified by column chromatography (dichloromethane: methanol=20:1) to give 4-fluoro-6-((8-fluoro-6-(1-methyl-1H-pyrazol-4-yl)-[1,2,4]triazolo[4,3-a]pyridin-3-yl)thio)-3-(1-methyl-1H-pyrazol-4-yl)quinoline 5 (2.9 mg) as a white solid.

MS m/z (ESI): 475.1

$^1$H NMR (400 MHz, DMSO-$d_6$, ppm): δ 9.28 (d, J=10.4 Hz, 1H), 8.60 (s, 1H), 8.40 (d, J=13.6 Hz, 2H), 8.09 (m, 3H), 8.01 (d, J=8.8 Hz, 1H), 7.87 (d, J=12.0 Hz, 1H), 7.59 (dd, J=8.8, 1.6 Hz, 1H), 3.94 (s, 3H), 3.85 (s, 3H).

Example 6

3-(6-((8-fluoro-6-(1-methyl-1H-pyrazol-4-yl)-[1,2,4]triazolo[4,3-a]pyridin-3-yl)thio)-4-methoxyquinolin-3-yl)oxazolidin-2-one (6)

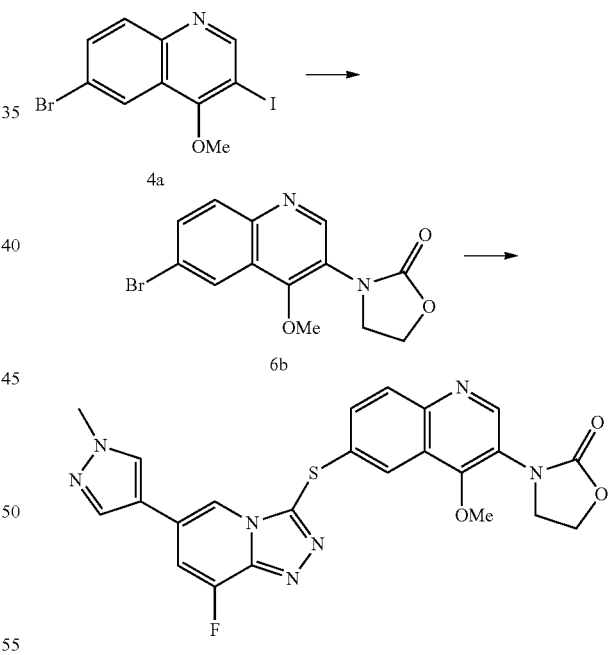

Step 1: 3-(6-bromo-4-methoxyquinolin-3-yl)oxazolidin-2-one 6b

To a 25 mL one-necked flask, 6-bromo-3-iodo-4-methoxyquinoline (0.2 g, 0.55 mmol), oxazolidin-2-one (0.07 g, 0.83 mmol), cuprous iodide (0.05 g, 0.28 mmol), and potassium phosphate (0.18 g, 0.83 mmol) and dimethyl sulfoxide (5 mL) were added. The reaction mixture was purged with N₂ 3 times, and then N,N'-dimethylethanediamine (0.05 g, 0.55 mmol) was added, and the reaction mixture was heated to 35° C. overnight. The reaction solution was diluted with ethyl acetate (50 mL), washed with saturated sodium chloride aqueous solution three times, the organic phase was dried over anhydrous sodium sulfate, and concentrated. The resulting residue was purified by silica gel column chromatography (ethyl acetate) to give 3-(6-bromo-4-methoxyquinolin-3-yl)-oxazolidin-2-one (0.08 g, yield 45%) as a yellow solid.

MS m/z (ESI): 323.0

Step 2: 3-(6-((8-fluoro-6-(1-methyl-1H-pyrazol-4-yl)-[1,2,4]triazolo[4,3-a]pyridin-3-yl)thio)-4-methoxyquinolin-3-yl)oxazolidin-2-one 6

To a 25 mL one-necked flask, 8-fluoro-6-(1-methyl-1H-pyrazol-4-yl)-[1,2,4]triazolo[4,3-a]pyridin-3-thiol (137 mg, 0.55 mmol), 3-(6-bromo-4-methoxyquinolin-3-yl)oxazolidin-2-one (160 mg, 0.50 mmol), tris(dibenzylideneacetone)dipalladium (46 mg, 0.05 mmol), 4,5-bis(diphenylphosphino)-9,9-dimethylxanthene (58 mg, 0.1 mmol) and anhydrous N,N-dimethylformamide (5 mL) were added. The reaction mixture was purged with N₂ three times and stirred at room temperature until the solids were dissolved. Sodium tert-butoxide (55 mg, 0.58 mmol) was added to the reaction mixture and stirred at room temperature for 5 minutes, then heated to 100° C. for 5 h. After LC-MS showed completion of the reaction, N,N-dimethylformamide was removed by rotary evaporation, and the resulting solid was dissolved in dichloromethane, washed with water twice and concentrated to give a residue. The residue was purified by reverse phase column chromatography (20% acetonitrile in water) to give 3-(6-((8-fluoro-6-(1-methyl-1H-pyrazol-4-yl)-[1,2,4]triazolo[4,3-a]pyridin-3-yl)thio)-4-methoxyquinolin-3-yl)oxazolidin-2-one 6 (2.6 mg) as a white solid.

MS m/z (ESI): 492.1
¹H NMR (400 MHz, DMSO-d₆, ppm): δ 8.84 (s, 1H), 8.59 (s, 1H), 8.38 (s, 1H), 8.16 (s, 1H), 8.09 (s, 1H), 7.96 (d, J=8.8 Hz, 1H), 7.86 (d, J=12.0 Hz, 1H), 7.61 (d, J=9.2 Hz, 1H), 4.56 (t, J=7.8 Hz, 2H), 4.05 (m, 5H), 3.86 (s, 3H).

Example 7

(S)-9-((8-fluoro-6-(1-methyl-1H-pyrazol-4-yl)-[1,2,4]triazolo[4,3-a]pyridin-3-yl)thio)-2,3,12,12a-tetrahydro-1H-pyrrolo[1',2':4,5][1,4]oxazino[3,2-c]quinoline (7)

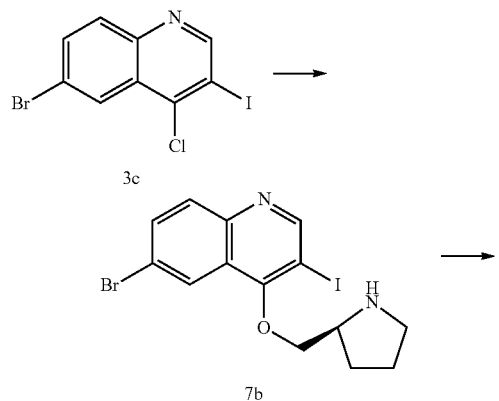

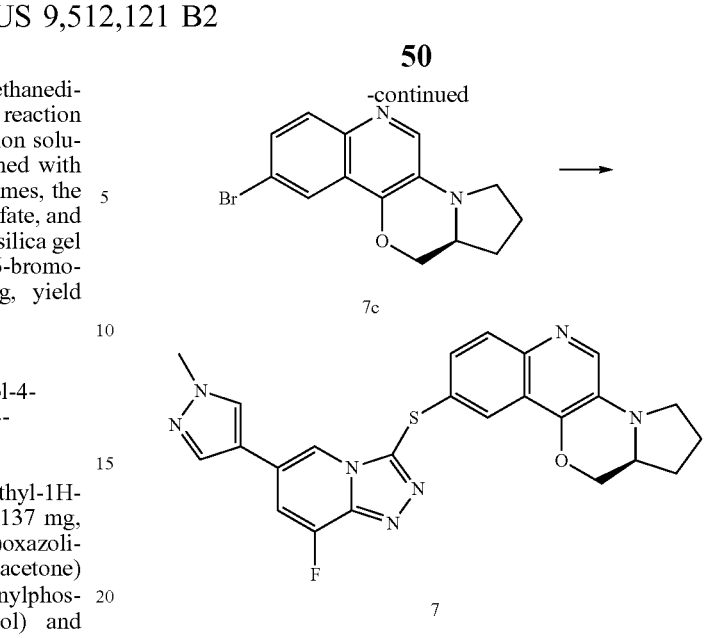

Step 1: (S)-6-bromo-3-iodo-4-(pyrrolidin-2-ylmethoxy)quinoline 7b

To a 25 mL one-necked flask, (S)-pyrrolidine-2-ylmethanol (0.165 g, 1.63 mmol) and anhydrous tetrahydrofuran (5 mL) were added. The reaction mixture was purged with N₂ 3 times and stirred for 5 minutes at room temperature. Sodium hydride (46 mg, 0.05 mmol) was added and stirred at room temperature for another 15 minutes.

A solution of 6-bromo-4-chloro-3-iodoquinoline 3c (0.3 g, 0.81 mmol) in THF (10 mL) was added dropwise. After the addition was completed, the reaction mixture was stirred for 30 minutes at room temperature, then heated to 40° C. for 3 hours. After LC-MS showed completion of the reaction, silica gel was added to the reaction mixture, the solvent was removed, and the resulting residue was purified by column chromatography to give (S)-6-bromo-3-iodo-4-(pyrrolidin-2-ylmethoxy)quinoline (0.182 g, yield 51%) as a white solid.

MS m/z (ESI): 432.9

Step 2: (S)-9-bromo-2,3,12,12a-tetrahydro-1H-pyrrolo[1',2':4,5][1,4]oxazino[3,2-c]quinoline To a 25 mL one-necked flask, (S)-6-bromo-3-iodo-4-(pyrrolidin-2-ylmethoxy)quinoline (0.17 g, 0.39 mmol), cesium carbonate (0.38 g, 1.18 mmol), copper iodide (0.075 mg, 0.39 mmol) and N,N-dimethylformamide (8 mL) were added. The reaction mixture was purged with N₂ three times, then heated to 100° C. overnight. After LC-MS showed completion of the reaction, the reaction mixture was cooled to room temperature, the solvent was removed by rotary evaporation, the resulting residue was dissolved in dichloromethane, and washed with saturated sodium chloride aqueous solution three times. The organic phase was dried over anhydrous sodium sulfate, concentrated and purified by silica gel column chromatography (dichloromethane) to give (S)-9-bromo-2,3,12,12a-tetrahydro-1H-pyrrolo[1',2':4,5][1,4]oxazino[3,2-c]quinoline (0.065 g, yield 54%) as a white solid.

MS m/z (ESI): 305.0

Step 3: (S)-9-((8-fluoro-6-(1-methyl-1H-pyrazol-4-yl)-[1,2,4]triazolo[4,3-a]pyridin-3-yl)thio)-2,3,12,12a-tetrahydro-1H-pyrrolo[1',2':4,5][1,4]oxazino[3,2-c]quinoline 7

To a 25 mL one-necked flask, 8-fluoro-6-(1-methyl-1H-pyrazol-4-yl)-[1,2,4]triazolo[4,3-a]pyridin-3-thiol (65 mg, 0.26 mmol), (S)-9-bromo-2,3,12,12a-tetrahydro-1H-pyrrolo[1',2':4,5][1,4]oxazino[3,2-c]quinoline (80 mg, 0.26 mmol), tri(dibenzenylpropanone)dipalladium (24 mg, 0.026 mmol), 4,5-bis(diphenylphosphino)-9,9-dimethylxanthene (30 mg, 0.052 mmol) and anhydrous N,N-dimethylformamide (5 mL) were added. The reaction mixture was purged with $N_2$, and stirred for 5 minutes at room temperature until the solids were dissolved. Sodium tert-butoxide (30 mg, 0.31 mmol) was then added and stirred at room temperature for another 5 minutes, and then heated to 100° C. for 5 hours. After LC-MS showed completion of the reaction, DMF was removed by rotary evaporation. The resulting residue was dissolved in dichloromethane, washed with water twice and concentrated. The resulting residue was purified by reverse phase column chromatography (40% acetonitrile in water) to give (S)-9-((8-fluoro-6-(1-methyl-1H-pyrazol-4-yl)-[1,2,4]triazolo[4,3-a]pyridin-3-yl)thio)-2,3,12,12a-tetrahydro-1H-pyrrolo[1',2':4,5][1,4]oxazino[3,2-c]quinoline 7 (5.1 mg) as a white solid.
MS m/z (ESI): 473.9
$^1$H NMR (400 MHz, CDCl$_3$, ppm): δ 8.41 (s, 1H), 8.05 (s, 1H), 8.00 (s, 1H), 7.90 (d, J=8.8 Hz, 1H), 7.67 (s, 1H), 7.58 (s, 1H), 7.45 (d, J=8.8 Hz, 1H), 7.15 (d, J=10.8 Hz, 1H), 4.30 (dd, J=10.0 Hz, 2.4 Hz, 2H), 3.95 (m, 4H), 3.56 (t, J=8.8 Hz, 1H), 3.40 (m, 2H), 2.31 (m, 1H), 2.02 (m, 1H), 1.82 (m, 2H).

Example 8

(R)-9-((8-fluoro-6-(1-methyl-1H-pyrazol-4-yl)-[1,2,4]triazolo[4,3-a]pyridin-3-yl)thio)-2,3,12,12a-tetrahydro-1H-pyrrolo[1',2':4,5][1,4]oxazino[3,2-c]quinoline (8)

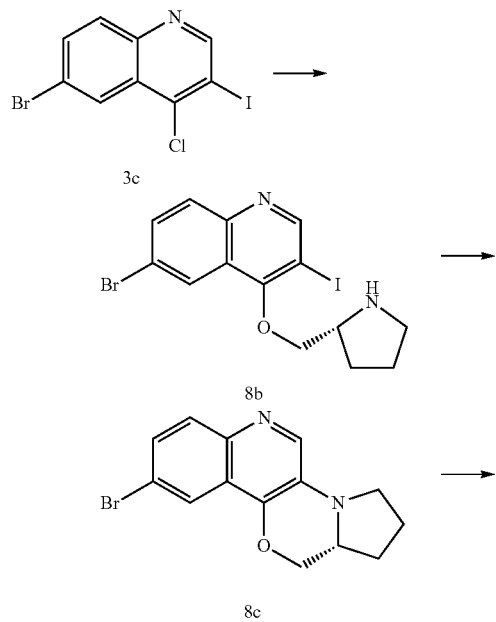

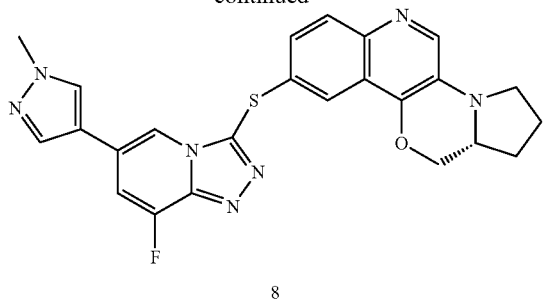

Compound 8 was synthesized from (R)-pyrrolidin-2-yl methanol by reference to the process of synthesizing compound 7.
$^1$H NMR (400 MHz, CDCl$_3$, ppm): δ 8.34 (s, 1H), 8.04 (d, J=1.2 Hz, 1H), 7.94 (d, J=2.0 Hz, 1H), 7.81 (d, J=8.8 Hz, 1H), 7.64 (m, 2H), 7.36 (dd, J=8.8 Hz, 2.4 Hz, 1H), 7.12 (dd, J=9.6 Hz, 0.8 Hz, 1H), 4.26 (dd, J=10.0 Hz, 3.2 Hz, 1H), 3.92-3.86 (m, 4H), 3.51 (m, 1H), 3.37 (m, 2H), 2.26 (m, 1H), 1.98 (m, 1H), 1.77 (m, 2H).
$^{19}$F NMR (376 MHz, CDCl$_3$, ppm): −126.68 (d, J=10.9 Hz, 1 F).
MS m/z (ESI): 473.9.

Example 9

3-(1-methyl-1H-pyrazol-4-yl)-6-((6-(1-methyl-1H-pyrazol-4-yl)-[1,2,4]triazolo[4,3-a]pyridin-3-yl)thio)-4-(2,2,2-trifluoroethoxy)quinoline (9)

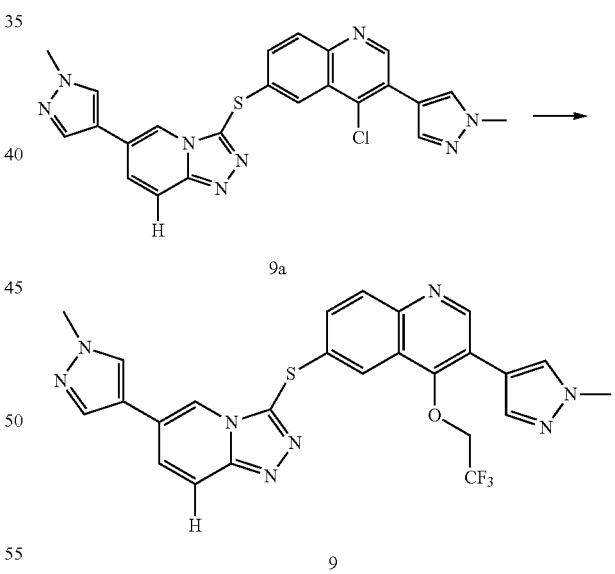

Under $N_2$, to a 25 mL one-necked flask, trifluoroethanol (4.2 mg, 0.042 mmol), dimethyl sulfoxide (1 mL) and sodium tert-butoxide (5.1 mg, 0.053 mmol) were added, and the reaction mixture was stirred at room temperature for 15 minutes, then 4-chloro-3-(1-methyl-1H-pyrazol-4-yl)-6-((6-(1-methyl-1H-pyrazol-4-yl)-[1,2,4]triazolo[4,3-a]pyridin-3-yl)thio)quinoline (10 mg, 0.021 mmol) was added, and the reaction mixture was stirred at room temperature for 1 hour. After LC-MS showed completion of the reaction, the resulting residue was purified by reverse phase column chromatography (40% acetonitrile in water) to give 3-(1-methyl-1H-pyrazol-4-yl)-6-((6-(1-methyl-1H-pyrazol-4-yl)-[1,2,4]triazolo[4,3-a]pyridin-3-yl)thio)-4-(2,2,2-trifluoroethoxy)quinolone 9 (9.6 mg, yield 85%) as a white solid.

MS m/z (ESI): 536.9

$^1$H NMR (400 MHz, CDCl$_3$, ppm): δ 8.92 (s, 1H), 8.20 (s, 1H), 8.01 (d, J=8.8 Hz, 1H), 7.89 (m, 3H), 7.83 (s, 1H), 7.68 (s, 1H), 7.61 (s, 1H), 7.56 (d, J=8.8 Hz, 1H), 7.50 (d, J=9.6 Hz, 1H), 4.09 (q, J=8.1 Hz, 2H), 4.01 (s, 3H), 3.93 (s, 3H).

$^{19}$F NMR (376 MHz, DMSO-d$_6$, ppm): −74.10 (t, J=8.1 Hz, 3 F).

Example 10

4-isopropoxy-3-(1-methyl-1H-pyrazol-4-yl)-6-((6-(1-methyl-1H-pyrazol-4-yl)-[1,2,4]-triazolo[4,3-a]pyridin-3-yl)thio)quinoline (10)

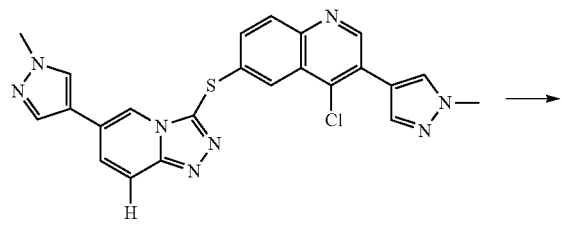

9a

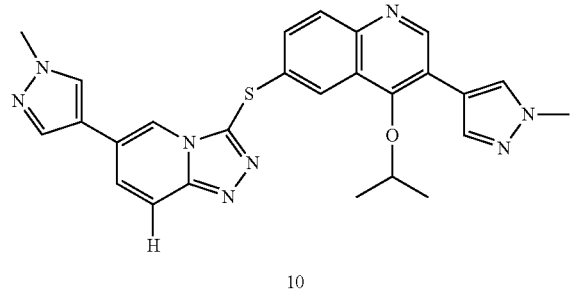

10

Under N$_2$, to a 25 mL one-necked flask, isopropyl alcohol (5.1 mg, 0.053 mmol), dimethyl sulfoxide (1 mL) and sodium tert-butoxide (2.5 mg, 0.042 mmol) were added, and the reaction mixture was stirred at room temperature for 15 minutes, then 4-chloro-3-(1-methyl-1H-pyrazol-4-yl)-6-((6-(1-methyl-1H-pyrazol-4-yl)-[1,2,4]triazolo[4,3-a]pyridin-3-yl)thio)quinoline (10 mg, 0.021 mmol) was added, and the reaction mixture was stirred at room temperature overnight. After LC-MS showed completion of the reaction, the resulting residue was purified by reverse phase column chromatography (40% acetonitrile in water) to give 4-isopropoxy-3-(1-methyl-1H-pyrazol-4-yl)-6-((6-(1-methyl-1H-pyrazol-4-yl)-[1,2,4]triazolo[4,3-a]pyridin-3-yl)thio)quinoline 10 (2.2 mg, yield 21%) as a white solid.

MS m/z (ESI): 496.9.

$^1$H NMR (400 MHz, CDCl$_3$, ppm): δ 8.88 (s, 1H), 8.20 (s, 1H), 8.01 (d, J=8.8 Hz, 1H), 7.91 (m, 3H), 7.81 (s, 1H), 7.67 (s, 1H), 7.59 (s, 1H), 7.54 (dd, J=8.8 Hz, 2.0 Hz, 1 H), 7.49 (dd, J=9.6 Hz, 1.6 Hz, 1H), 4.32 (m, 1H), 3.99 (s, 3H), 3.94 (s, 3H), 1.10 (d, J=6.0 Hz, 6H).

Example 11

4-(4-methoxy-6-((6-(1-methyl-1H-pyrazol-4-yl)-[1,2,4]triazolo[4,3-a]pyridin-3-yl)thio)quinolin-3-yl)morpholin-3-one (11)

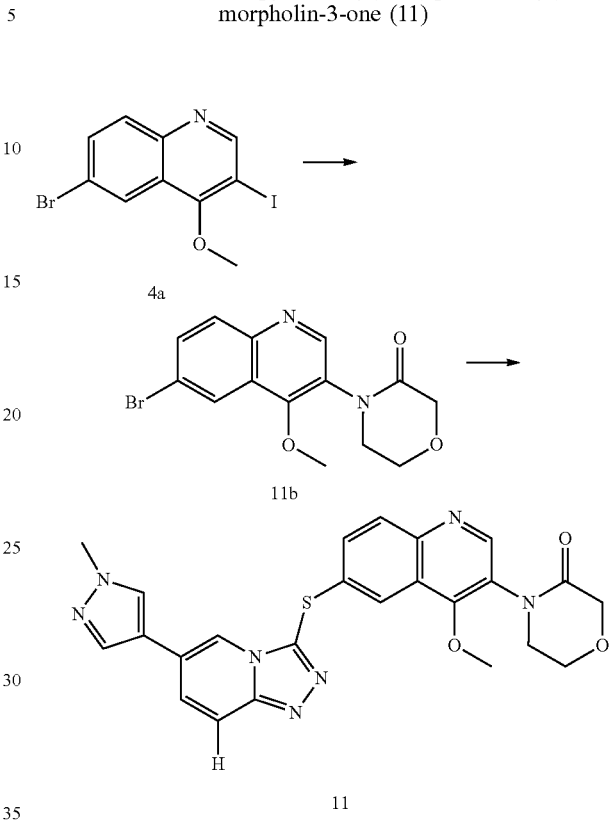

Step 1:
4-(6-bromo-4-methoxyquinolin-3-yl)morpholin-3-one

To a 25 mL one-necked flask, 6-bromo-3-iodo-4-methoxyquinoline (0.2 g, 0.55 mmol), morpholin-3-one (0.083 g, 0.83 mmol), cuprous iodide (0.052 g, 0.28 mmol), potassium phosphate (0.18 g, 0.83 mmol) and dimethyl sulfoxide (3 mL) were added. The reaction mixture was purged with N$_2$ three times, and then N,N'-dimethylethylenediamine (48 mg, 0.55 mmol) was added. The reaction mixture was heated to 50° C. overnight. After removing from heat, the reaction mixture was diluted with ethyl acetate (100 mL), washed with saturated sodium chloride aqueous solution three times, and the organic phase was dried over anhydrous sodium sulfate and concentrated. The resulting residue was purified by silica gel column chromatography (dichloromethane: methanol=20:1) to give 4-(6-bromo-4-methoxyquinolin-3-yl)morpholin-3-one (0.17 g, yield 91%) as a yellow solid.

MS m/z (ESI): 336.9

Step 2: 4-(4-methoxy-6-((6-(1-methyl-1H-pyrazol-4-yl)-[1,2,4]triazolo[4,3-a]pyridin-3-yl)thio)quinolin-3-yl)morpholin-3-one 11

To a 25 mL one-necked flask, 6-(1-methyl-1H-pyrazol-4-yl)-[1,2,4]triazolo[4,3-a]pyridin-3-thiol (127 mg, 0.55 mmol), 4-(6-bromo-4-methoxyquinolin-3-yl)morpholin-3-one (169 mg, 0.50 mmol), tris(dibenzylideneacetone)dipalladium (46 mg, 0.05 mmol), 4,5-bis(diphenylphosphino)-9, 9-dimethylxanthene (58 mg, 0.1 mmol) and anhydrous N,N-dimethylformamide (10 mL) were added. The reaction mixture was purged with N₂ and then stirred for 5 minutes at room temperature until the solids were dissolved. Sodium tert-butoxide (60 mg, 0.0.63 mmol) was added, and the reaction mixture was stirred at room temperature for 5 minutes, then heated to 100° C. overnight. After LC-MS showed completion of the reaction, N,N-dimethylformamide was removed by rotary evaporation. The residue was dissolved in dichloromethane, washed with water twice and concentrated. The resulting residue was purified by reverse phase column chromatography to obtain 4-(4-methoxy-6-((6-(1-methyl-1H-pyrazol-4-yl)-[1,2,4]triazolo[4,3-a]pyridin-3-yl)thio)quinolin-3-yl)morpholin-3-one 11 (4.6 mg) as a white solid.

MS m/z (ESI): 487.9

¹H NMR (400 MHz, CDCl₃, ppm): δ 8.54 (s, 1H), 8.12 (s, 1H), 8.01 (d, J=2.0 Hz, 1H), 7.91 (d, J=8.8 Hz, 1H), 7.82 (d, J=9.6 Hz, 1H), 7.63 (s, 1H), 7.54 (s, 1H), 7.50 (dd, J=8.8 Hz, 2.0 Hz, 1H), 7.43 (dd, J=9.6 Hz, 1.6 Hz, 1H), 4.34 (s, 2H), 4.03 (t, J=5.2 Hz, 2H), 3.96 (s, 3H), 3.88 (s, 3H), 3.68 (t, J=5.0 Hz, 2H).

Example 12

4-(cyclopropylmethoxy)-3-(1-methyl-1H-pyrazol-4-yl)-6-((6-(1-methyl-1H-pyrazol-4-yl)-[1,2,4]triazolo[4,3-a]pyridin-3-yl)thio)quinoline (12)

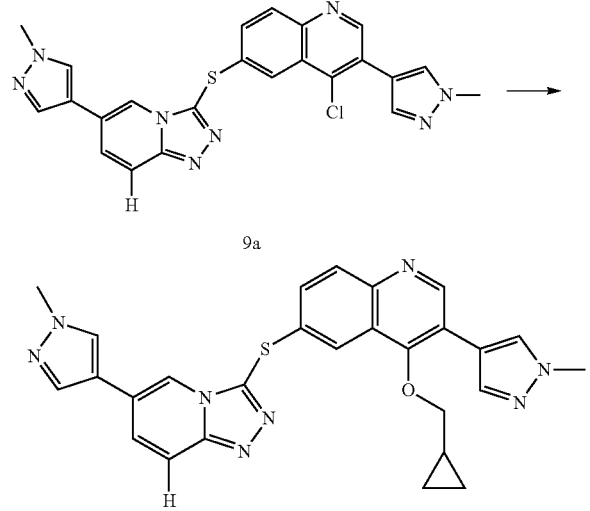

Under N₂, to a 25 mL one-necked flask, isopropyl alcohol (3.0 mg, 0.042 mmol), dimethyl sulfoxide (1 mL) and sodium tert-butoxide (5.1 mg, 0.053 mmol) were added, the reaction mixture was stirred at room temperature for 15 minutes, then 4-chloro-3-(1-methyl-1H-pyrazol-4-yl)-6-((6-(1-methyl-1H-pyrazol-4-yl)-[1,2,4]triazolo[4,3-a]pyridin-3-yl)thio)quinoline (10 mg, 0.021 mmol) was added, and the reaction solution was stirred at room temperature overnight. After LC-MS showed completion of the reaction, the resulting residue was purified by reverse phase column chromatography (30% acetonitrile in water) to give 4-(cyclopropylmethoxy)-3-(1-methyl-1H-pyrazol-4-yl)-6-((6-(1-methyl-1H-pyrazol-4-yl)-[1,2,4]triazolo[4,3-a]pyridin-3-yl)thio)quinoline 12 (4.6 mg, yield 43%).

MS m/z (ESI): 508.9.

¹H NMR (400 MHz, CDCl₃, ppm): δ 8.94 (s, 1H), 8.20 (s, 1H), 8.07 (d, J=8.8 Hz, 1H), 7.96-7.89 (m, 4H), 7.68 (s, 1H), 7.61 (s, 1H), 7.56 (d, J=8.8 Hz, 1H), 7.50 (d, J=9.6 Hz, 1H), 4.00 (s, 3H), 3.94 (s, 3H), 3.67 (d, J=7.2 Hz, 2H), 1.07 (m, 1H), 0.52 (m, 2H), 0.12 (m, 2H).

Example 13

9-((8-(difluoromethoxy)-6-(1-methyl-1H-pyrazol-4-yl)-[1,2,4]triazolo[4,3-a]pyridin-3-yl)thio)-4-methyl-2H-[1,4]oxazino[3,2-c]quinolin-3(4H)-one (13)

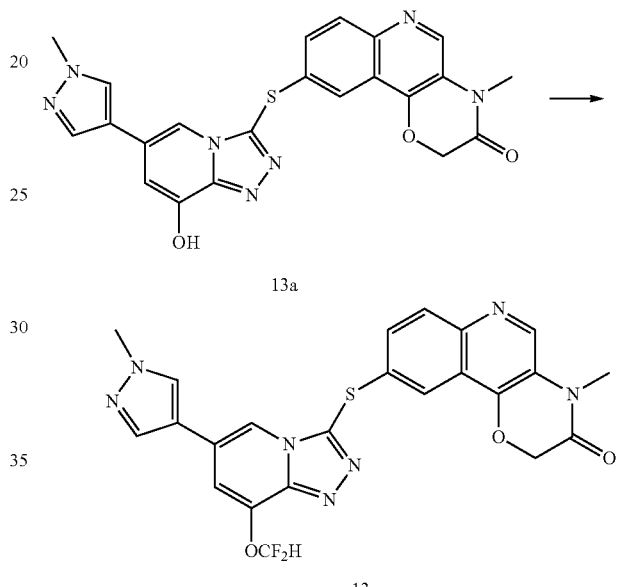

Under N₂, to a 25 mL one-necked flask, 9-((8-hydroxy-6-(1-methyl-1H-pyrazol-4-yl)-[1,2,4]triazolo[4,3-a]pyridin-3-yl)thio)-4-methyl-2H-[1,4]oxazino[3,2-c]quinoline-3 (4H)-one (41 mg, 0.09 mmol), potassium carbonate (25 mg, 0.18 mmol), ethyl chlorodifluoroacetate (16 mg, 0.098 mmol) and anhydrous N,N-dimethylformamide (3 mL) were added. The reaction mixture was stirred for 5 minutes at room temperature, then heated to 70° C. overnight. After LC-MS showed completion of the reaction, N,N-dimethylformamide was removed by rotary evaporation, the resulting residue was dissolved in dichloromethane, washed with water twice and concentrated. The resulting residue was purified by column chromatography (dichloromethane:methanol=20:1) to give 9-((8-(difluoromethoxy)-6-(1-methyl-1H-pyrazol-4-yl)-[1,2,4]triazolo[4,3-a]pyridin-3-yl)thio)-4-methyl-2H-[1,4]oxazino[3,2-c]quinolin-3(4H)-one 12 (3.5 mg) as a white solid.

MS m/z (ESI): 509.8

¹H NMR (400 MHz, CDCl₃, ppm): δ 8.58 (s, 1H), 8.02 (s, 1H), 8.00 (d, J=2.0 Hz, 1H), 7.87 (d, J=8.8 Hz, 1H), 7.50 (t, J=73.4 Hz, 1H), 7.60 (s, 1H), 7.56 (s, 1H), 7.44 (dd, J=8.8 Hz, 2.0 Hz, 1H), 7.15 (s, 1H), 4.82 (s, 2H), 3.88 (s, 3H), 3.44 (s, 3H).

¹⁹F NMR (376 MHz, CDCl₃, ppm): −83.39 (t, J=73.3 Hz, 2 F).

Example 14

10-((8-fluoro-6-(1-methyl-1H-pyrazol-4-yl)-[1,2,4]triazolo[4,3-a]pyridin-3-yl)thio)-3,4-dihydro-2H-[1,4]dioxepino[2,3-c]quinoline (14)

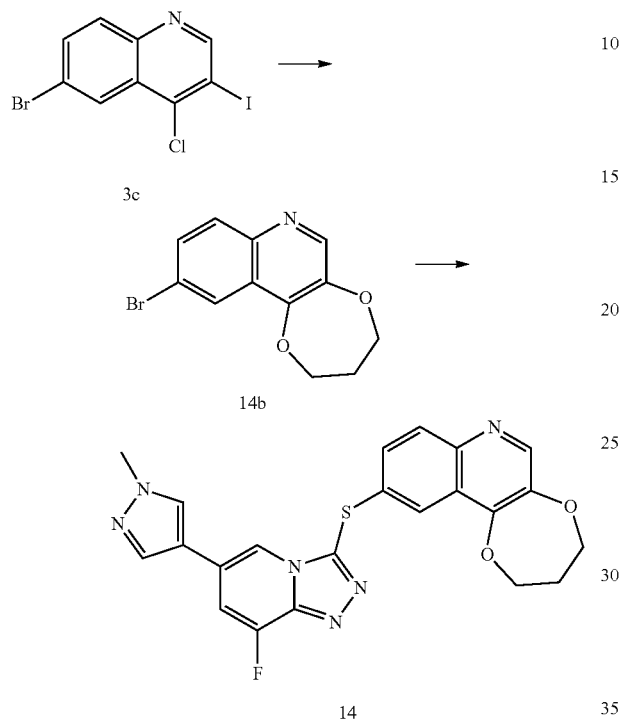

Step 1: 10-bromo-3,4-dihydro-2H-[1,4]dioxepino[2,3-c]quinoline

To a 100 mL sealed tube, 6-bromo-4-chloro-3-iodo-quinoline (1.5 g, 4.07 mmol), cesium carbonate (3.98 g, 12.21 mmol), cuprous iodide (388 mg, 2.0 mmol) and 1,3-propanediol (50 mL) were added. The reaction solution was heated to 100° C. overnight. After LC-MS showed completion of the reaction, the reaction solution was cooled to room temperature, poured into ice water, and extracted with dichloromethane. The organic phases were combined, washed with saturated sodium chloride aqueous solution three times, and dried over potassium carbonate. The resulting residue was purified by silica gel column chromatography (dichloromethane: methanol=20:1) to give 10-bromo-3,4-dihydro-2H-[1,4]dioxepino[2,3-c]quinoline (200 mg, yield 18%) as a white solid.

MS m/z (ESI): 279.8

Step 2: 10-((8-fluoro-6-(1-methyl-1H-pyrazol-4-yl)-[1,2,4]triazolo[4,3-a]pyridine-3-yl)thio)-3,4-dihydro-2H-[1,4]dioxepino[2,3-c]quinoline 14

To a 25 mL one-necked flask, 8-fluoro-6-(1-methyl-1H-pyrazol-4-yl)-[1,2,4]triazolo[4,3-a]pyridin-3-thiol 1 (112 mg, 0.45 mmol) 10-bromo-3,4-dihydro-2H-[1,4]dioxepino[2,3-c]quinoline (100 mg, 0.41 mmol), tris(dibenzylideneacetone)dipalladium (46 mg, 0.05 mmol), 4,5-bis(diphenylphosphino)-9,9-dimethylxanthene (47 mg, 0.08 mmol) and anhydrous N,N-dimethylformamide (5 mL) were added. The reaction mixture was purged with $N_2$ and stirred for 5 minutes at room temperature until the solids were dissolved. Sodium tert-butoxide (52 mg, 0.54 mmol) was added, and the reaction mixture was stirred at room temperature for another 5 minutes, then heated to 100° C. overnight. After LC-MS showed completion of the reaction, N,N-dimethylformamide was removed by rotary evaporation, the resulting residue was dissolved in dichloromethane, washed with water twice and concentrated. The resulting residue was purified by column chromatography to obtain 10-((8-fluoro-6-(1-methyl-1H-pyrazol-4-yl)-[1,2,4]triazolo[4,3-a]pyridin-3-yl)thio)-3,4-dihydro-2H-[1,4]dioxepino[2,3-c]quinoline 14 (61 mg, yield 33%) as a white solid.

MS m/z (ESI): 448.9

$^1$H NMR (400 MHz, CDCl$_3$, ppm): δ 8.55 (s, 1H), 8.15 (s, 1H), 8.06 (s, 1H), 7.87 (d, J=8.8 Hz, 1H), 7.65 (d, J=12.0 Hz, 2H), 7.43 (d, J=8.8 Hz, 1H), 7.16 (d, J=10.4 Hz, 1H), 4.53 (t, J=5.4 Hz, 2H), 4.37 (t, J=5.8 Hz, 2H), 3.95 (s, 3H), 2.35 (m, 2H).

$^{19}$F NMR (376 MHz, CDCl3, ppm): −126.73 (d, J=10.9 Hz, 1 F).

Example 15 cyclopropyl(9-((6-(1-methyl-1H-pyrazol-4-yl)-[1,2,4]triazolo[4,3-a]pyridin-3-yl)thio)-2,3-dihydro-4H-[1,4]oxazino[3,2-c]quinolin-4-yl)methanone (15)

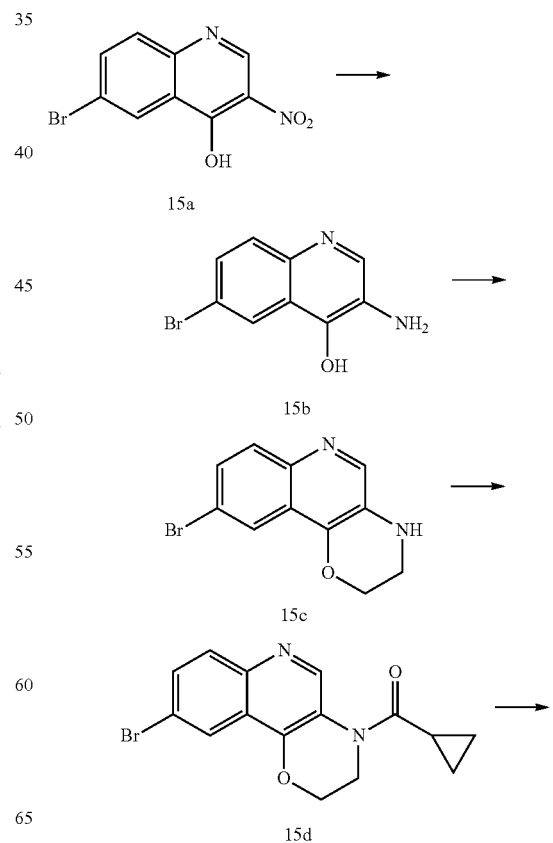

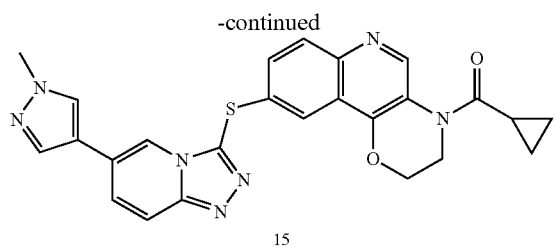

15

Step 1: 3-amino-6-bromoquinolin-4-ol

To a 100 mL one-necked flask, 6-bromo-3-nitro-quinolin-4-ol (2.5 g, 9.0 mmol) and methanol (10 mL) were added, and hydrazine hydrate (2.7 g, 46.5 mmol) was added in an ice bath. Then, a catalytic amount of Raney nickel was added, and the reaction mixture was stirred for 1 hour at room temperature. After TLC showed completion of the reaction, the reaction solution was filtered, and the filter cake was washed with methanol three times. The organic phase was concentrated by rotary evaporation to give 3-amino-6-bromoquinolin-4-ol (2.20 g, yield 95%).

MS m/z (ESI): 238.9

Step 2: 9-bromo-3,4-dihydro-2H-[1,4]oxazino[3,2-c]quinoline

To a 50 mL one-necked flask, 3-amino-6-bromo-quinolin-4-ol (0.26 g, 1.09 mmol), potassium carbonate (0.90 g, 6.54 mmol), 1,2-dibromoethane (0.62 g, 3.27 mmol) and N,N-dimethylformamide (10 mL) were added. The reaction mixture was heated to 80° C. for 4 hours, and then poured into water (200 mL), extracted with ethyl acetate (50 ml, 3 times). The organic phases were combined, dried, and concentrated by rotary evaporation. The resulting residue was purified by silica gel column chromatography (petroleum ether/ethyl acetate=10:1 to 4:1, v/v) to give 9-bromo-3,4-dihydro-2H-[1,4]oxazino[3,2-c]quinoline (102 mg, yield 35%) as a pale yellow solid.

MS m/z (ESI): 264.9

Step 3: (9-bromo-2,3-dihydro-4H-[1,4]oxazino[3,2-c]quinolin-4-yl)(cyclopropyl)methanone To a 25 mL one-necked flask, 9-bromo-3,4-dihydro-2H-[1,4]oxazino[3,2-c]quinoline (76 mg, 0.29 mmol), ethyldiisopropylamine (0.11 ml, 0.57 mmol) and dichloromethane (10 mL) were added. The reaction mixture was stirred for 5 minutes at room temperature, then cyclopropanecarbonyl chloride (30 μL, 0.32 mmol) was added slowly, and the reaction solution was stirred for 3 hours at room temperature. After the reaction was stopped, the solvent was removed by rotary evaporation. The residue was separated by preparative TLC (petroleum ether: ethyl acetate=5:1, v/v) to obtain (9-bromo-2,3-dihydro-4H-[1,4]oxazino[3,2-c]quinolin-4-yl)(cyclopropyl)methanone (57 mg, yield 60%) as a white solid.

MS m/z (ESI): 333.0

Step 4: cyclopropyl(9-((6-(1-methyl-1H-pyrazol-4-yl)-[1,2,4]triazolo[4,3-a]pyridin-3-yl)thio)-2,3-dihydro-4H-[1,4]oxazino[3,2-c]quinolin-4-yl)methanone 15

6-(1-methyl-1H-pyrazol-4-yl)-[1,2,4]thiazole[4,3-a]pyridin-3-thiol (28 mg, 0.12 mmol), (9-bromo-2,3-dihydro-4H-[1,4]oxazino[3,2-c]quinolin-4-yl)(cyclopropyl)methanone (34 mg, 0.10 mmol), tris(dibenzylideneacetone)dipalladium (6.0 mg, 0.011 mmol), 4,5-bis(diphenylphosphino)-9,9-dimethylxanthene (12 mg, 0.022 mmol) and potassium tert-butoxide (23.0 mg, 0.21 mmol) were dissolved in anhydrous N,N-dimethylformamide (10 mL). The reaction solution was headed to 100° C. for 36 hours under N₂. The solvent was removed by rotary evaporation, and the resulting residue was purified by column chromatography (dichloromethane/methanol=20:1, v/v) to give cyclopropyl(9-((6-(1-methyl-1H-pyrazol-4-yl)-[1,2,4]triazolo[4,3-a]pyridin-3-yl)thio)-2,3-dihydro-4H-[1,4]oxazino[3,2-c]quinolin-4-yl)methanone 15 (6 mg, yield 12%) as a pale yellow solid.

MS m/z (ESI): 484.1

¹H NMR (400 MHz, CDCl₃) δ 9.02 (s, 1H), 8.23 (t, J=1.3 Hz, 1H), 8.10 (d, J=2.1 Hz, 1H), 7.93 (dd, J=13.6, 9.1 Hz, 2H), 7.71 (s, 1H), 7.64 (s, 1H), 7.53 (ddd, J=18.4, 9.1, 1.9 Hz, 2H), 4.57 (t, J=4.6 Hz, 2H), 4.13-4.04 (m, 2H), 3.97 (s, 3H), 0.97 (dq, J=7.3, 3.9 Hz, 2H), 0.93-0.82 (m, 3H).

Example 16

4-methyl-9-((6-(1-methyl-1H-pyrazol-4-yl)-[1,2,4]triazolo[4,3-a]pyridin-3-yl)thio)-2H-[1,4]oxazino[3,2-c]quinolin-3(4H)-one (16)

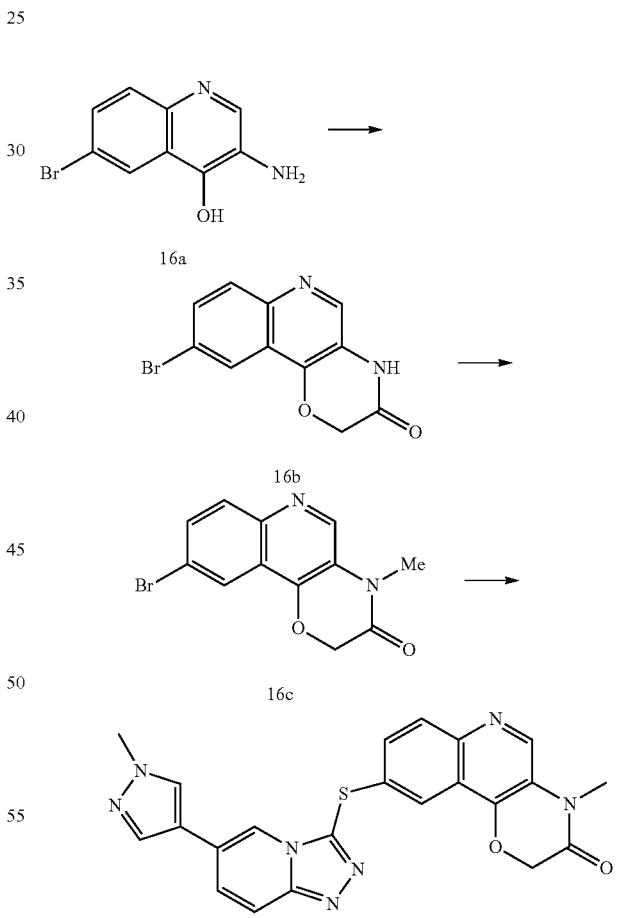

Step 1: 9-bromo-2H-[1,4]oxazino[3,2-c]quinolin-3(4H)-one

To a 50 mL one-necked flask, 3-amino-6-bromo-quinolin-4-ol (300 mg, 1.3 mmol), potassium carbonate (520 mg, 3.8 mmol) and anhydrous N,N-dimethylformamide (7 mL) were added. The reaction mixture was stirred at room temperature for 3 minutes, then chloroacetyl chloride (160 mg, 1.3 mmol) was slowly added. The resulting reaction solution was stirred overnight. After LC-MS showed completion of the reaction, the reaction mixture was poured into ice water, and stirred for 10 minutes. The resulting solid was filtered by a Büchner funnel and washed with water, then dried to give 9-bromo-2H-[1,4]oxazino[3,2-c]quinolin-3(4H)-one (200 mg, yield 57%) as a pale purple solid.

MS m/z (ESI): 278.9

Step 2: 9-bromo-4-methyl-2H-[1,4]oxazino[3,2-c] quinolin-3(4H)-one

To a 100 mL sealed tube, 9-bromo-2H-[1,4]oxazino[3,2-c]quinolin-3(4H)-one (1.0 g, 3.6 mmol), sodium tert-butoxide (516 mg, 5.4 mmol) and anhydrous N,N-dimethylformamide (20 mL) were added. The reaction mixture was stirred for 15 minutes at room temperature, and then methyl iodide (560 mg, 3.9 mmol) was added. A lot of solid was precipitated out of the solution. The reaction mixture was left to stand at room temperature overnight. After LC-MS showed completion of the reaction, an appropriate amount of ethyl acetate, acetone, water and ethanol were added to precipitate the desired product. The resulting solid was filtered to give a pale yellow powder (424 mg), and the filtrate was concentrated and recrystallized to give another yellow powder (268 mg). A total of 692 mg (yield 66%) 9-bromo-4-methyl-2H-[1,4]oxazino[3,2-c]quinolin-3(4H)-one were obtained as a yellow powder.

MS m/z (ESI): 292.9.

Step 3: 4-methyl-9-((6-(1-methyl-1H-pyrazol-4-yl)-[1,2,4]triazolo[4,3-a]pyridin-3-yl)thio)-2H-[1,4]oxazino[3,2-c]quinolin-3(4H)-one 16

To a 25 mL one-necked flask, 6-(1-methyl-1H-pyrazol-4-yl)-[1,2,4]thiazole[4,3-a]pyridin-3-thiol (44 mg, 0.19 mmol), 9-bromo-4-methyl-2H-[1,4]oxazino[3,2-c]quinolin-3(4H)-one (46 mg, 0.157 mmol), tris(dibenzylideneacetone) dipalladium (10 mg, 0.016 mmol), 4,5-bis(diphenylphosphino)-9,9-dimethylxanthene (20 mg, 0.032 mmol) and anhydrous N,N-dimethyl formamide (10 mL) were added. The reaction mixture was purged with $N_2$ and stirred for 5 minutes at room temperature until the solids were dissolved. Sodium tert-butoxide (20 mg, 0.188 mmol) was added and stirred at room temperature for another 5 minutes, then heated at 100° C. for 24 h. After the reaction was stopped, N,N-dimethylformamide was removed by rotary evaporation. The residue was purified by column chromatography (dichloromethane/methanol=25:1, v/v) to obtain 4-methyl-9-((6-(1-methyl-1H-pyrazol-4-yl)-[1,2,4]triazolo[4,3-a] pyridin-3-yl)thio)-2H-[1,4]oxazino[3,2-c]quinolin-3(4H)-one 16 (12 mg, yield 16%) as a pale yellow solid.

MS m/z (ESI): 444.1

$^1$H NMR (400 MHz, CDCl$_3$) δ 8.56 (s, 1H), 8.16-8.12 (m, 1H), 7.94-7.90 (m, 1H), 7.87-7.79 (m, 2H), 7.61 (d, J=0.8 Hz, 1H), 7.56 (d, J=0.9 Hz, 1H), 7.41 (ddd, J=9.0, 2.9, 1.9 Hz, 2H), 7.20 (s, 1H), 4.80 (s, 2H), 3.88 (s, 3H), 3.43 (s, 3H).

Example 17

4-(4-(cyclopropylmethoxy)-6-((6-(1-methyl-1H-pyrazol-4-yl)-[1,2,4]-triazolo[4,3-a]pyridin-3-yl) thio)quinolin-3-yl)morpholine (17)

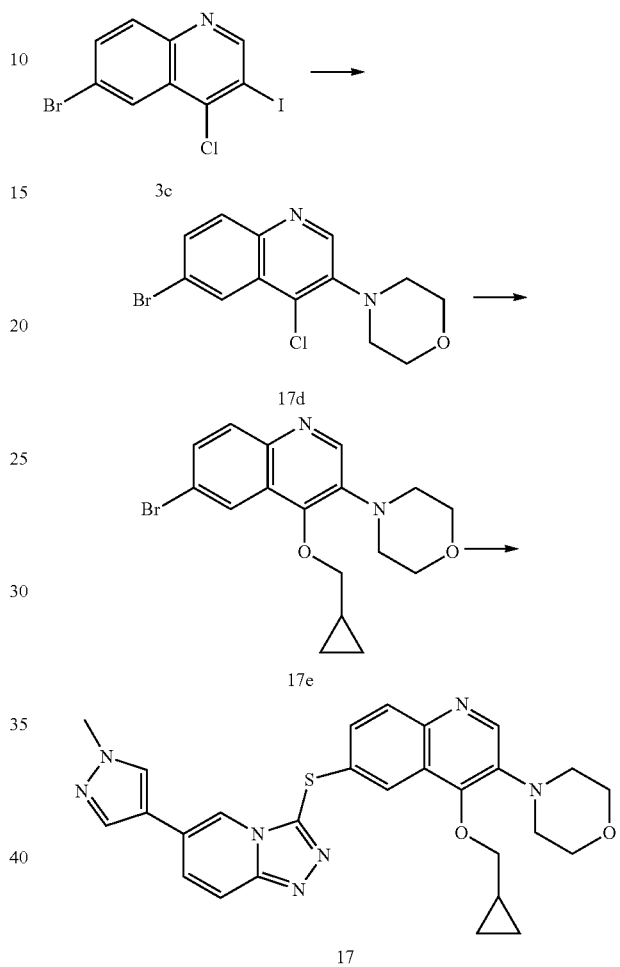

Step 1:
4-(6-bromo-4-chloroquinolin-3-yl)morpholine 6-bromo-4-chloro-3-iodo-quinoline (5.00 g, 13.57 mmol), morpholine (1.42 g, 16.29 mmol), tris(dibenzylideneacetone)dipalladium (1.24 g, 1.36 mmol) and 4,5-bis (diphenylphosphino)-9,9-dimethylxanthene (1.57 g, 2.71 mmol) were dissolved in DMF (90 mL). The reaction solution was heated to 35° C. and stirred for 1 hour under $N_2$, then sodium tert-butoxide (1.56 g, 1.629 mmol) was added. The reaction mixture was stirred for another 16 hours at 35° C., and then the reaction solution was concentrated to dryness under reduced pressure. The resulting residue was dissolved in ethyl acetate, washed with sodium chloride aqueous solution and dried. The solution was filtered and concentrated. The resulting residue was separated by column chromatography (dichloromethane/methanol=100:1, v/v) to give a crude product. The crude product was pulverized and filtered to give 4-(6-bromo-4-chloroquinolin-3-yl)-morpholine (2.5 g, yield 56%) as a white solid.

MS m/z (ESI): 326.9.

Step 2: 4-(6-bromo-4-(cyclopropylmethoxy)quinolin-3-yl)morpholine

To a 25 mL sealed tube, 4-(6-bromo-4-(cyclopropylmethoxy)quinolin-3-yl)-morpholine (100 mg, 0.31 mmol), cyclopropyl methanol (8 mL) and sodium methoxide (81 mg, 1.5 mmol) were added. The reaction solution was heated to 120° C. for 12 hours, and then cooled to room temperature. The excess cyclopropyl methanol was distilled off under reduced pressure. The resulting residue was purified by preparative TLC (petroleum ether: ethyl acetate=5:1) to give 4-(6-bromo-4-(cyclopropylmethoxy)-quinolin-3-yl)-morpholine (65 mg, yield 58%) as a pale yellow solid.

MS m/z (ESI): 363.0.

Step 3: 4-(4-(cyclopropylmethoxy)-6-((6-(1-methyl-1H-pyrazol-4-yl)-[1,2,4]triazolo[4,3-a]pyridin-3-yl)thio)quinolin-3-yl)morpholine (17)

To a 25 mL one-necked flask, 6-(1-methyl-1H-pyrazol-4-yl)-[1,2,4]triazolo[4,3-a]pyridin-3-thiol (42 mg, 0.182 mmol), 4-(6-bromo-4-(cyclopropylmethoxy)quinolin-3-yl)morpholine (60 mg, 0.166 mmol), tris(dibenzylideneacetone)dipalladium (10 mg, 0.017 mmol), 4,5-bis(diphenylphosphino)-9,9-dimethylxanthene (20 mg, 0.034 mmol) and anhydrous N,N-dimethylformamide (10 mL) were added. The reaction mixture was purged with $N_2$ and stirred for 5 minutes at room temperature until the solids were dissolved, then sodium tert-butoxide (24 mg, 0.249 mmol) was added. The reaction solution was stirred at room temperature for another 5 minutes, then heated at 100° C. for 16 hours. After the reaction was stopped, N,N-dimethylformamide was removed by rotary evaporation. The resulting residue was purified by preparative TLC (dichloromethane/methanol=20:1, v/v) to obtain 4-(4-(cyclopropylmethoxy)-6-((6-(1-methyl-1H-pyrazol-4-yl)-[1,2,4]triazolo[4,3-a]pyridin-3-yl)thio)quinolin-3-yl)morpholine 17 (46 mg, yield 49%) as a pale yellow solid.

MS m/z (ESI): 514.2

$^1$H NMR (400 MHz, CDCl$_3$) δ 8.65 (s, 1H), 8.20 (s, 1H), 7.99 (d, J=11.9 Hz, 2H), 7.89 (d, J=9.4 Hz, 1H), 7.67 (s, 1H), 7.60 (s, 1H), 7.47 (t, J=10.7 Hz, 2H), 4.07 (d, J=7.3 Hz, 2H), 3.95 (s, 3H), 3.91-3.84 (m, 4H), 3.26-3.19 (m, 4H), 1.08 (dd, J=10.1, 5.5 Hz, 1H), 0.50 (d, J=7.4 Hz, 2H), 0.17 (d, J=7.0, 6.2 Hz, 2H).

Example 18

9-((6-(1-methyl-1H-pyrazol-4-yl)-[1,2,4]triazolo[4,3-a]pyridin-3-yl)thio)-2H-[1,4]oxazino[3,2-c]quinolin-3(4H)-one (18)

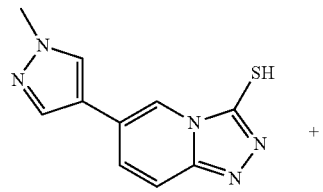

+

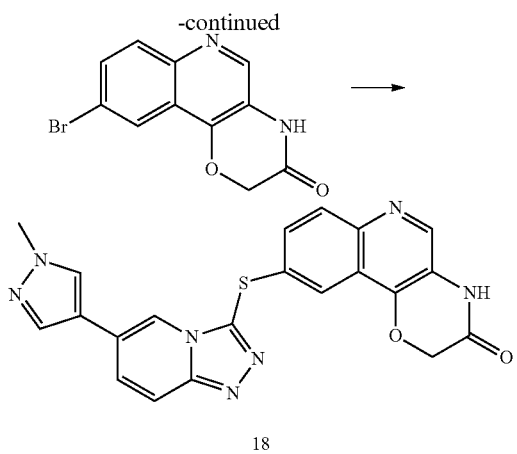

18

To a 25 mL one-necked flask, 6-(1-methyl-1H-pyrazol-4-yl)-[1,2,4]triazolo[4,3-a]pyridin-3-thiol (51 mg, 0.22 mmol), 9-bromine-2H-[1,4]oxazino[3,2-c]quinolin-3(4H)-one (55 mg, 0.2 mmol), tris(dibenzylideneacetone)dipalladium (12 mg, 0.02 mmol), 4,5-bis(diphenylphosphino)-9,9-dimethylxanthene (24 mg, 0.04 mmol) and anhydrous N,N-dimethylformamide (5 mL) were added. The reaction mixture was purged with $N_2$ and stirred for 5 minutes at room temperature until the solids were dissolved. Then, sodium tert-butoxide (39 mg, 0.4 mmol) was added, and the reaction mixture was stirred at room temperature for another 5 minutes and then heated at 100° C. for 16 hours. After the reaction was stopped, N,N-dimethylformamide was removed by rotary evaporation. The resulting residue was purified by column chromatography (dichloromethane/methanol=20:1, v/v) to give 9-((6-(1-methyl-1H-pyrazol-4-yl)-[1,2,4]triazolo[4,3-a]pyridin-3-yl)thio)-2H-[1,4]oxazino[3,2-c]-quinolin-3(4H)-one 18 (34 mg, yield 37%) as a yellow solid.

MS m/z (ESI): 430.1

$^1$H NMR (400 MHz, DMSO-d$_6$) δ 11.09 (d, J=10.6 Hz, 1H), 8.64 (s, 1H), 8.46 (s, 1H), 8.35 (s, 1H), 8.11-7.95 (m, 2H), 7.97-7.76 (m, 3H), 7.47 (dd, J=9.0, 2.1 Hz, 1H), 4.87 (s, 2H), 3.86 (s, 3H).

Example 19

9-((8-fluoro-6-(1-methyl-1H-pyrazol-4-yl)-[1,2,4]triazolo[4,3-a]pyridin-3-yl)thio)-2H-[1,4]oxazino[3,2-c]quinolin-3(4H)-one (19)

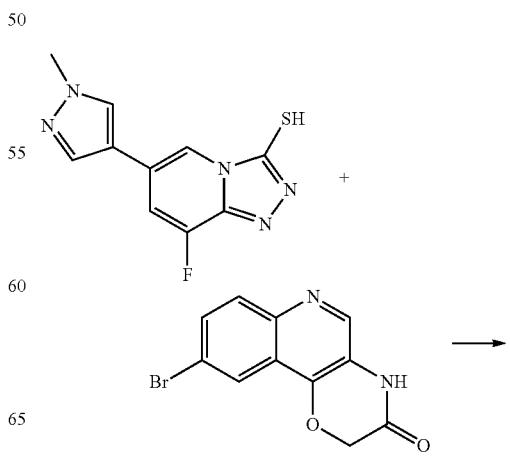

-continued

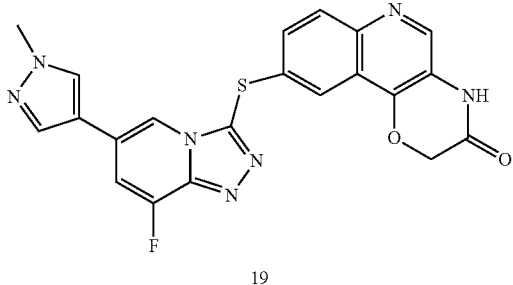

19

To a 30 mL microwave tube, 6-(1-methyl-1H-pyrazol-4-yl)-[1,2,4]triazolo[4,3-a]pyridin-3-thiol (118 mg, 0.516 mmol), 9-bromine-2H-[1,4]oxazino[3,2-c]quinolone-3(4H)-one (120 mg, 0.430 mmol), tris(dibenzylideneacetone)dipalladium (25 mg, 0.043 mmol), 4,5-bis(diphenylphosphino)-9,9-dimethylxanthene (50 mg, 0.086 mmol), sodium t-butoxide (50 mg, 0.516 mmol) and anhydrous N,N-dimethylformamide (5 mL) were added. The reaction mixture was purged with $N_2$ and then heated by microwaves to 120° C. for 4 hours. After the reaction was stopped, N,N-dimethylformamide was removed by rotary evaporation. The resulting residue was purified by reverse phase column chromatography to give 9-((8-fluoro-6-(1-methyl-1H-pyrazol-4-yl)-[1,2,4]triazolo[4,3-a]pyridin-3-yl)thio)-2H-[1,4]oxazino[3,2-c]quinolin-3(4H)-one 19 (6 mg, yield 3%) as a white solid.

MS m/z (ESI): 448.1.
$^1$H NMR (400 MHz, DMSO-$d_6$) δ 11.09 (s, 1H), 8.56 (s, 1H), 8.47 (s, 1H), 8.38 (s, 1H), 8.08 (s, 1H), 7.92 (d, J=2.1 Hz, 1H), 7.86 (dd, J=10.6, 8.2 Hz, 2H), 7.49 (dd, J=9.1, 2.1 Hz, 1H), 4.89 (s, 2H), 3.86 (s, 3H).

Example 20

4-(2-methoxyethyl)-9-((6-(1-methyl-1H-pyrazol-4-yl)-[1,2,4]triazolo[4,3-a]pyridin-3-yl)thio)-2H-[1,4]oxazino[3,2-c]quinolin-3(4H)-one (20)

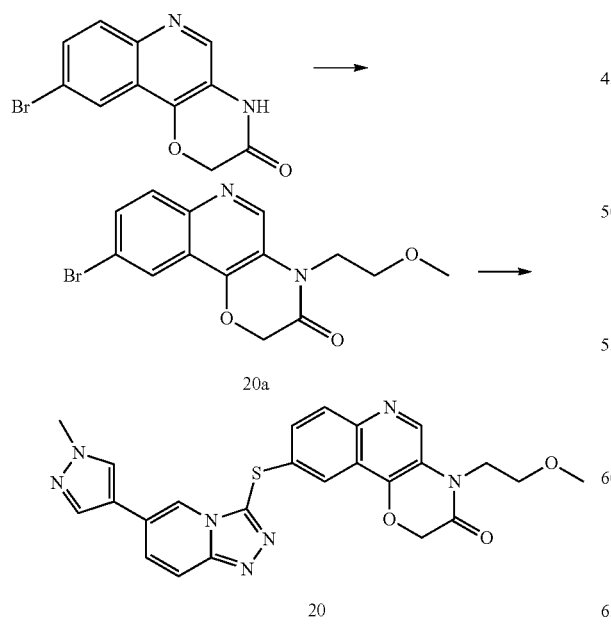

Step 1: 9-bromo-4-(2-methoxyethyl)-2H-[1,4]oxazino[3,2-c]quinolin-3(4H)-one

To a 25 mL one-necked flask, anhydrous N,N-dimethylformamide (5 mL) was added, followed by addition of 9-bromine-2H-[1,4]oxazino[3,2-c]quinoline-3(4H)-one (100 mg, 0.358 mmol) and sodium t-butoxide (50 mg, 0.534 mmol). The reaction mixture was stirred for 15 minutes at room temperature and then 1-bromo-2-methoxy-ethane (65 mg, 0.465 mmol) was added. The reaction solution was stirred for 4 hours at room temperature, N,N-dimethylformamide was removed under reduced pressure. The resulting solid was separated by preparative TLC (petroleum ether: ethyl acetate=7:1) to give 9-bromo-4-(2-methoxyethyl)-2H-[1,4]oxazino[3,2-c]quinolin-3(4H)-one (56 mg, yield 46%).

MS m/z (ESI): 337.0.

Step 2: 4-(2-methoxyethyl)-9-((6-(1-methyl-1H-pyrazol-4-yl)-[1,2,4]triazolo[4,3-a]pyridin-3-yl)thio)-2H-[1,4]oxazino[3,2-c]quinolin-3(4H)-one 20

To a 30 mL microwave tube, 6-(1-methyl-1H-pyrazol-4-yl)-[1,2,4]triazolo[4,3-a]pyridin-3-thio 28d (50 mg, 0.216 mmol), 9-bromo-4-(2-methoxyethyl)-2H-[1,4]oxazino[3,2-c]quinolin-3(4H)-one (56 mg, 0.166 mmol), tris(dibenzylideneacetone)dipalladium (10 mg, 0.017 mmol), 4,5-bis(diphenylphosphino)-9,9-dimethylxanthene (20 mg, 0.034 mmol), sodium tert-butoxide (25 mg, 0.249 mmol) and anhydrous N,N-dimethylformamide (5 mL) were added successively. The reaction mixture was purged with $N_2$ and heated by microwaves to 120° C. for 2.5 hours. After the reaction was stopped, N,N-dimethylformamide was removed by rotary evaporation. The resulting residue was purified by reverse phase column chromatography to give 4-(2-methoxyethyl)-9-((6-(1-methyl-1H-pyrazol-4-yl)-[1,2,4]triazolo[4,3-a]pyridin-3-yl)thio)-2H-[1,4]oxazino[3,2-c]quinolin-3(4H)-one 20 (20 mg, yield 24%) as a white solid.

MS m/z (ESI): 488.1.
$^1$H NMR (400 MHz, DMSO-$d_6$) δ 8.90 (s, 1H), 8.70-8.62 (m, 1H), 8.35 (s, 1H), 8.10-7.98 (m, 2H), 7.95-7.79 (m, 3H), 7.50 (dd, J=9.0, 2.1 Hz, 1H), 4.96 (s, 2H), 4.25 (t, J=5.4 Hz, 2H), 3.86 (s, 3H), 3.57 (t, J=5.4 Hz, 2H), 3.39 (d, J=11.4 Hz, 1H), 3.21 (s, 3H).

Example 21

9-((8-fluoro-6-(1-methyl-1H-pyrazol-4-yl)-[1,2,4]triazolo[4,3-a]pyridin-3-yl)thio)-4-(2-methoxyethyl)-2H-[1,4]oxazino[3,2-c]quinolin-3(4H)-one (21)

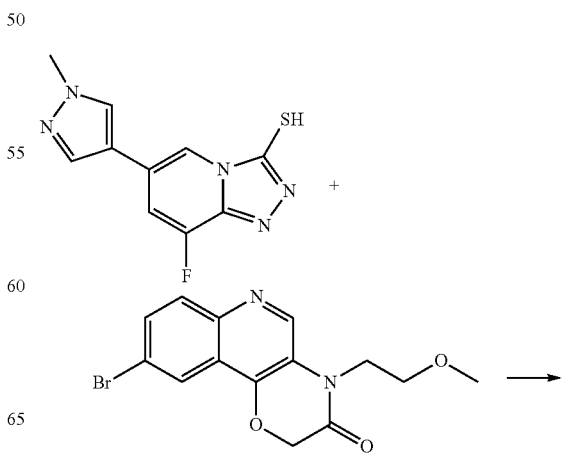

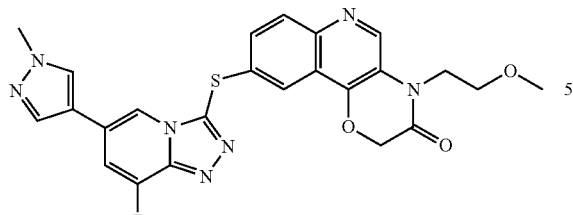

21

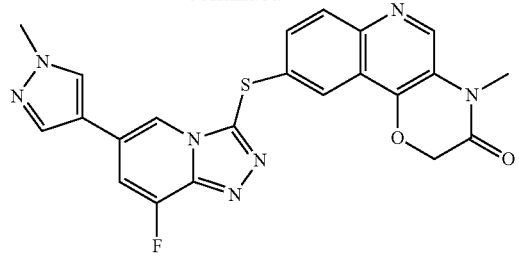

22

To a 30 mL microwave tube, 8-fluoro-6-(1-methyl-1H-pyrazol-4-yl)-[1,2,4]triazolo[4,3-a]pyridin-3-thiol (75 mg, 0.299 mmol), 9-bromo-4-(2-methoxyethyl)-2H-[1,4]oxazino[3,2-c]quinolin-3(4H)-one (84 mg, 0.249 mmol), tris(dibenzylideneacetone)dipalladium (15 mg, 0.025 mmol), 4,5-bis(diphenylphosphino)-9,9-dimethylxanthene (30 mg, 0.05 mmol), sodium tert-butoxide (30 mg, 0.299 mmol) and anhydrous N,N-dimethylformamide (5 mL) were added successively. The reaction mixture was purged with $N_2$ and heated by microwaves to 120° C. for 4 hours. After the reaction was stopped, N,N-dimethylformamide was removed by rotary evaporation. The resulting residue was purified by reverse phase column chromatography to give 9-((8-fluoro-6-(1-methyl-1H-pyrazol-4-yl)-[1,2,4]triazolo[4,3-a]pyridin-3-yl)thio)-4-(2-methoxyethyl)-2H-[1,4]oxazino[3,2-c]quinolin-3(4H)-one 21 (20 mg, yield 15%) as a white solid.

MS m/z (ESI): 506.1.

$^1$H NMR (400 MHz, CDCl$_3$) δ 8.91 (s, 1H), 8.08-7.98 (m, 2H), 7.93 (d, J=8.9 Hz, 1H), 7.67 (s, 1H), 7.61 (s, 1H), 7.50 (dd, J=8.9, 2.1 Hz, 1H), 7.17 (d, J=10.3 Hz, 1H), 4.87 (s, 2H), 4.23 (t, J=5.2 Hz, 2H), 3.95 (s, 3H), 3.70 (t, J=5.2 Hz, 2H), 3.33 (s, 3H).

Example 22

9-((8-fluoro-6-(1-methyl-1H-pyrazol-4-yl)-[1,2,4]triazolo[4,3-a]pyridin-3-yl)thio)-4-methyl-2H-[1,4]oxazino[3,2-c]quinolin-3(4H)-one (22)

To a 30 mL microwave tube, 8-fluoro-6-(1-methyl-1H-pyrazol-4-yl)-[1,2,4]triazolo[4,3-a]pyridin-3-thiol (93 mg, 0.375 mmol), 9-bromo-4-methyl-2H-[1,4]oxazino[3,2-c]quinolin-3(4H)-one (100 mg, 0.341 mmol), tris(dibenzylideneacetone)dipalladium (20 mg, 0.034 mmol), 4,5-bis(diphenylphosphino)-9,9-dimethylxanthene (40 mg, 0.068 mmol), sodium tert-butoxide (40 mg, 0.409 mmol) and anhydrous N,N-dimethylformamide (5 mL) were added successively. The reaction mixture was purged with $N_2$ and heated by microwaves to 120° C. for 4 hours. After the reaction was stopped, N,N-dimethylformamide was removed by rotary evaporation. The residue was purified by reverse phase column chromatography to give 9-((8-fluoro-6-(1-methyl-1H-pyrazol-4-yl)-[1,2,4]triazolo[4,3-a]pyridin-3-yl)thio)-4-methyl-2H-[1,4]oxazino[3,2-c]quinolin-3(4H)-one 22 (36 mg, yield 23%) as a white solid.

MS m/z (ESI): 462.1.

$^1$H NMR (400 M, DMSO-d$_6$, ppm) δ 8.82 (s, 1H), 8.57 (s, 1H), 8.38 (s, 1H), 8.08 (s, 1H), 7.97 (s, 1H), 7.91 (d, J=9.2 Hz, 1H), 7.85 (d, J=12.0 Hz, 1H), 7.52 (d, J=9.6 Hz, 1H), 4.98 (s, 2H), 3.86 (s, 3H), 3.43 (s, 3H).

Example 23

2-cyclopropyl-8-((6-(1-methyl-1H-pyrazol-4-yl)-[1,2,4]triazolo[4,3-a]pyridin-3-yl)thio)thiazolo[4,5-c]quinoline (23)

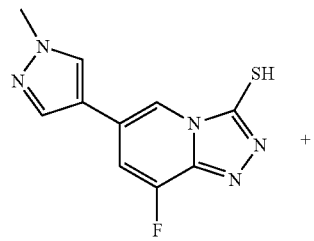 +

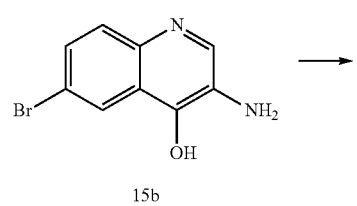

15b

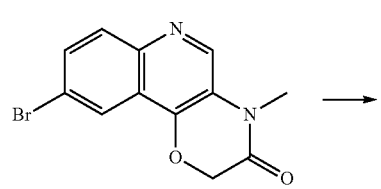 →

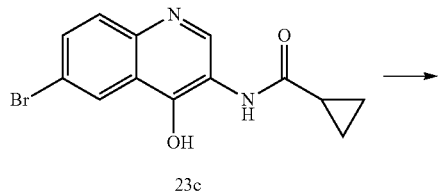 →

23c

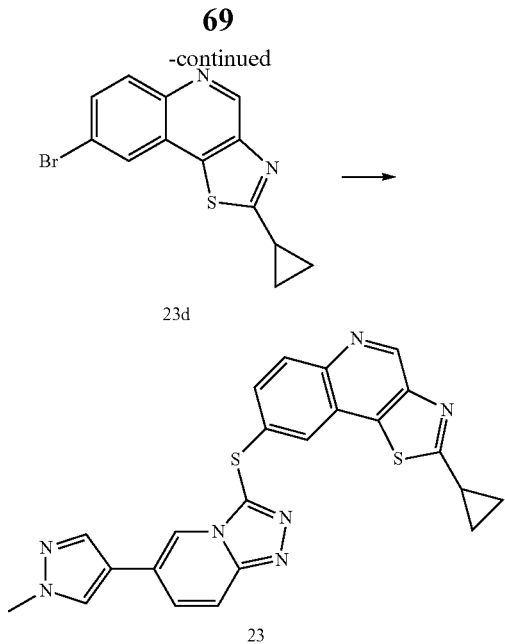

23d

Step 1: N-(6-bromo-4-hydroxyquinolin-3-yl)cyclopropanecarboxamide 23c

To a 50 mL one-necked flask, 3-amino-6-bromoquinolin-4-ol 15b (200 mg, 0.84 mmol), triethylamine (214 mg, 2.1 mmol) and anhydrous dichloromethane (20 mL) were added. The reaction solution was stirred at −30° C., then cyclopropanecarbonyl chloride (79 mg, 0.75 mmol) was added dropwise. The reaction mixture was stirred at −30° C. for 30 minutes, then reacted at room temperature overnight. After LC-MS showed completion of the reaction, the reaction mixture was filtered. The resulting solid was washed with dichloromethane and dried in air to give N-(6-bromo-4-hydroxyquinolin-3-yl)-cyclopropanecarboxamide (100 mg, yield 34%) as a black solid.

MS m/z (ESI): 307, 309.

$^1$H-NMR (DMSO, 400 MHz): δ 12.10 (s, 1H), 9.57 (s, 1H), 8.96 (s, 1H), 8.27 (d, J=2.0 Hz, 1H), 7.77 (dd, J=2.0, 8.8 Hz, 1H), 7.57 (d, J=8.8 Hz, 1H), 2.19-2.26 (m, 1H), 0.76-0.79 (m, 4H).

Step 2: 8-bromo-2-cyclopropylthiazolo[4,5-c]quinoline 23d

To a 50 mL one-necked flask, N-(6-bromo-4-hydroxyquinolin-3-yl)cyclopropanecarboxamide (0.15 g, 0.49 mmol), phosphorus pentasulfide (0.22 g, 0.98 mmol) and anhydrous pyridine (5 mL) were added. The reaction mixture was refluxed for 2 hours. After LC-MS showed completion of the reaction, the solvent was removed by rotary evaporation. The residue was dissolved in ethyl acetate (40 mL), and saturated sodium bicarbonate aqueous solution was added to adjust the pH to 9. The layers were separated. The organic layer was washed successively with saturated sodium bicarbonate aqueous solution and sodium chloride aqueous solution, and then dried and filtered. The solvent was removed by rotary evaporation, and the resulting residue was purified by preparative TLC (petroleum ether: ethyl acetate=3:1) to give 8-bromo-2-cyclopropylthiazolo[4,5-c]quinoline (90 mg, yield 60%) as a white solid.

MS m/z (ESI): 305, 307.

$^1$H-NMR (CDCl$_3$, 400 MHz): δ 9.23 (s, 1H), 8.00-8.02 (m, 2H), 7.70 (dd, J=2.0, 8.8 Hz, 1H), 2.47-2.54 (m, 1H), 1.34-1.36 (m, 4H).

Step 3: 2-cyclopropyl-8-((6-(1-methyl-1H-pyrazol-4-yl)-[1,2,4]triazolo[4,3-a]pyridin-3-yl)thio)thiazolo[4,5-c]quinoline 23

To a 100 mL three-necked flask, 8-bromo-2-cyclopropylthiazolo[4,5-c]quinoline (0.04 g, 0.13 mmol), 6-(1-methyl-1H-pyrazol-4-yl)-[1,2,4]thiazole[4,3-a]pyridin-3-thiol (0.03 g, 0.13 mmol), tris(dibenzylideneacetone)dipalladium (0.024 g, 0.026 mmol), 4,5-bis(diphenylphosphino)-9,9-dimethylxanthene (0.015 g, 0.026 mmol), sodium tert-butoxide (0.016 g, 0.17 mmol) and anhydrous N,N-dimethylformamide (4 mL) were added. The reaction mixture was purged with N$_2$ three times, then heated to 100° C. overnight. After LC-MS showed completion of the reaction, the reaction mixture was filtered by celite, and washed with ethyl acetate (30 mL). The organic phase was washed with sodium chloride aqueous solution, dried and filtered. The solvent was removed by rotary evaporation, and the crude product was purified by reverse phase column chromatography to give 2-cyclopropyl-8-((6-(1-methyl-1H-pyrazol-4-yl)-[1,2,4]triazolo[4,3-a]pyridin-3-yl)thio)thiazolo[4,5-c]quinoline 23 (15 mg, yield 25%) as a pale yellow solid.

MS m/z (ESI): 456;

$^1$H-NMR (CDCl$_3$, 400 MHz): δ 9.31 (s, 1H), 8.23 (s, 1H), 8.17 (d, J=8.8 Hz, 1H), 7.88-7.91 (m, 2H), 7.69 (s, 1H), 7.60 (s, 1H), 7.56 (dd, J=1.6, 8.8 Hz, 1H), 7.49 (dd, J=1.6, 8.8 Hz, 1H), 3.94 (s, 3H), 2.45-2.51 (m, 1H), 1.31-1.35 (m, 4H).

Example 24

2-cyclopropyl-8-((8-fluoro-6-(1-methyl-1H-pyrazol-4-yl)-[1,2,4]triazolo[4,3-a]pyridin-3-yl)thio)thiazolo[4,5-c]quinolone (24)

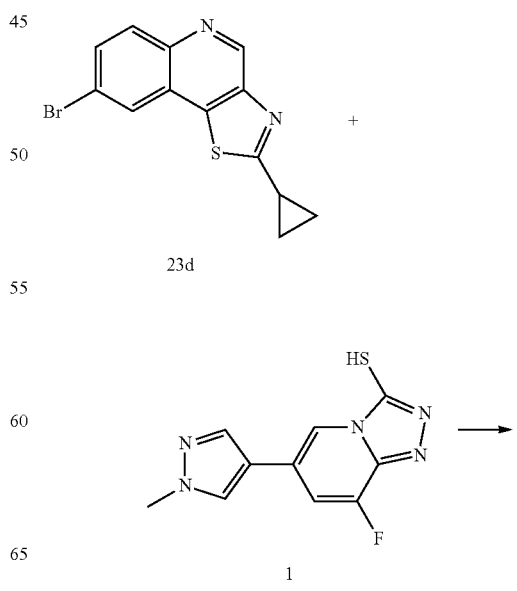

1

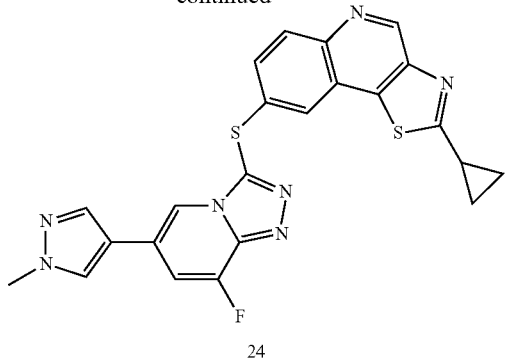

24

To a 100 mL three-necked flask, 8-bromo-2-cyclopropylthiazolo[4,5-c]quinoline (0.055 g, 0.18 mmol), 8-fluoro-6-(1-methyl-1H-pyrazol-4-yl)-[1,2,4]triazolo[4,3-a]pyridin-3-thiol (0.05 g, 0.20 mmol), tris(dibenzylideneacetone) dipalladium (0.016 g, 0.018 mmol), 4,5-bis(diphenylphosphino)-9,9-dimethylxanthene (0.021 g, 0.036 mmol), sodium tert-butoxide (0.021 g, 0.22 mmol) and anhydrous N,N-dimethylformamide (5 mL) were added. The reaction mixture was purged with $N_2$ three times and heated to 100° C. for 4 hours. After LC-MS showed completion of the reaction, the reaction mixture was filtered by celite, and washed with ethyl acetate (30 mL). The organic layer was washed with sodium chloride aqueous solution, dried and filtered. The solvent was removed by rotary evaporation, and the crude product was purified by reverse phase column chromatography to give 2-cyclopropyl-8-((8-fluoro-6-(1-methyl-1H-pyrazol-4-yl)-[1,2,4]triazolo[4,3-a]pyridin-3-yl)thio)-thiazolo[4,5-c]quinoline (10 mg, yield 12%) as a white solid.

MS m/z (ESI): 474;

$^1$H-NMR (CDCl$_3$, 400 MHz): δ 9.32 (s, 1H), 8.13 (d, J=8.8 Hz, 1H), 8.08 (s, 1H), 7.91 (s, 1H), 7.67 (s, 1H), 7.60 (s, 1H), 7.57 (d, J=8.8 Hz, 1H), 7.18 (d, J=10.4 Hz, 1H), 3.95 (s, 3H), 2.46-2.51 (m, 1H), 1.31-1.35 (m, 4H).

Example 25

3-methyl-8-((6-(1-methyl-1H-pyrazol-4-yl)-[1,2,4]triazolo[4,3-a]pyridin-3-yl)thio)oxazolo[4,5-c]quinolin-2(3H)-one (25)

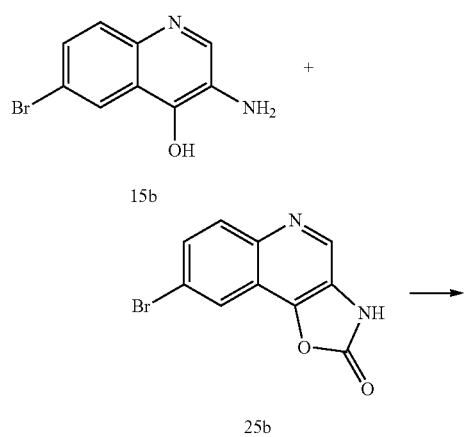

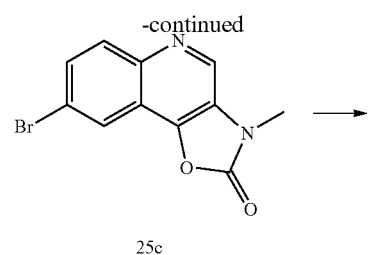

25c

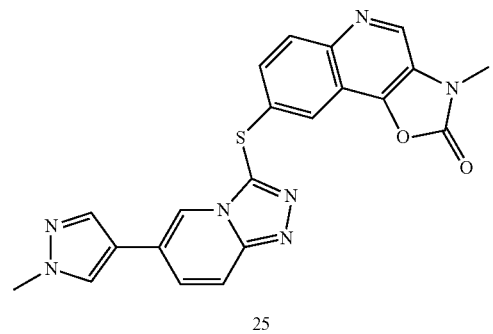

25

Step 1: 8-bromooxazolo[4,5-c]quinolin-2(3H)-one 25b

To a 50 mL one-necked flask, 3-amino-6-bromoquinolin-4-ol (0.5 g, 2.09 mmol), N,N'-carbonyldiimidazole (0.51 g, 3.14 mmol) and tetrahydrofuran (20 mL) were added. The reaction mixture was heated to reflux for 4 hours under $N_2$. The solvent was removed by rotary evaporation. The resulting residue was mixed with ethyl acetate (30 mL) and 2M diluted hydrochloric acid (15 mL), and then filtered. The resulting solid was dried in air to give 8-bromooxazolo[4,5-c]quinolin-2(3H)-one (0.4 g, yield 72%) as a pale yellow solid.

MS m/z (ESI): 265, 267.

Step 2: 8-bromo-3-methyloxazolo[4,5-c]quinolin-2(3H)-one 25c

To a 50 mL three-necked flask, 8-bromooxazolo[4,5-c]quinolin-2(3H)-one (0.10 g, 0.28 mmol) and anhydrous N,N-dimethylformamide (2 mL) were added. The reaction mixture was stirred under $N_2$ in an ice bath, and then sodium hydride (60% in mineral oil, 0.023 g, 0.57 mmol) was added. The reaction solution was stirred for half an hour, then iodomethane (0.081 g, 0.57 mmol) was added. The reaction solution was stirred for another 2 hours at room temperature under $N_2$. After LC-MS showed completion of the reaction, ethyl acetate (40 mL) was added, and the reaction mixture was filtered. The filtrate was washed with sodium chloride aqueous solution, and then dried over anhydrous sodium sulfate and filtered. The solvent was removed by rotary evaporation, and the crude product was purified by preparative TLC (petroleum ether/ethyl acetate=1/1) to give 8-bromo-3-methyloxazolo[4,5-c]quinolin-2(3H)-one (50 mg, yield 48%) as a pale yellow solid.

MS m/z (ESI): 279, 281.

$^1$H-NMR (CDCl$_3$, 400 MHz): δ 8.75 (s, 1H), 8.20 (s, 1H), 8.00 (d, J=8.8 Hz, 1H), 7.74 (d, J=8.8 Hz, 1H), 3.61 (s, 1H).

Step 3: 3-methyl-8-((6-(1-methyl-1H-pyrazol-4-yl)-[1,2,4]triazolo[4,3-a]pyridin-3-yl)thio)oxazolo[4,5-c]quinolin-2(3H)-one (25)

To a 10 mL three-necked flask, 6-(1-methyl-1H-pyrazol-4-yl)-[1,2,4]triazolo[4,3-a]pyridin-3-thiol (0.041 g, 0.18 mmol), 8-bromo-3-methyloxazolo[4,5-c]quinolin-2(3H)-one (0.05 g, 0.18 mmol), tris(dibenzylideneacetone)dipalladium (0.016 g, 0.018 mmol), 4,5-bis(diphenylphosphino)-9,9-dimethylxanthene (0.021 g, 0.036 mmol), sodium tert-butoxide (0.026 g, 0.27 mmol) and anhydrous N,N-dimethylformamide (3 mL) were added. The reaction mixture was purged with $N_2$ three times and heated to 100° C. for 2 hours. After LC-MS showed completion of the reaction, the reaction solution was filtered by celite, and washed with ethyl acetate (30 mL). The organic phase was washed with sodium chloride aqueous solution, dried and filtered. The solvent was removed by rotary evaporation, and the crude product was purified by reverse phase column chromatography to give 3-methyl-8-((6-(1-methyl-1H-pyrazol-4-yl)-[1,2,4]triazolo[4,3-a]pyridin-3-yl)thio)oxazolo[4,5-c]quinolin-2(3H)-one 25 (5 mg, yield 7%) as a white solid.

MS m/z (ESI): 430.

$^{1}$H-NMR (CDCl$_3$, 400 MHz): δ 8.69 (s, 1H), 8.22 (s, 1H), 8.02 (d, J=8.8 Hz, 1H), 7.92 (d, J=8.8 Hz, 1H), 7.85 (s, 1H), 7.69 (s, 1H), 7.64 (s, 1H), 7.49-7.53 (m, 2H), 3.95 (s, 3H), 3.57 (s, 3H).

Example 26

4-(difluoromethoxy)-3-(1-methyl-1H-pyrazol-4-yl)-6-((6-(1-methyl-1H-pyrazol-4-yl)-[1,2,4]triazolo[4,3-a]pyridin-3-yl)thio)quinoline (26)

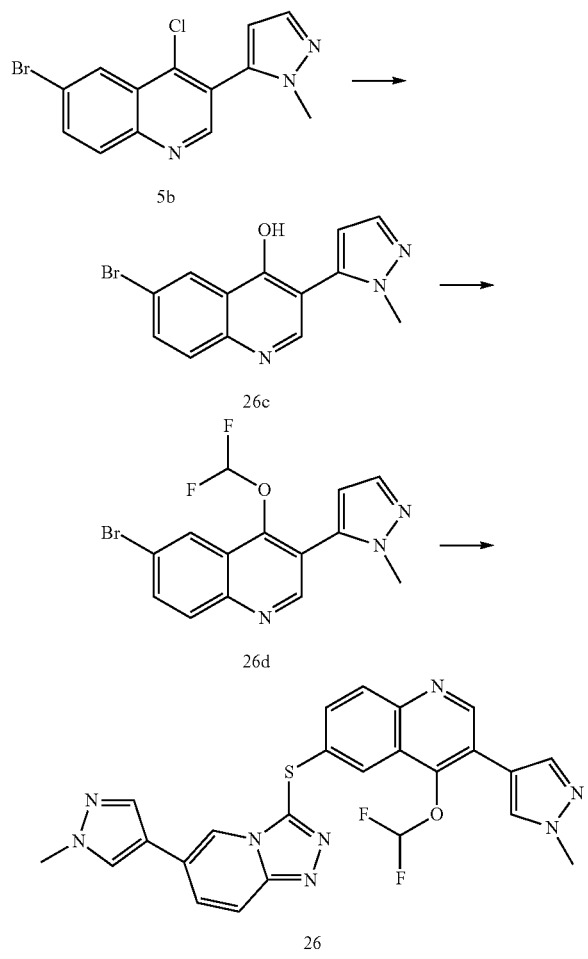

Step 1: 6-bromo-3-(1-methyl-1H-pyrazol-5-yl)quinolin-4-ol 26c

To a 30 mL microwave tube, 6-bromo-4-chloro-3-(1-methyl-1H-pyrazol-5-yl)quinoline (100 mg, 0.31 mmol), potassium hydroxide aqueous solution (2M, 2 mL) and dimethyl sulfoxide (8 mL) were added. The reaction mixture was heated by microwaves to 80° C. for 1 hour, then cooled to room temperature. After LC-MS showed completion of the reaction, the reaction solution was diluted with ethyl acetate, and diluted hydrochloric acid was added to adjust the pH to 6. The layers were separated. The aqueous phase was extracted with ethyl acetate, and the organic phases were combined, dried over anhydrous sodium sulfate, and filtered. The solvent was removed by rotary evaporation, and the crude product was purified by preparative TLC (petroleum ether/ethyl acetate=1/1) to give 6-bromo-3-(1-methyl-1H-pyrazol-5-yl)quinolin-4-ol (50 mg, yield 53%) as a gray solid.

MS m/z (ESI): 304, 306[M+H]$^+$.

Step 2: 6-bromo-4-(difluoromethoxy)-3-(1-methyl-1H-pyrazol-5-yl)quinoline 26d

To a 10 mL microwave tube, 6-bromo-3-(1-methyl-1H-pyrazol-5-yl)quinolin-4-ol (50 mg, 0.16 mmol), potassium hydroxide aqueous solution (2 M, 1 mL) and acetonitrile (3 mL) were added. The reaction mixture was cooled to −20° C., bromodifluoromethyl diethyl phosphate (92 mg, 0.35 mmol) was added, and the reaction mixture was stirred at room temperature overnight. After LC-MS showed completion of the reaction, the solvent was removed by rotary evaporation, and then extracted with ethyl acetate. The organic phases were combined, dried over anhydrous sodium sulfate, and filtered. The solvent was removed by rotary evaporation, and the crude product was purified by preparative TLC (dichloromethane/methanol=25/1) to give 6-bromo-4-(difluoromethoxy)-3-(1-methyl-1H-pyrazol-5-yl)quinoline (15 mg, yield 13%) as a white solid.

MS m/z (ESI): 354, 356[M+H]$^+$.

Step 3: 4-(difluoromethoxy)-3-(1-methyl-1H-pyrazol-4-yl)-6-((6-(1-methyl-1H-pyrazol-4-yl)-[1,2,4]triazolo[4,3-a]pyridin-3-yl)thio)quinoline 26

To a 25 mL three-necked flask, 6-bromo-4-(difluoromethoxy)-3-(1-methyl-1H-pyrazol-5-yl)quinoline (0.015 g, 0.04 mmol), 8-fluoro-6-(1-methyl-1H-pyrazol-4-yl)-[1,2,4]triazolo[4,3-a]pyridin-3-thiol (0.012 g, 0.05 mmol), tri(dibenzenylpropanone)dipalladium (0.004 g, 0.004 mmol), 4,5-bis(diphenylphosphino)-9,9-dimethylxanthene (0.005 g, 0.008 mmol), sodium tert-butoxide (0.005 g, 0.05 mmol) and anhydrous N,N-dimethylformamide (3 mL) were added. The reaction mixture was purged with $N_2$ three times and then heated to 85° C. for 14 hours. After LC-MS showed completion of the reaction, the reaction mixture was filtered by celite, and washed with ethyl acetate (30 mL). The organic phase was washed with sodium chloride aqueous solution, dried and filtered. The solvent was removed by rotary evaporation, and the resulting residue was purified by reverse phase column chromatography to give 4-(difluoromethoxy)-3-(1-methyl-1H-pyrazol-4-yl)-6-((6-(1-methyl-1H-pyrazol-4-yl)-[1,2,4]triazolo[4,3-a]pyridin-3-yl)thio)quinoline 26 (5 mg, yield 24%) as a white solid.

MS m/z (ESI): 505.

$^{1}$H-NMR (CDCl$_3$, 400 MHz): δ 9.03 (s, 1H), 8.21 (s, 1H), 8.03 (m, 2H), 7.95 (s, 1H), 7.90 (m, 2H), 7.68 (s, 1H), 7.61

(s, 1H), 7.57 (d, J=8.8 Hz, 1H), 7.50 (d, J=8.8 Hz, 1H), 6.29 (t, J=7.4 Hz, 1H), 4.02 (s, 3H), 3.94 (s, 3H).

Example 27

N-methyl-N-(1-methyl-6-((6-(1-methyl-1H-pyrazol-4-yl)-[1,2,4]triazolo[4,3-a]pyridin-3-yl)thio)-4-oxo-1,4-dihydroquinolin-3-yl)cyclopropanecarboxamide (27)

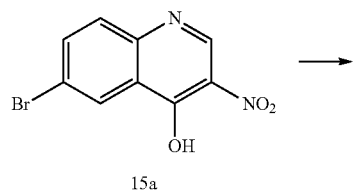

15a

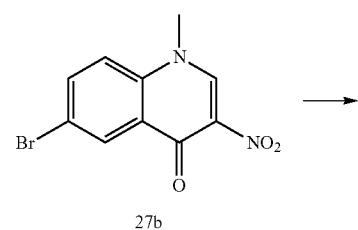

27b

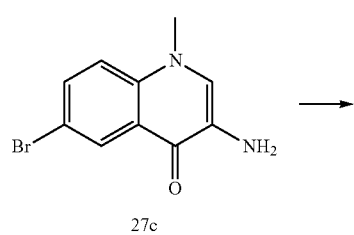

27c

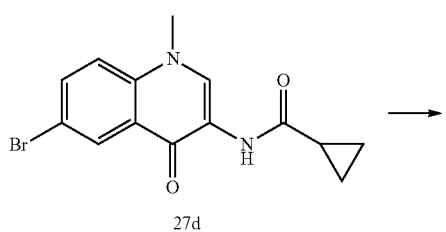

27d

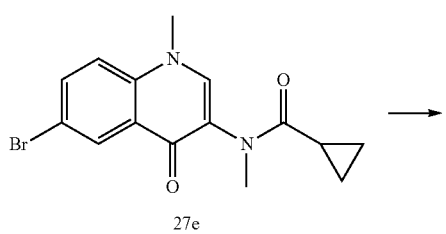

27e

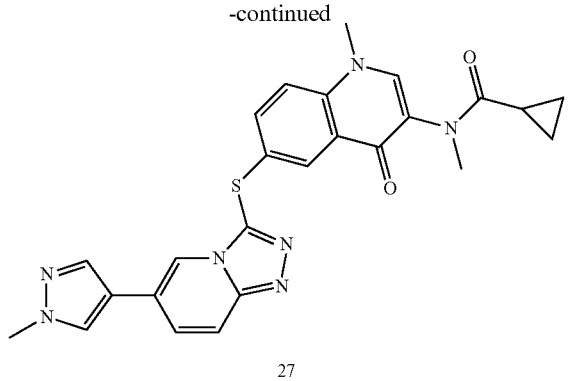

27

Step 1:
6-bromo-1-methyl-3-nitroquinolin-4(1H)-one 27b

To a 100 mL three-necked flask, 6-bromo-3-nitroquinolin-4-ol (1.0 g, 3.7 mmol), potassium carbonate (1.02 g, 7.4 mmol) and acetonitrile (50 mL) were added. The reaction mixture was stirred at room temperature, then iodomethane (2.64 g, 18.6 mmol) was added. The reaction mixture was stirred at room temperature for 14 hours. After LC-MS showed completion of the reaction, the reaction mixture was washed with sodium chloride aqueous solution, and the organic phase was dried and filtered. The solvent was removed by rotary evaporation to give 6-bromo-1-methyl-3-nitroquinolin-4(1H)-one 27b, (600 mg, yield 55%) as a black solid. The crude product was directly used in the next reaction. $R_f$=0.55 (dichloromethane/methanol=20/1).

MS m/z (ESI): 283, 285 [M+H]$^+$.

Step 2:
3-amino-6-bromo-1-methylquinolin-4(1H)-one 27c

To a 100 mL one-necked flask, 6-bromo-1-methyl-3-nitroquinolin-4(1H)-one (0.6 g, 2.12 mmol), methanol (20 mL) and hydrazine hydrate (0.63 g, 10.6 mmol) were added in an ice bath. A catalytic amount of Raney nickel was added, and the reaction solution was stirred at room temperature for 1 hour. After LC-MS showed completion of the reaction, the reaction mixture was filtered, and the filter cake was washed with methanol three times. The organic phase was dried by rotary evaporation to give 3-amino-6-bromo-1-methylquinolin-4(1H)-one (0.5 g, yield 93%).

MS m/z (ESI): 253, 255.

Step 3: N-(6-bromo-1-methyl-4-oxo-1,4-dihydroquinolin-3-yl)cyclopropanecarboxamide 27d To a 50 mL one-necked flask, 3-amino-6-bromo-1-methylquinolin-4(1H)-one (230 mg, 0.91 mmol), triethylamine (231 mg, 2.28 mmol) and anhydrous dichloromethane (20 mL) were added. The reaction mixture was stirred in an ice bath, then cyclopropanecarbonyl chloride (105 mg, 1 mmol) was dropwise added to the reaction solution. The reaction mixture was stirred at room temperature overnight. After LC-MS showed completion of the reaction, the solvent was removed by rotary evaporation. The residue was dissolved in ethyl acetate, and washed with saturated sodium bicarbonate solution and sodium chloride aqueous solution. The organic phase was dried and filtered, the solvent was removed by rotary evaporation to give N-(6-bromo-1-methyl-4-oxo-1,4- dihydroquinolin-3-yl)cyclopropanecarboxamide (145 mg, yield 50%) as a yellow solid.

MS m/z (ESI): 321, 323.

Step 4: N-(6-bromo-1-methyl-4-oxo-1,4-dihydroquinolin-3-yl)-N-methylcyclopropanecarboxamide 27e To a 50 mL three-necked flask, N-(6-bromo-1-methyl-4-oxo-1,4-dihydro quinolin-3-yl)cyclopropanecarboxamide (0.145 g, 0.45 mmol) and anhydrous N,N-dimethylformamide (3 mL) were added. The reaction mixture was stirred in an ice bath under N₂, then sodium hydride (60% in mineral oil, 0.034 g, 0.86 mmol) was added. After the reaction solution was stirred for half an hour, iodomethane (0.122 g, 0.86 mmol) was added. The reaction solution was stirred for 14 hours at room temperature. After LC-MS showed completion of the reaction, the reaction mixture was mixed with ethyl acetate (40 mL) and washed with sodium chloride aqueous solution. The organic phase was dried over anhydrous sodium sulfate and filtered. The solvent was removed by rotary evaporation, and the resulting residue was purified by preparative TLC (petroleum ether/ethyl acetate=1/1) to give N-(6-bromo-1-methyl-4-oxo-1,4-dihydroquinolin-3-yl)-N-methylcyclopropanecarboxamide (70 mg, yield 46%) as a white solid.

MS m/z (ESI): 279, 281.

Step 5: N-methyl-N-(1-methyl-6-((6-(1-methyl-1H-pyrazol-4-yl)-[1,2,4]triazolo[4,3-a]pyridin-3-yl)thio)-4-oxo-1,4-dihydroquinolin-3-yl)cyclopropanecarboxamide 27

To a 25 mL three-necked flask, N-(6-bromo-1-methyl-4-oxo-1,4-dihydroquinolin-3-yl)-N-methylcyclopropanecarboxamide (0.040 g, 1.19 mmol), 6-(1-methyl-1H-pyrazol-4-yl)-[1,2,4]triazolo[4,3-a]pyridin-3-thiol (0.028 g, 1.19 mmol), tri(dibenzylideneacetone)dipalladium (0.011 g, 0.019 mmol), 4,5-bis(diphenylphosphino)-9,9-dimethylxanthene (0.014 g, 0.038 mmol), sodium t-butoxide (0.015 g, 1.55 mmol) and anhydrous N,N-dimethylformamide (4 mL) were added. The reaction mixture was purged with N₂ three times and heated to 100° C. for 14 hours. After LC-MS showed completion of the reaction, the reaction mixture was filtered by celite, and washed with ethyl acetate (30 mL). The organic phase was washed with sodium chloride aqueous solution, dried and filtered. The solvent was removed by rotary evaporation, and the residue was purified by reverse phase column chromatography to give N-methyl-N-(1-methyl-6-((6-(1-methyl-1H-pyrazol-4-yl)-[1,2,4]triazolo[4,3-a]pyridin-3-yl)thio)-4-oxo-1,4-dihydroquinolin-3-yl)cyclopropanecarboxamide 27 (8 mg, yield 15%) as a white solid.

MS m/z (ESI): 486.

¹H-NMR (CDCl₃, 400M Hz): δ 8.70 (s, 1H), 8.29 (s, 1H), 7.87 (d, J=9.2 Hz, 1H), 7.71-7.77 (m, 4H), 7.52 (d, J=9.2 Hz, 1H), 7.39 (d, J=9.2 Hz, 1H), 3.99 (s, 3H), 3.83 (s, 3H), 3.21 (s, 3H), 1.43 (m, 1H), 1.08 (m, 1H), 0.89-0.92 (m, 1H), 0.58-0.60 (m, 2H).

Example 28

4-(4-fluoro-6-((6-(1-methyl-1H-pyrazol-4-yl)-[1,2,4]triazolo[4,3-a]pyridin-3-yl)thio)quinolin-3-yl)morpholine (28)

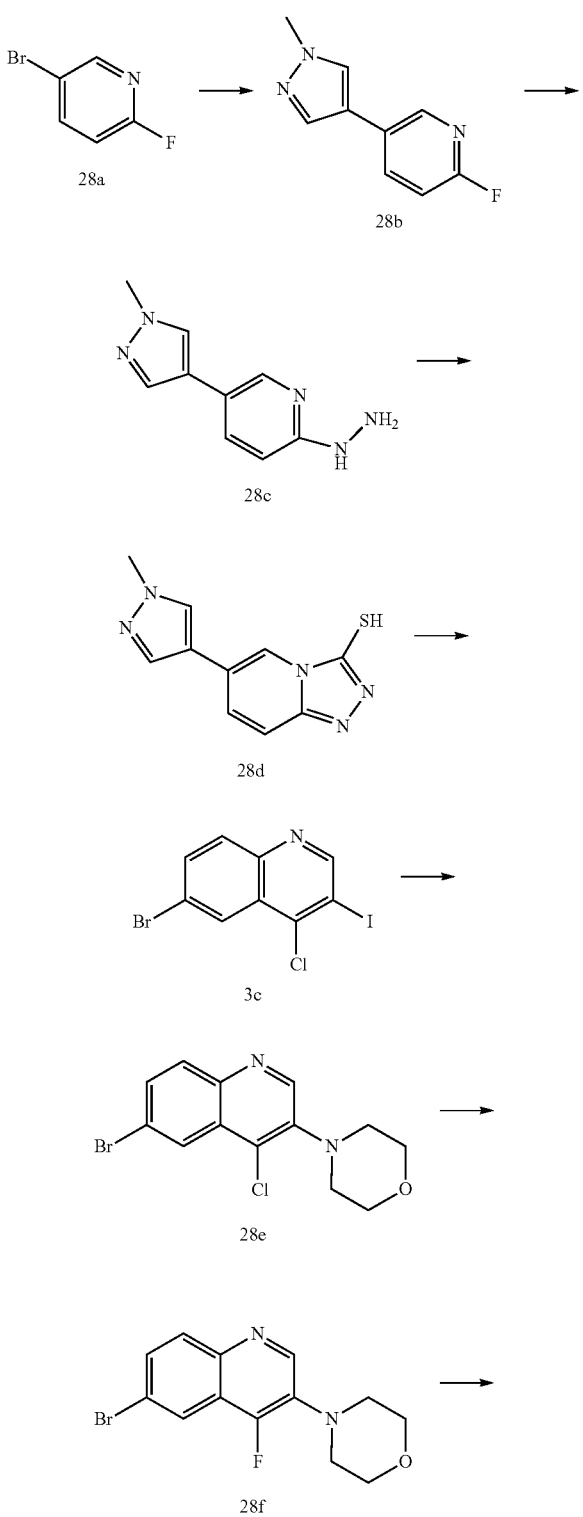

-continued

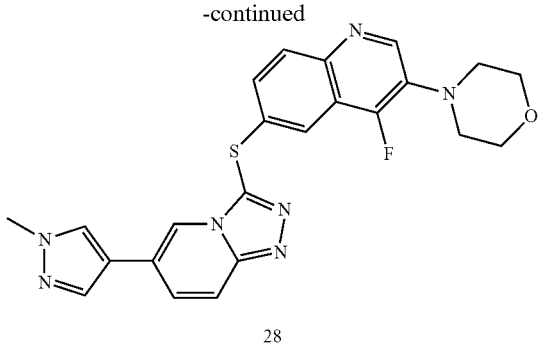

28

Step 1: 2-fluoro-5-(1-methyl-1H-pyrazol-4-yl)pyridine 28b 5-bromo-2-fluoropyridine (10.0 g, 56.82 mmol), 1-methyl-4-(4,4,5,5-tetramethyl-1,3,2-dioxaboronolan-2-yl)-1H-pyrazole (11.8 g, 56.82 mmol), [1,1'-bis(diphenylphosphino)ferrocene]dichloropalladium (4.6 g, 5.68 mmol) and potassium carbonate (23.5 g, 170.5 mmol) were dissolved in a mixed solution of 1,4-dioxane (120 mL) and water (30 mL). The reaction mixture was heated to 75° C. for 4 hours and then cooled to room temperature. The reaction solution was concentrated to dryness, the residue was added with ethyl acetate, and washed with sodium chloride aqueous solution. The organic phase was dried, filtered, and concentrated to dryness, and the resulting residue was purified by column chromatography (petroleum ether/ethyl acetate=2:1, v/v) to give 2-fluoro-5-(1-methyl-1H-pyrazol-4-yl)pyridine (11.3 g, yield about 100%) as a white solid.

MS m/z (ESI): 178.1

$^1$H NMR (400 MHz, DMSO-$d_6$, ppm): δ 8.47 (s, 1H), 8.23 (s, 1H), 8.15 (td, J=8.4, 2.4 Hz, 1H), 7.95 (s, 1H), 7.19 (dd, J=8.4, 2.8 Hz, 1H), 3.87 (s, 3H).

Step 2: 2-hydrazinyl-5-(1-methyl-1H-pyrazol-4-yl)pyridine 28c 2-fluoro-5-(1-methyl-1H-pyrazol-4-yl)pyridine (11.3 g, 56.82 mmol) was added to a 85% aqueous solution of hydrazine hydrate (30 mL). The resulting suspension was heated to 100° C. for 3 hours, and then cooled to 10° C. The solid was precipitated and filtered by a Büchner funnel, washed with cold ethanol and dried to give 2-hydrazinyl-5-(1-methyl-1H-pyrazol-4-yl)pyridine (12.5 g, yield about 100%) as a white solid.

MS m/z (ESI): 190.1

Step 3: 6-(1-methyl-1H-pyrazol-4-yl)-[1,2,4]triazolo[4,3-a]pyridin-3-thiol 28d 2-hydrazinyl-5-(1-methyl-1H-pyrazol-4-yl)pyridine (9.30 g, 49.15 mmol) was dissolved in ethanol (100 mL), and a pre-prepared aqueous solution of potassium hydroxide (3.03 g, 54.16 mmol, 25 mL) was slowly added to the reaction mixture at room temperature, followed by slow addition of carbon disulfide (7.85 g, 103.2 mmol). This yellow solution was heated to 65° C. for 48 hours. The reaction solution was concentrated to a small volume, and then dissolved in 50 mL of sodium hydroxide aqueous solution (2 N). The insoluble solid was removed by filtration, and the filtrate was acidified with a 2 N hydrochloric acid solution to pH=4. The resulting solid was collected by filtration and dried to give 6-(1-methyl-1H-pyrazol-4-yl)-[1,2,4]triazolo[4,3-a]pyridin-3-thiol (7.5 g, yield 96%) as a yellow powder.

MS m/z (ESI): 232.1

$^1$H NMR (400 MHz, DMSO-$d_6$, ppm): δ 14.65 (s, 1H), 8.37 (s, 1H), 8.35 (s, 1H), 8.02 (s, 1H), 7.77 (d, J=9.6 Hz, 1H), 7.69 (d, J=9.6 Hz, 1H), 3.89 (s, 3H).

Step 4: 4-(6-bromo-4-chloroquinolin-3-yl)morpholine 28e 6-bromo-4-chloro-3-iodoquinoline (5.00 g, 13.57 mmol), morpholine (1.42 g, 16.29 mmol), tris(dibenzylideneacetone)dipalladium (1.24 g, 1.36 mmol) and 4,5-bis(diphenylphosphino)-9,9-dimethylxanthene (1.57 g, 2.71 mmol) were all dissolved in anhydrous N,N-dimethylformamide (90 mL). The reaction mixture was heated to 35° C. and stirred for 1 hour under $N_2$, then sodium tert-butoxide (1.56 g, 1.629 mmol) was added. The reaction mixture was kept at this temperature for 16 hours. Then it was concentrated to dryness under reduced pressure. Ethyl acetate was added, and the organic phase was washed with sodium chloride aqueous solution, dried, filtered and concentrated. The resulting residue was purified by column chromatography (dichloromethane/methanol=100:1, v/v), pulverized, and filtered to give 4-(6-bromo-4-chloroquinolin-3-yl)morpholine (2.5 g, yield 56%) as a white solid.

MS m/z (ESI): 329.0

Step 5: 4-(6-bromo-4-fluoroquinolin-3-yl)morpholine 28f 4-(6-bromo-4-chloroquinolin-3-yl)morpholine (160 mg, 0.49 mmol) and cesium fluoride (222 mg, 1.47 mmol) were all dissolved in anhydrous dimethyl sulfoxide (10 mL). The reaction mixture was heated to 100° C. and stirred for 6 days. When most of the raw materials (~90%) were converted to the desired product, the reaction was stopped. The reaction mixture was mixed with ethyl acetate, washed with sodium chloride aqueous solution and dried. The organic solvent was filtered and concentrated to dryness. The crude product was purified by column chromatography (dichloromethane/methanol=100:1, v/v), pulverized, and filtered to give 4-(6-bromo-4-fluoroquinolin-3-yl)-morpholine (80 mg, yield 53%) as a white solid.

MS m/z (ESI): 311.0

$^1$H NMR (400 MHz, DMSO-$d_6$, ppm): δ 8.94 (d, J=10.8 Hz, 1H), 8.23 (s, 1H), 7.99 (d, J=9.2 Hz, 1H), 7.84 (d, J=9.2 Hz, 1H), 3.85 (t, J=4.8 Hz, 4H), 3.37 (t, J=4.8 Hz, 4H).

Step 6: 4-(4-fluoro-6-((6-(1-methyl-1H-pyrazol-4-yl)-[1,2,4]triazolo[4,3-a]pyridin-3-yl)thio)quinolin-3-yl)morpholine 28

6-(1-methyl-1H-pyrazol-4-yl)-[1,2,4]triazolo[4,3-a]pyridin-3-thiol (60 mg, 0.26 mmol), 4-(6-bromo-4-fluoroquinolin-3-yl)morpholine (80 mg, 0.26 mmol), tris(dibenzylideneacetone)dipalladium (24 mg, 0.026 mmol), 4,5-bis(diphenylphosphino)-9,9-dimethylxanthene (30 mg, 0.052 mmol) and N,N-diisopropylethylamine (133 mg, 1.04 mmol) were dissolved in anhydrous N,N-dimethyl formamide (2 mL) under $N_2$, the reaction mixture was heated to 100° C. and stirred for 48 hours, and then concentrated to dryness under reduced pressure. The crude product was purified by column chromatography (dichloromethane/methanol/aqueous ammonia=500:10:1, v/v/v), pulverized, and filtered to give a yellow solid, and then further recrystallizated to give 4-(4-fluoro-6-((6-(1-methyl-1H-pyrazol-4-yl)-[1,2,4]triazolo[4,3-a]pyridine-3-yl)thio)quinolin-3-yl)morpholine 28 (12 mg, yield 10%) as a white solid.

MS m/z (ESI): 462.1

$^1$H NMR (400 MHz, DMSO-$d_6$, ppm): δ 8.79 (d, J=10.8 Hz, 1H), 8.64 (s, 1H), 8.34 (s, 1H), 8.03 (s, 1H), 8.01 (d, J=9.4 Hz, 1H), 7.92 (d, J=8.8 Hz, 1H), 7.82 (d, J=9.4 Hz, 1H), 7.80 (d, J=2.0 Hz, 1H), 7.42 (dd, J=8.8, 2.0 Hz, 1H), 3.85 (s, 3H), 3.76 (t, J=4.8 Hz, 4H), 3.26 (t, J=4.8 Hz, 4H).

Example 29

4-methoxy-6-((6-(1-methyl-1H-pyrazol-4-yl)-[1,2,4]triazolo[4,3-a]pyridin-3-yl)thio)quinoline (29)

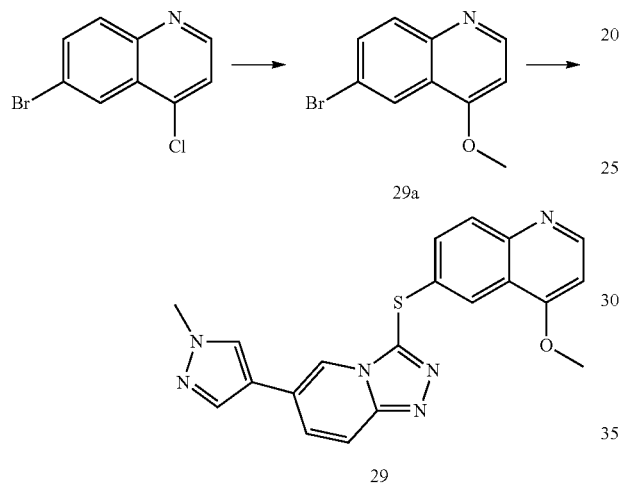

29

Step 1: 6-bromo-4-methoxyquinoline 29a 6-bromo-4-chloroquinoline (1.00 g, 4.124 mmol) and sodium methoxide (1.11 g, 20.62 mmol) were dissolved in methanol (15 mL). The reaction mixture was heated to 108° C. in a sealed system for 16 hours, and then concentrated to dryness. The residue was dissolved in ethyl acetate, washed with sodium chloride aqueous solution and dried. The organic solvent was filtered and concentrated, and the residue was purified by column chromatography (petroleum ether/ethyl acetate=5:1, v/v) to give 6-bromo-4-methoxyquinoline (872 mg, yield 89%) as a pale yellow solid.

MS m/z (ESI): 238.0

Step 2: 4-methoxy-6-((6-(1-methyl-1H-pyrazol-4-yl)-[1,2,4]triazolo[4,3-a]pyridin-3-yl)thio)quinoline 29

6-(1-methyl-1H-pyrazol-4-yl)-[1,2,4]triazolo[4,3-a]pyridin-3-thiol (100 mg, 0.43 mmol), 6-bromo-4-methoxyquinoline (103 mg, 0.43 mmol), tri(dibenzylpropanone)dipalladium (40 mg, 0.043 mmol), 4,5-bis(diphenylphosphino)-9,9-dimethylxanthene (50 mg, 0.086 mmol) and N,N-diisopropylethylamine (223 mg, 1.73 mmol) were dissolved in anhydrous N,N-dimethylformamide (2 mL) under $N_2$, the reaction mixture was heated to 100° C. for 16 hours and then concentrated to dryness under reduced pressure. The residue was purified by column chromatography (dichloromethane/methanol=20:1, v/v), pulverized, and filtered to give 4-methoxy-6-((6-(1-methyl-1H-pyrazol-4-yl)-[1,2,4]triazolo[4,3-a]pyridin-3-yl)thio)quinoline 29 (70 mg, yield 42%) as a white solid.

MS m/z (ESI): 389.1

$^1$H NMR (400 MHz, DMSO-$d_6$, ppm): δ 8.71 (d, J=5.2 Hz, 1H), 8.65 (s, 1H), 8.35 (s, 1H), 8.06 (d, J=2.0 Hz, 1H), 8.03 (s, 1H), 7.99 (d, J=9.6 Hz, 1H), 7.90 (d, J=8.8 Hz, 1H), 7.81 (d, J=9.2 Hz, 1H), 7.60 (dd, J=8.8, 2.0 Hz, 1H), 7.04 (d, J=5.2 Hz, 1H), 4.00 (s, 3H), 3.86 (s, 3H).

Example 30

4-(6-((6-(1-methyl-1H-pyrazol-4-yl)-[1,2,4]triazolo[4,3-a]pyridin-3-yl)thio)quinolin-4-yl)morpholine (30)

6-(1-methyl-1H-pyrazol-4-yl)-[1,2,4]triazolo[4,3-a]pyridin-3-thiol (80 mg, 0.35 mmol), 4-(6-bromoquinolin-4-yl)morpholine (101 mg, 0.35 mmol), tris(dibenzylideneacetone)dipalladium (32 mg, 0.035 mmol), 4,5-bis(diphenylphosphino)-9,9-dimethylxanthene (40 mg, 0.069 mmol) and N,N-diisopropylethylamine (179 mg, 1.38 mmol) were dissolved in anhydrous N,N-dimethylformamide (2 mL) under $N_2$, the reaction mixture was heated to 100° C. for 16 hours and concentrated to dryness under reduced pressure. The residue was purified by column chromatography (dichloromethane/methanol=20:1, v/v), pulverized, and filtered to give 4-(6-((6-(1-methyl-1H-pyrazol-4-yl)-[1,2,4]triazolo[4,3-a]pyridin-3-yl)thio)quinolin-4-yl)morpholine 30 (71 mg, yield 46%) as a white solid.

MS m/z (ESI): 444.2

$^1$H NMR (400 MHz, DMSO-$d_6$, ppm): δ 8.64-8.66 (m, 2H), 8.34 (s, 1H), 8.08 (d, J=9.6 Hz, 1H), 8.02 (s, 1H), 7.95 (d, J=9.2 Hz, 1H), 7.86 (d, J=9.4 Hz, 1H), 7.68 (dd, J=8.8, 2.0 Hz, 1H), 7.37 (d, J=2.4 Hz, 1H), 6.96 (d, J=4.8 Hz, 1H), 3.84 (s, 3H), 3.56 (t, J=4.0 Hz, 4H), 2.90 (t, J=4.4 Hz, 4H).

Example 31

9-((6-(1-methyl-1H-pyrazol-4-yl)-[1,2,4]triazolo[4,3-a]pyridin-3-yl)thio)-2,3-dihydro-[1,4]dioxino[2,3-c]quinoline (31)

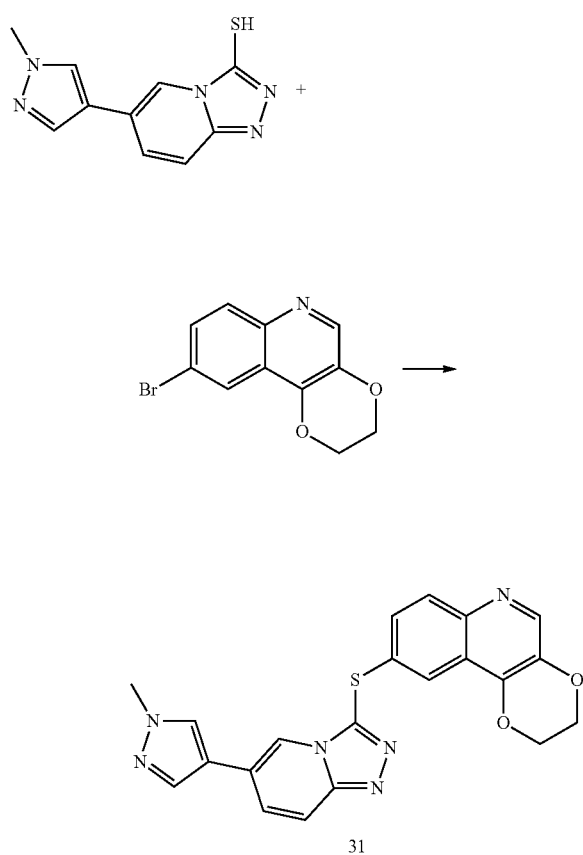

31

6-(1-methyl-1H-pyrazol-4-yl)-[1,2,4]triazolo[4,3-a]pyridin-3-thiol (80 mg, 0.35 mmol), 9-bromo-2,3-dihydro-[1,4]dioxino[2,3-c]quinoline (92 mg, 0.35 mmol), tris(dibenzylideneacetone)dipalladium (32 mg, 0.035 mmol), 4,5-bis(diphenylphosphino)-9,9-dimethylxanthene (40 mg, 0.069 mmol) and N,N-diisopropylethylamine (179 mg, 1.38 mmol) were dissolved in anhydrous N,N-dimethylformamide (2 mL) under $N_2$, the reaction mixture was heated to 100° C. for 16 hours and concentrated to dryness under reduced pressure. The residue was purified by column chromatography (dichloromethane/methanol=20:1, v/v), pulverized, and filtered to give 9-((6-(1-methyl-1H-pyrazol-4-yl)-[1,2,4]triazolo[4,3-a]pyridin-3-yl)thio)-2,3-dihydro-[1,4]dioxio[2,3-c]quinoline 31 (12 mg, yield 8%) as a white solid.

MS m/z (ESI): 417.1

$^1$H NMR (400 MHz, DMSO-$d_6$, ppm): δ 8.64 (s, 1H), 8.51 (s, 1H), 8.35 (s, 1H), 8.04 (s, 1H), 8.01 (d, J=9.4 Hz, 1H), 7.86 (d, J=8.8 Hz, 1H), 7.82 (dd, J=9.2, 1.6 Hz, 1H), 7.77 (d, J=2.0 Hz, 1H), 7.47 (dd, J=8.8, 2.4 Hz, 1H), 4.49-4.51 (m, 2H), 4.37-4.39 (m, 2H), 3.86 (s, 3H).

Example 32

4-chloro-6-((6-(1-methyl-1H-pyrazol-4-yl)-[1,2,4]triazolo[4,3-a]pyridin-3-yl)thio)quinolone (32)

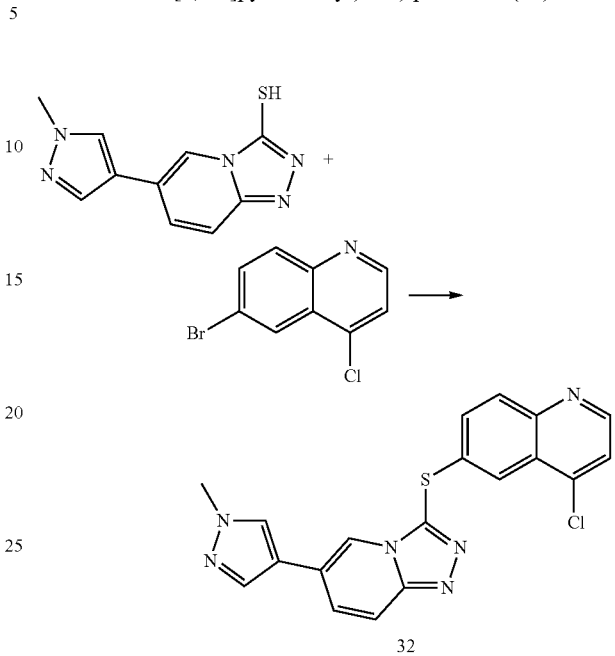

32

6-(1-methyl-1H-pyrazol-4-yl)-[1,2,4]triazolo[4,3-a]pyridin-3-thiol (200 mg, 0.86 mmol), 4-chloro-6-bromoquinoline (210 mg, 0.86 mmol), tri(dibenzenylpropanone)dipalladium (79 mg, 0.086 mmol), 4,5-bis(diphenylphosphino)-9,9-dimethylxanthene (100 mg, 0.17 mmol) and N,N-diisopropylethylamine (447 mg, 3.46 mmol) were dissolved in anhydrous N,N-dimethylformamide (5 mL) under $N_2$, the reaction mixture was heated to 100° C. for 16 hours and concentrated to dryness under reduced pressure. The residue was purified by column chromatography (dichloromethane/methanol=20:1, v/v), pulverized, and filtered to give 4-chloro-6-((6-(1-methyl-1H-pyrazol-4-yl)-[1,2,4]triazolo[4,3-a]pyridin-3-yl)thio)quinoline 32 (135 mg, yield 40%) as a white solid.

MS m/z (ESI): 393.1

$^1$H NMR (400 MHz, DMSO-$d_6$, ppm): δ 8.81 (d, J=4.8 Hz, 1H), 8.69 (s, 1H), 8.35 (s, 1H), 8.05 (d, J=8.8 Hz, 1H), 8.04 (s, 1H), 8.03 (d, J=8.8 Hz, 1H), 8.02 (d, J=2.0 Hz, 1H), 7.85 (d, J=9.4 Hz, 1H), 7.78 (d, J=4.8 Hz, 1H), 7.63 (d, J=9.0 Hz, 1H), 3.85 (s, 3H).

Example 33

2-((6-((6-(1-methyl-1H-pyrazol-4-yl)-[1,2,4]triazolo[4,3-a]pyridin-3-yl)thio)quinolin-4-yl)oxy)ethan-1-ol (33)

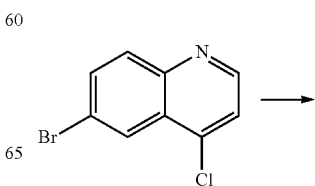

-continued

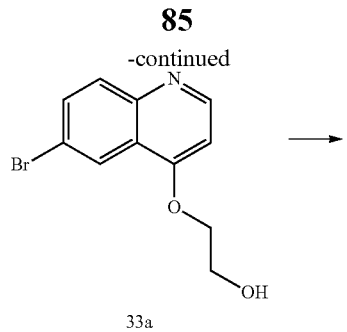

33a

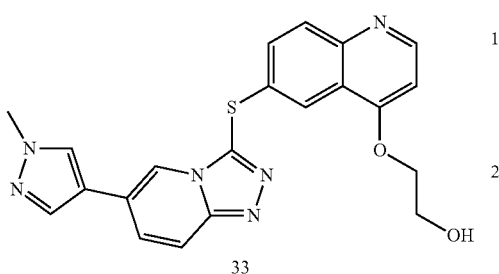

33

Step 1: 2-((6-bromoquinolin-4-yl)oxy)ethan-1-ol 33a

Sodium hydride (60%, 330 mg, 8.25 mmol) was suspended into anhydrous N,N-dimethylformamide (15 mL) under $N_2$, then ethylene glycol (1.28 g, 20.62 mmol) was added dropwise with stirring. The reaction mixture was stirred for 20 minutes and then 6-bromo-4-chloroquinoline (1.00 g, 4.12 mmol) was added. The reaction mixture was heated to 90° C. for 16 hours, and cooled, and then concentrated to dryness under reduced pressure. The residue was washed with 1N sodium hydroxide aqueous solution and sodium chloride aqueous solution, and then dried, filtered and concentrated. The resulting residue was purified by column chromatography (dichloromethane/methanol=20:1, v/v) to give 2-((6-bromoquinolin-4-yl)oxy)ethan-1-ol (230 mg, yield 21%) as a white solid.

MS m/z (ESI): 268.0

$^1$H NMR (400 MHz, DMSO-$d_6$, ppm): δ 8.75 (d, J=5.2 Hz, 1H), 8.44 (s, 1H), 7.85-7.91 (m, 2H), 7.07 (d, J=5.2 Hz, 1H), 5.16 (t, J=5.8 Hz, 1H), 4.26 (t, J=4.4 Hz, 2H), 3.85-3.89 (m, 2H).

Step 2: 2-((6-((6-(1-methyl-1H-pyrazol-4-yl)-[1,2,4]triazolo[4,3-a]pyridin-3-yl)thio)quinolin-4-yl)oxy)ethan-1-ol 33

6-(1-methyl-1H-pyrazol-4-yl)-[1,2,4]triazolo[4,3-a]pyridin-3-thiol (80 mg, 0.35 mmol), 2-((6-bromoquinolin-4-yl)oxy)ethan-1-ol (93 mg, 0.35 mmol), tri(dibenzylideneacetone)dipalladium (32 mg, 0.035 mmol), 4,5-bis(diphenylphosphino)-9,9-dimethylxanthene (40 mg, 0.069 mmol) and N,N-diisopropylethylamine (179 mg, 1.38 mmol) were dissolved in anhydrous N,N-dimethylformamide (2 mL) under $N_2$, and the reaction mixture was heated to 100° C. and stirred for 16 hours. The mixture was concentrated to dryness under reduced pressure, and the residue was purified by column chromatography (dichloromethane/methanol=20:1, dichloromethane/acetone=8:1, v/v), pulverized, and filtered to give 2-((6-((6-(1-methyl-1H-pyrazol-4-yl)-[1,2,4]triazolo[4,3-a]pyridine-3-yl)thio)quinolin-4-yl)oxy)ethan-1-ol 33 (15 mg, yield 10%) as a white solid.

MS m/z (ESI): 419.1.

$^1$H NMR (400 MHz, DMSO-$d_6$, ppm): δ 8.70 (d, J=5.2 Hz, 1H), 8.67 (s, 1H), 8.39 (s, 1H), 8.35 (s, 1H), 8.03 (s, 1H), 7.98 (d, J=9.2 Hz, 1H), 7.87 (d, J=8.8 Hz, 1H), 7.81 (d, J=9.2 Hz, 1H), 7.49 (d, J=8.8 Hz, 1H), 7.05 (d, J=5.2 Hz, 1H), 5.13 (t, J=5.8 Hz, 1H), 4.25 (t, J=4.8 Hz, 2H), 3.87 (s, 3H), 3.83-3.86 (m, 2H).

Example 34

2-(methyl(6-((6-(1-methyl-1H-pyrazol-4-yl)-[1,2,4]triazolo[4,3-a]pyridin-3-yl)thio)quinolin-4-yl)amino)ethan-1-ol (34)

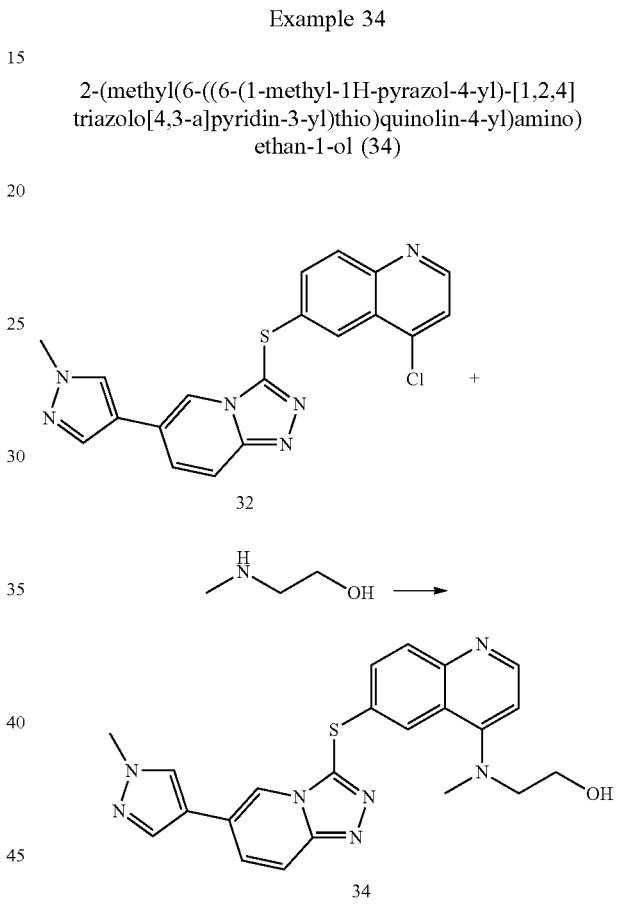

4-chloro-6-((6-(1-methyl-1H-pyrazol-4-yl)-[1,2,4]triazolo[4,3-a]pyridin-3-yl)thio)quinoline (70 mg, 0.18 mmol) and 2-(methylamino)ethanol (3 mL) were placed in a sealed tube, and the reaction mixture was heated to 120° C. for 16 hours. The reaction solution was cooled and concentrated to dryness under reduced pressure. The crude product was purified by column chromatography (dichloromethane/methanol=20:1, v/v) to give 2-(methyl(6-((6-(1-methyl-1H-pyrazol-4-yl)-[1,2,4]triazolo[4,3-a]pyridin-3-yl)thio)quinolin-4-yl)amino)ethan-1-ol 34 (45 mg, yield 58%) as a pale yellow solid.

MS m/z (ESI): 432.2

$^1$H NMR (400 MHz, DMSO-$d_6$, ppm): δ 8.63 (s, 1H), 8.54 (d, J=5.2 Hz, 1H), 8.33 (s, 1H), 8.18 (s, 1H), 8.01 (s, 1H), 7.99 (d, J=9.6 Hz, 1H), 7.85 (d, J=9.2 Hz, 1H), 7.81 (d, J=9.6 Hz, 1H), 7.53 (d, J=8.8 Hz, 1H), 6.91 (d, J=5.2 Hz, 1H), 4.81 (t, J=5.2 Hz, 1H), 3.86 (s, 3H), 3.56-3.58 (m, 2H), 3.23 (t, J=5.6 Hz, 2H), 2.90 (s, 3H).

Example 35

N-(2-methoxyethyl)-N-methyl-6-((6-(1-methyl-1H-pyrazol-4-yl)-[1,2,4]triazolo[4,3-a]pyridin-3-yl)thio)quinolin-4-amine (35)

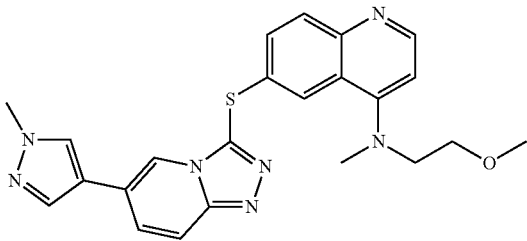

4-chloro-6-((6-(1-methyl-1H-pyrazol-4-yl)-[1,2,4]triazolo[4,3-a]pyridin-3-yl)thio)quinoline (60 mg, 0.153 mmol) and 2-methoxy-N-methyl-ethylamine (2 mL) were placed in a sealed tube, and the reaction mixture was heated to reflux for 16 hours. The reaction solution was cooled and concentrated to dryness under reduced pressure. The residue was purified by column chromatography (dichloromethane/methanol=20:1, v/v) to give N-(2-methoxyethyl)-N-methyl-6-((6-(1-methyl-1H-pyrazol-4-yl)-[1,2,4]triazolo[4,3-a]pyridin-3-yl)thio)quinolin-4-amine 35 (36 mg, yield 53%) as a pale yellow solid.

MS m/z (ESI): 446.2.

$^1$H NMR (400 MHz, DMSO-$d_6$, ppm): δ 8.62 (s, 1H), 8.55 (d, J=5.6 Hz, 1H), 8.33 (s, 1H), 8.02 (d, J=9.4 Hz, 1H), 8.00 (s, 1H), 7.95 (s, 1H), 7.88 (d, J=8.8 Hz, 1H), 7.82 (d, J=9.4 Hz, 1H), 7.62 (d, J=8.8 Hz, 1H), 6.93 (d, J=5.6 Hz, 1H), 3.85 (s, 3H), 3.43 (t, J=5.2 Hz, 2H), 3.30-3.33 (m, 2H), 3.17 (s, 3H), 2.91 (s, 3H).

Example 36

4-chloro-3-(1-methyl-1H-pyrazol-4-yl)-6-((6-(1-methyl-1H-pyrazol-4-yl)-[1,2,4]triazolo[4,3-a]pyridin-3-yl)thio)quinoline (36)

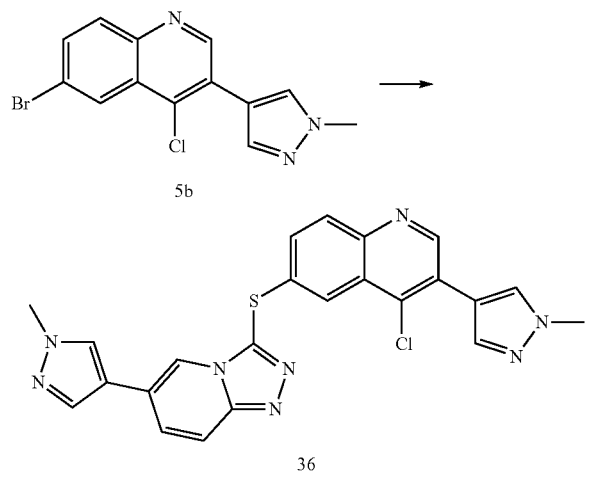

Step 1: 4-chloro-3-(1-methyl-1H-pyrazol-4-yl)-6-((6-(1-methyl-1H-pyrazol-4-yl)-[1,2,4]triazolo[4,3-a]pyridin-3-yl)thio)quinoline (36)

6-(1-methyl-1H-pyrazol-4-yl)-[1,2,4]triazolo[4,3-a]pyridin-3-thiol (72 mg, 0.31 mmol), 6-bromo-4-chloro-3-(1-methyl-1H-pyrazol-4-yl)quinoline (100 mg, 0.31 mmol), tris(dibenzylideneacetone)dipalladium (28 mg, 0.031 mmol), 4,5-bis(diphenylphosphino)-9,9-dimethylxanthene (36 mg, 0.062 mmol) and N,N-diisopropylethylamine (160 mg, 1.25 mmol) were dissolved in anhydrous 1,4-dioxane (2 mL) under $N_2$, the reaction mixture was heated to 85° C. and stirred for 16 hours, and then concentrated to dryness under reduced pressure. The residue was purified by column chromatography (dichloromethane/methanol=20:1, v/v), pulverized, and filtered to give 4-chloro-3-(1-methyl-1H-pyrazol-4-yl)-6-((6-(1-methyl-1H-pyrazol-4-yl)-[1,2,4]triazolo[4,3-a]pyridin-3-yl)thio)quinoline (80 mg, yield 54%) as a white solid.

MS m/z (ESI): 473.1

$^1$H NMR (400 MHz, DMSO-$d_6$, ppm): δ 9.10 (s, 1H), 8.69 (s, 1H), 8.48 (s, 1H), 8.36 (s, 1H), 8.13 (s, 1H), 8.09 (d, J=2.0 Hz, 1H), 8.05 (s, 1H), 8.04 (d, J=6.4 Hz, 1H), 8.01 (d, J=6.4 Hz, 1H), 7.85 (dd, J=9.6, 1.6 Hz, 1H), 7.56 (dd, J=9.2, 1.6 Hz, 1H), 3.95 (s, 3H), 3.85 (s, 3H).

Example 37

4-methoxy-3-(1-methyl-1H-pyrazol-4-yl)-6-((6-(1-methyl-1H-pyrazol-4-yl)-[1,2,4]triazolo[4,3-a]pyridin-3-yl)thio)quinoline (37)

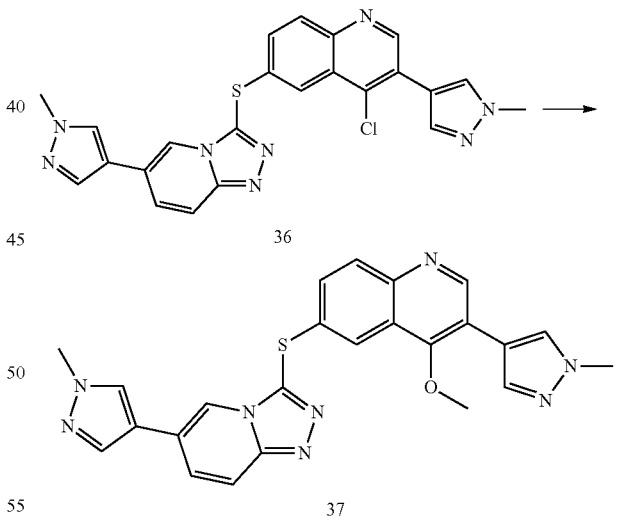

4-chloro-3-(1-methyl-1H-pyrazol-4-yl)-6-((6-(1-methyl-1H-pyrazol-4-yl)-[1,2,4]triazolo[4,3-a]pyridin-3-yl)thio)quinoline (65 mg, 0.14 mmol), sodium methoxide (37 mg, 0.69 mmol) and methanol (2 mL) were placed in a sealed tube, and the reaction mixture was heated to 112° C. for 16 hours. The reaction solution was cooled and concentrated to dryness under reduced pressure. The residue was purified by column chromatography (dichloromethane/methanol=20:1, v/v), and recrystallized to give 4-methoxy-3-(1-methyl-1H-pyrazol-4-yl)-6-((6-(1-methyl-1H-pyrazol-4-yl)-[1,2,4]triazolo[4,3-a]pyridin-3-yl)thio)quinoline 37 (41 mg, yield 64%) as a white solid.

MS m/z (ESI): 469.2.

$^1$H NMR (400 MHz, DMSO-d$_6$, ppm): δ 9.16 (s, 1H), 8.70 (s, 1H), 8.37 (s, 1H), 8.35 (s, 1H), 8.10 (s, 1H), 8.05 (s, 1H), 8.03 (d, J=9.4 Hz, 1H), 7.96 (d, J=8.8 Hz, 1H), 7.93 (d, J=2.0 Hz, 1H), 7.84 (d, J=9.2 Hz, 1H), 7.52 (dd, J=8.8, 2.0 Hz, 1H), 3.93 (s, 3H), 3.85 (s, 3H), 3.73 (s, 3H).

Example 38

4-methoxy-6-((8-methoxy-6-(1-methyl-1H-pyrazol-4-yl)-[1,2,4]triazolo[4,3-a]pyridin-3-yl)thio)-3-(1-methyl-1H-pyrazol-4-yl)quinoline (38)

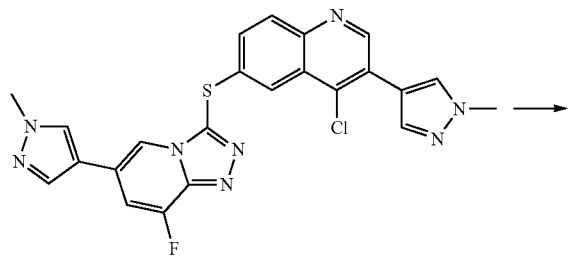

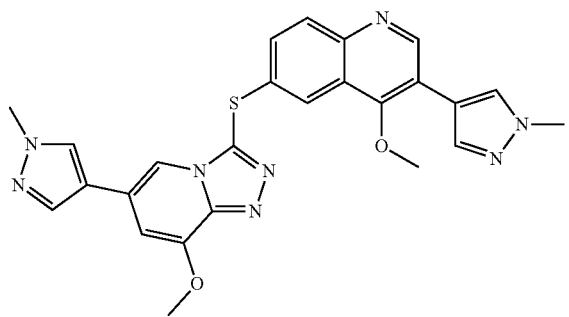

38

4-chloro-6-((8-fluoro-6-(1-methyl-1H-pyrazol-4-yl)-[1,2,4]triazolo[4,3-a]pyridin-3-yl)thio)-3-(1-methyl-1H-pyrazol-4-yl)quinoline (65 mg, 0.13 mmol), sodium methoxide (36 mg, 0.66 mmol) and methanol (5 mL) were placed in a sealed tube, and the reaction mixture was heated to 100° C. for 16 hours. The mixture was cooled and concentrated to dryness under reduced pressure. The crude product was purified by column chromatography (dichloromethane/methanol=20:1, v/v), pulverized, and filtered to give 4-methoxy-6-((8-methoxy-6-(1-methyl-1H-pyrazol-4-yl)-[1,2,4]triazolo[4,3-a]pyridin-3-yl)thio)-3-(1-methyl-1H-pyrazol-4-yl)quinoline 38 (30 mg, yield 45%) as a white solid.

MS m/z (ESI): 499.2.

$^1$H NMR (400 MHz, DMSO-d$_6$, ppm): δ 9.16 (s, 1H), 8.37 (s, 2H), 8.31 (s, 1H), 8.10 (s, 1H), 8.05 (s, 1H), 7.96 (d, J=8.8 Hz, 1H), 7.94 (s, 1H), 7.49 (d, J=8.8 Hz, 1H), 7.15 (s, 1H), 4.11 (s, 3H), 3.93 (s, 3H), 3.85 (s, 3H), 3.75 (s, 3H).

Example 39

4-(4-methoxy-6-((6-(1-methyl-1H-pyrazol-4-yl)[1,2,4]triazolo[4,3-a]pyridin-3-yl)thio)quinolin-3-yl)morpholine (39)

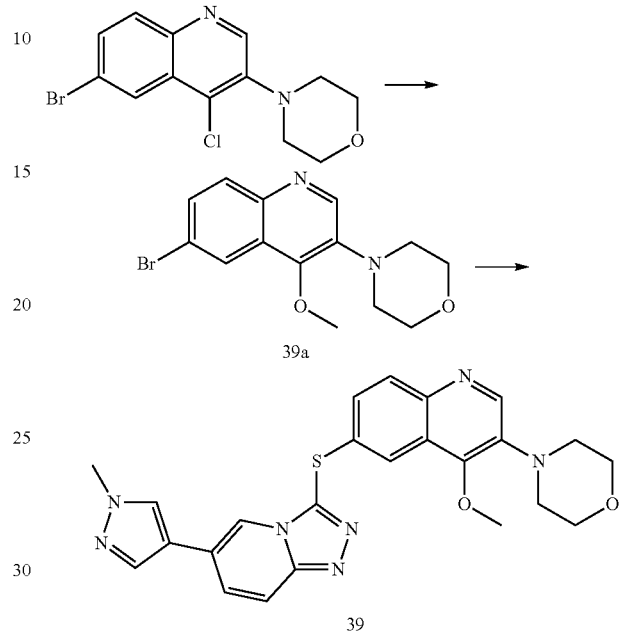

39

Step 1: 4-(6-bromo-4-methoxyquinolin-3-yl)morpholine 39a 4-(6-bromo-4-chloroquinolin-3-yl)morpholine (83 mg, 0.25 mmol) and sodium methoxide (68 mg, 1.27 mmol) were dissolved in methanol (5 mL). The reaction mixture was heated to 65° C. for 16 hours, and then cooled to room temperature and concentrated to dryness under reduced pressure. The crude product was purified by column chromatography (dichloromethane/methanol=20:1, v/v) to give 4-(6-bromo-4-methoxy-quinolin-3-yl)morpholine (32 mg, yield 39%) as a white solid.

MS m/z (ESI): 323.0

$^1$H NMR (400 MHz, DMSO-d$_6$, ppm): δ 8.79 (s, 1H), 8.20 (s, 1H), 7.88 (d, J=8.8 Hz, 1H), 7.72 (d, J=8.8 Hz, 1H), 4.04 (s, 3H), 3.83 (t, J=4.8 Hz, 4H), 3.23 (t, J=4.8 Hz, 4H).

Step 2: 4-(4-methoxy-6-((6-(1-methyl-1H-pyrazol-4-yl)-[1,2,4]triazolo[4,3-a]pyridin-3-yl)thio)quinolin-3-yl)morpholine (39)

6-(1-methyl-1H-pyrazol-4-yl)-[1,2,4]triazolo[4,3-a]pyridin-3-thiol (33 mg, 0.14 mmol), 4-(6-bromo-4-methoxyquinolin-3-yl)morpholine (46 mg, 0.14 mmol), tris(dibenzylideneacetone)dipalladium (13 mg, 0.014 mmol), 4,5-bis(diphenylphosphino)-9,9-dimethylxanthene (16 mg, 0.029 mmol) and N,N-diisopropylethylamine (74 mg, 0.57 mmol) were dissolved in anhydrous N,N-dimethylformamide (2 mL) under N$_2$, the reaction mixture was heated to 110° C. and stirred for 56 hours, and then concentrated to dryness under reduced pressure. The crude product was purified by column chromatography (dichloromethane/methanol=25:1, v/v), pulverized, and filtered to give 4-(4-methoxy-6-((6-(1-methyl-1H-pyrazol-4-yl)-[1,2,4]triazolo[4,3-a]pyridin-3-yl)thio)quinolin-3-yl)morpholine 39 (12 mg, yield 18%) as a white solid.

MS m/z (ESI): 474.2

$^1$H NMR (400 MHz, CDCl$_3$, ppm): δ 8.61 (s, 1H), 8.13 (s, 1H), 8.07 (s, 1H), 8.01 (s, 1H), 7.83 (d, J=9.2 Hz, 1H), 7.62 (s, 1H), 7.55 (s, 1H), 7.41-7.45 (m, 2H), 4.04 (s, 3H), 3.88 (s, 3H), 3.84 (t, J=4.8 Hz, 4H), 3.14 (t, J=4.8 Hz, 4H).

Example 40

6-((8-fluoro-6-(1-methyl-1H-pyrazol-4-yl)-[1,2,4]triazolo[4,3-a]pyridin-3-yl)thio)-4-methoxy-3-(1-methyl-1H-pyrazol-4-yl)quinoline (40)

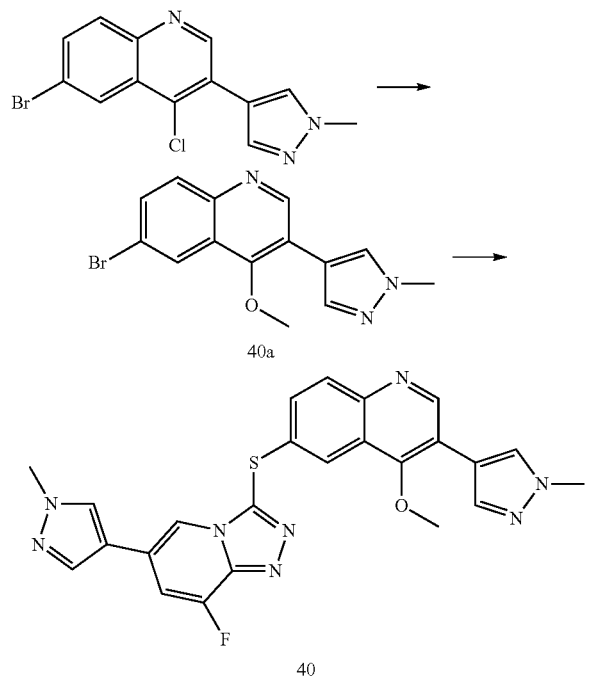

Step 1: 6-bromo-4-methoxy-3-(1-methyl-1H-pyrazol-4-yl)quinoline 40a 6-bromo-4-chloro-3-(1-methyl-1H-pyrazol-4-yl)quinoline (50 mg, 0.16 mmol) and sodium methoxide (42 mg, 0.77 mmol) were dissolved in methanol (2 mL). The reaction mixture was heated to 65° C. for 16 hours, cooled, and then concentrated to dryness under reduced pressure. The crude product was purified by column chromatography (dichloromethane/methanol=20:1, v/v) to give 6-bromo-4-methoxy-3-(1-methyl-1H-pyrazol-4-yl)quinoline (83 mg, a brown solid), which was used directly in the next step.

MS m/z (ESI): 318.0

Step 2: 6-((8-fluoro-6-(1-methyl-1H-pyrazol-4-yl)-[1,2,4]triazolo[4,3-a]pyridin-3-yl)thio)-4-methoxy-3-(1-methyl-1H-pyrazol-4-yl)quinoline 40

8-fluoro-6-(1-methyl-1H-pyrazol-4-yl)-[1,2,4]triazolo[4,3-a]pyridin-3-thiol (65 mg, 0.26 mmol), 6-bromo-4-methoxy-3-(1-methyl-1H-pyrazol-4-yl)quinoline (83 mg, 0.26 mmol), tris(dibenzylideneacetone)dipalladium (24 mg, 0.026 mmol), 4,5-bis(diphenylphosphino)-9,9-dimethylxanthene (30 mg, 0.052 mmol) and N,N-diisopropylethylamine (135 mg, 1.04 mmol) were dissolved in anhydrous 1,4-dioxane (2 mL) under N$_2$, the reaction mixture was heated to 85° C. for 16 h, and concentrated to dryness under reduced pressure. The crude product was purified twice by column chromatography (dichloromethane/methanol=25:1, v/v) to give a solid, and then the solid was purified by reverse phase column to give 6-((8-fluoro-6-(1-methyl-1H-pyrazol-4-yl)-[1,2,4]triazolo[4,3-a]pyridine-3-yl)thio)-4-methoxy-3-(1-methyl-1H-pyrazol-4-yl)quinoline 40 (3 mg) as a white solid.

MS m/z (ESI): 487.2

$^1$H NMR (400 MHz, DMSO-d$_6$, ppm): δ 9.23 (s, 1H), 8.68 (s, 1H), 8.44 (s, 2H), 8.16 (s, 1H), 8.14 (s, 1H), 8.13 (s, 1H), 8.01 (d, J=8.8 Hz, 1H), 7.92 (d, J=12 Hz, 1H), 7.60 (d, J=8.8 Hz, 1H), 3.99 (s, 3H), 3.90 (s, 3H), 3.84 (s, 3H).

Example 41

4-fluoro-3-(1-methyl-1H-pyrazol-4-yl)-6-((6-(1-methyl-1H-pyrazol-4-yl)-[1,2,4]triazolo[4,3-a]pyridin-3-yl)thio)quinoline (41)

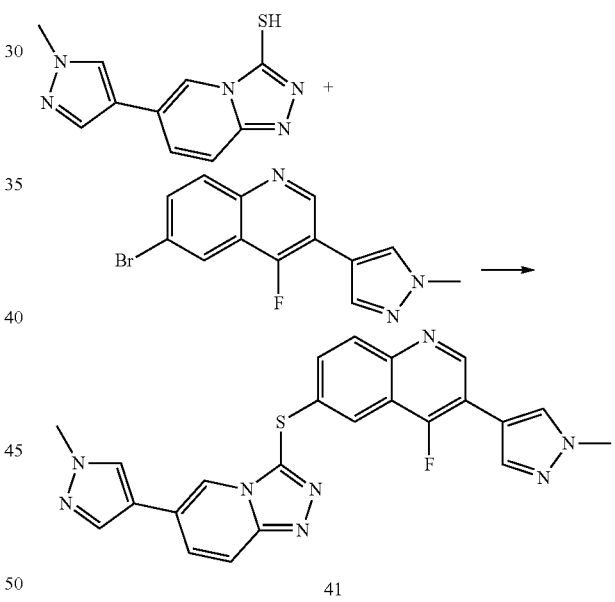

6-(1-methyl-1H-pyrazol-4-yl)-[1,2,4]triazolo[4,3-a]pyridin-3-thiol (76 mg, 0.33 mmol), 6-bromo-4-fluoro-3-(1-methyl-1H-pyrazol-4-yl)quinoline (100 mg, 0.33 mmol), tris(dibenzylideneacetone)dipalladium (30 mg, 0.033 mmol), 4,5-bis(diphenylphosphino)-9,9-dimethylxanthene (38 mg, 0.066 mmol) and N,N-diisopropylethylamine (169 mg, 1.31 mmol) were dissolved in anhydrous N,N-dimethylformamide (2 mL) under N$_2$. The reaction mixture was heated to 100° C. and stirred for 16 hours, and then concentrated to dryness under reduced pressure. The crude product was separated by column chromatography (dichloromethane/methanol=25:1, v/v) to obtain a solid, and then the solid was purified by reverse phase column chromatography to give 4-fluoro-3-(1-methyl-1H-pyrazol-4-yl)-6-((6-(1-methyl-1H-pyrazol-4-yl)-[1,2,4]triazolo[4,3-a]pyridin-3- yl)thio)quinoline 41 (30 mg, yield 20%) as a pale yellow solid.

MS m/z (ESI): 457.1

$^1$H NMR (400 MHz, DMSO-d$_6$, ppm): δ 9.26 (d, J=10.0 Hz, 1H), 8.68 (s, 1H), 8.41 (s, 1H), 8.36 (s, 1H), 8.12 (s, 1H), 7.99-8.05 (m, 3H), 7.93 (s, 1H), 7.84 (d, J=9.6 Hz, 1H), 7.56 (d, J=9.0 Hz, 1H), 3.94 (s, 3H), 3.85 (s, 3H).

Example 42

4-(4-fluoro-6-((8-fluoro-6-(1-methyl-1H-pyrazol-4-yl)-[1,2,4]triazolo[4,3-a]pyridin-3-yl)thio)quinolin-3-yl)morpholine (42)

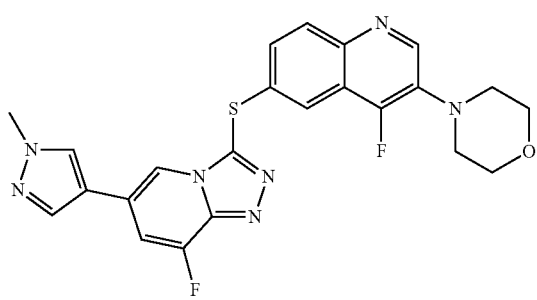

42

8-fluoro-6-(1-methyl-1H-pyrazol-4-yl)-[1,2,4]triazolo[4,3-a]pyridin-3-thiol (55 mg, 0.22 mmol), 4-(6-bromo-4-fluoroquinolin-3-yl)morpholine (69 mg, 0.22 mmol), tris(dibenzylideneacetone)dipalladium (20 mg, 0.022 mmol), 4,5-bis(diphenylphosphino)-9,9-dimethylxanthene (26 mg, 0.044 mmol) and N,N-diisopropylethylamine (114 mg, 0.88 mmol) were dissolved in anhydrous N,N-dimethylformamide (2 mL) under N$_2$, the reaction mixture was heated to 100° C. and stirred for 16 hours, and then concentrated to dryness under reduced pressure. The crude product was separated by column chromatography (dichloromethane/methanol=25:1, v/v) to obtain a solid, and then the solid was purified by reverse phase column chromatography to give 4-(4-fluoro-6-((8-fluoro-6-(1-methyl-1H-pyrazol-4-yl)-[1,2,4]triazolo[4,3-a]pyridin-3-yl)thio)quinolin-3-yl)morpholine 42 (1.5 mg) as a white solid.

MS m/z (ESI): 480.1.

$^1$H NMR (400 MHz, CDCl$_3$, ppm): δ 8.61 (d, J=10.4 Hz, 1H), 7.98 (s, 1H), 7.86 (s, 2H), 7.60 (s, 1H), 7.54 (s, 1H), 7.38 (d, J=8.8 Hz, 1H), 7.11 (d, J=10.4 Hz, 1H), 3.89 (s, 3H), 3.83 (t, J=4.4 Hz, 4H), 3.23 (t, J=4.4 Hz, 4H).

Example 43

(4-chloro-6-((6-(1-methyl-1H-pyrazol-4-yl)-[1,2,4]triazolo[4,3-a]pyridin-3-yl)thio)quinolin-3-yl)(morpholino)methanone (43)

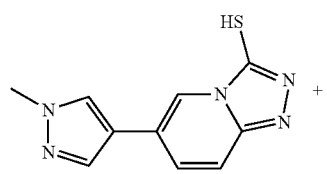

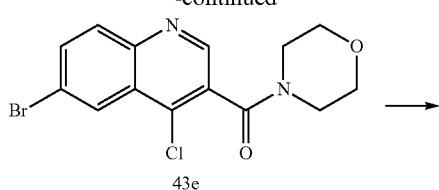

43e

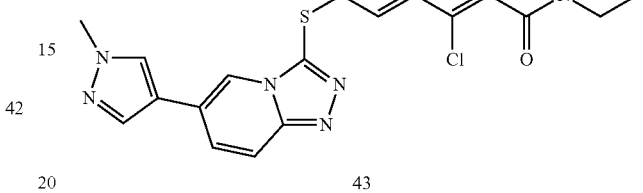

43

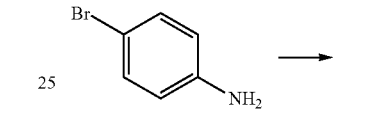

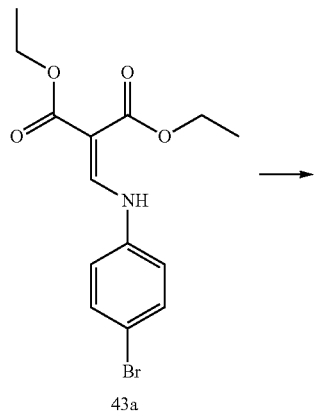

43a

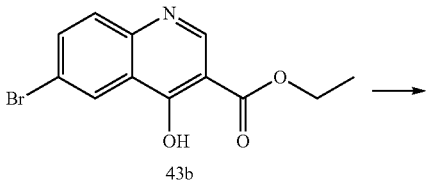

43b

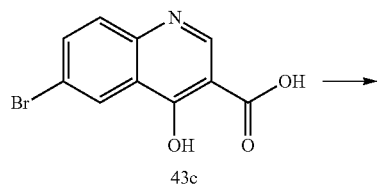

43c

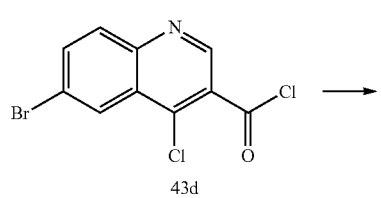

43d

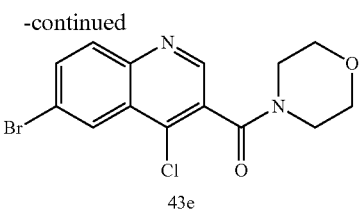

43e

Step 1: diethyl 2-(((4-bromophenyl)amino)methylene)malonate 43a 4-bromoaniline (50 g, 290.7 mmol) and diethyl 2-(ethoxymethylene)malonate (63.5 g, 293.7 mmol) were placed in a 500 mL round bottom flask, and the reaction mixture was heated to 90° C. for 5 hours. The reaction mixture was mixed with 200 mL ethanol slowly, and cooled to room temperature. The precipitated solid was collected by filtration and washed with cold ethanol, and then dried to give diethyl 2-(((4-bromophenyl)amino)methylene)malonate (85.7 g, yield 86%) as a white solid.

MS m/z (ESI): 342.0

Step 2: ethyl 6-bromo-4-hydroxyquinoline-3-carboxylate 43b

Diethyl 2-(((4-bromophenyl)amino)methylene)malonate (85.7 g, 250.0 mmol) was added to hot diphenyl ether (130 mL) in batches. After the addition was completed, the reaction mixture was heated to 232° C. for 5 hours, and then cooled to 100° C., and ethanol (200 mL) was added slowly. The reaction mixture was kept at this temperature and stirred for about 10 minutes, and then cooled to room temperature. The precipitated solid was collected by filtration and washed with diethyl ether, and then dried to give ethyl 6-bromo-4-hydroxy quinoline-3-carboxylate (59.6 g, 80%) as a white solid.

MS m/z (ESI): 296.0

$^1$H NMR (400 MHz, DMSO-$d_6$, ppm): δ 12.47 (s, 1H), 8.60 (s, 1H), 8.23 (s, 1H), 7.87 (dd, J=8.8, 2.0 Hz, 1H), 7.61 (d, J=8.4 Hz, 1H), 4.23 (q, 2H), 1.28 (t, J=7.2 Hz, 3H).

Step 3: 6-bromo-4-hydroxyquinoline-3-carboxylic acid 43c

Ethyl 6-bromo-4-hydroxyquinoline-3-carboxylate (59.6 g, 201.0 mmol) was dispersed in ethanol (600 mL), and sodium hydroxide aqueous solution (24.1 g, 604.0 mmol, 200 mL) was added. The reaction mixture was heated to 50° C. for 5 hours and then cooled to room temperature. The insoluble solid was removed by filtration, the filtrate was neutralized with 3N hydrochloric acid, the precipitated solid was collected by filtration and washed with water, and then dried to give 6-bromo-4-hydroxyquinoline-3-carboxylic acid (52.8 g, yield 98%) as a white solid.

MS m/z (ESI): 368.0

Step 4: 6-bromo-4-chloroquinoline-3-carbonyl chloride 43d 6-bromo-4-hydroxyquinoline-3-carboxylic acid (1.00 g, 3.730 mmol) was placed in phosphorous oxychloride (20 mL), and the reaction mixture was heated to 100° C. for 16 hours. The reaction mixture was distilled under reduced pressure to remove the excess phosphorus oxychloride, the residue was co-boiled with toluene to remove a little remaining phosphorus oxychloride. The crude product 6-bromo-4-chloroquinoline-3-carbonyl chloride was used directly in the next step.

Step 5: (6-bromo-4-chloroquinolin-3-yl)(morpholino)methanone 43e

Morpholine (488 mg, 5.61 mmol) and triethylamine (1.13 g, 11.21 mmol) were dissolved in dichloromethane (30 mL). 6-bromo-4-chloroquinoline-3-carbonyl chloride (1.14 g, 3.74 mmol) was added in batches at 0° C. After addition was completed, the reaction solution was kept at this temperature for 2 hours. Then, the reaction solution was concentrated to a small volume, the precipitated solid was collected by filtration and washed with water, and then dried to give (6-bromo-4-chloro-quinolin-3-yl) (morpholino)methanone (508 mg, yield 38%) as a yellow solid.

MS m/z (ESI): 357.0

$^1$H NMR (400 MHz, DMSO-$d_6$, ppm): δ 8.91 (s, 1H), 8.43 (s, 1H), 8.09 (s, 2H), 3.69-3.76 (m, 4H), 3.53-3.57 (m, 2H), 3.24-3.26 (m, 2H).

Step 6: (4-chloro-6-((6-(1-methyl-1H-pyrazol-4-yl)-[1,2,4]triazolo[4,3-a]pyridin-3-yl)thio)quinolin-3-yl) (morpholino)methanone (43)

6-(1-methyl-1H-pyrazol-4-yl)-[1,2,4]triazolo[4,3-a]pyridin-3-thiol (330 mg, 1.43 mmol), (6-bromo-4-chloro-quinolin-3-yl)(morpholino)methanone (508 mg, 1.43 mmol), tris (dibenzylideneacetone)dipalladium (131 mg, 0.143 mmol), 4,5-bis(diphenylphosphino)-9,9-dimethylxanthene (165 mg, 0.29 mmol) and N,N-diisopropylethylamine (737 mg, 5.71 mmol) were dissolved in anhydrous 1,4-dioxane (5 mL) under $N_2$, and the reaction mixture was heated to 85° C. and stirred for 16 hours and concentrated to dryness under reduced pressure. The resulting residue was purified by column chromatography (dichloromethane/methanol=25:1, v/v), and then recrystallized to give (4-chloro-6-((6-(1-methyl-1H-pyrazol-4-yl)-[1,2,4]triazolo[4,3-a]pyridin-3-yl) thio)quinolin-3-yl)(morpholino)methanone 43 (332 mg, yield 46%) as a yellow solid.

MS m/z (ESI): 506.1

$^1$H NMR (400 MHz, DMSO-$d_6$, ppm): δ 8.82 (s, 1H), 8.69 (s, 1H), 8.36 (s, 1H), 8.02-8.09 (m, 4H), 7.85 (d, J=9.6 Hz, 1H), 7.68 (d, J=8.8 Hz, 1H), 3.86 (s, 3H), 3.66-3.73 (m, 4H), 3.49-3.52 (m, 2H), 3.19-3.21 (m, 2H).

Example 44

4-(4-chloro-6-((6-(1-methyl-1H-pyrazol-4-yl)-[1,2,4]triazolo[4,3-a]pyridin-3-yl)thio)quinolin-3-yl)morpholine (44)

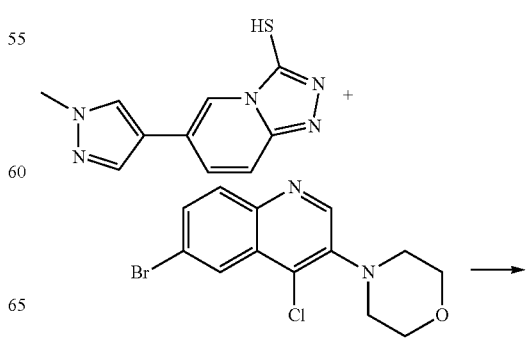

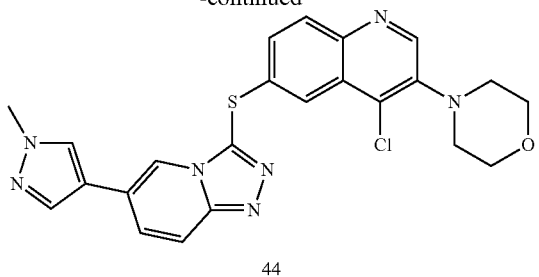

44

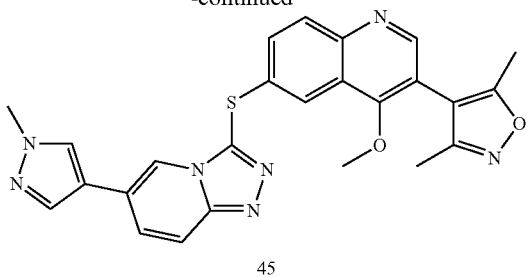

45

6-(1-methyl-1H-pyrazol-4-yl)-[1,2,4]triazolo[4,3-a]pyridin-3-thiol (100 mg, 0.43 mmol), 4-(6-bromo-4-chloro-quinolin-3-yl)morpholine (145 mg, 0.43 mmol), tris(dibenzylideneacetone)dipalladium (40 mg, 0.043 mmol), 4,5-bis(diphenylphosphino)-9,9-dimethylxanthene (50 mg, 0.086 mmol) and N,N-diisopropylethylamine (223 mg, 1.73 mmol) were dissolved in anhydrous N,N-dimethylformamide (5 mL) under $N_2$, the reaction mixture was heated to 90° C. and stirred for 16 h, and concentrated to dryness under reduced pressure. The resulting residue was purified by column chromatography (dichloromethane/methanol=25:1, v/v), and then further purified by reverse phase column chromatography to give 4-(4-chloro-6-((6-(1-methyl-1H-pyrazol-4-yl)-[1,2,4]triazolo[4,3-a]pyridin-3-yl)thio)quinolin-3-yl)morpholine 44 (20 mg, yield 10%) as a pale yellow solid.

MS m/z (ESI): 477.9.

$^1$H NMR (400 MHz, DMSO-$d_6$, ppm): δ 8.82 (s, 1H), 8.67 (s, 1H), 8.36 (s, 1H), 8.04 (s, 1H), 8.03 (d, J=9.6 Hz, 1H), 7.98 (s, 1H), 7.97 (d, J=8.8 Hz, 1H), 7.84 (d, J=9.6 Hz, 1H), 7.46 (d, J=8.8 Hz, 1H), 3.85 (s, 3H), 3.78 (t, J=4.0 Hz, 4H), 3.22 (t, J=4.0 Hz, 4H).

Example 45

4-(4-methoxy-6-((6-(1-methyl-1H-pyrazol-4-yl)[1,2,4]triazolo[4,3-a]pyridin-3-yl)thio)quinolin-3-yl)-3,5-dimethylisoxazole (45)

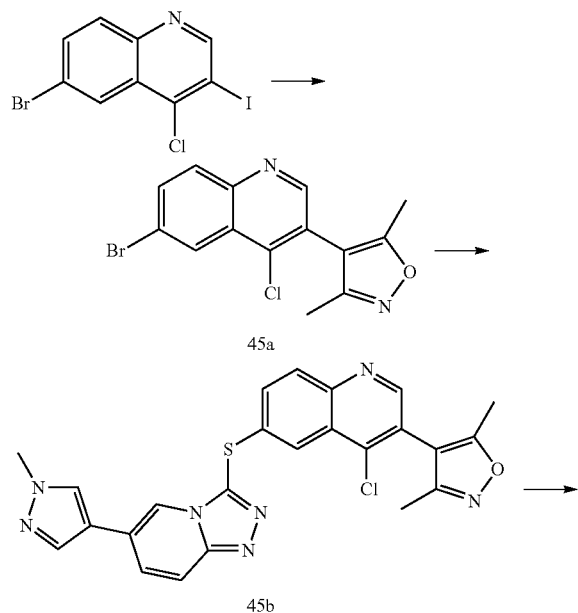

Step 1: 4-(6-bromo-4-chloroquinolin-3-yl)-3,5-dimethylisoxazole 45a 6-bromo-4-chloro-3-iodoquinoline (300 mg, 0.81 mmol), (3,5-dimethylisothiazol-4-yl)boronic acid (276 mg, 1.95 mmol), [1,1'-bis(diphenylphosphino)ferrocene]dichloropalladium (60 mg, 0.081 mmol) and potassium carbonate (338 mg, 2.44 mmol) were dissolved in a mixed solvent of 1,4-dioxane (5 mL) and water (1 mL), the reaction mixture was heated to 35° C. for 16 hours and concentrated to dryness under reduced pressure. The resulting residue was dissolved in ethyl acetate, and then washed with sodium chloride aqueous solution, dried, filtered and concentrated to obtain a crude product, and then the crude product was purified by column chromatography (petroleum ether/ethyl acetate=3:1, v/v) to give 4-(6-bromo-4-chloroquinolin-3-yl)-3,5-dimethylisoxazole (200 mg, yield 73%) as a colorless oil.

MS m/z (ESI): 339.0

Step 2: 4-(4-chloro-6-((6-(1-methyl-1H-pyrazol-4-yl)-[1,2,4]triazolo[4,3-a]pyridin-3-yl)thio)quinolin-3-yl)-3,5-dimethylisoxazole 45b 6-(1-methyl-1H-pyrazol-4-yl)-[1,2,4]triazolo[4,3-a]pyridin-3-thiol (137 mg, 0.59 mmol), 4-(6-bromo-4-chloroquinolin-3-yl)-3,5-dimethylisoxazole (200 mg, 0.59 mmol), tris(dibenzylideneacetone)dipalladium (54 mg, 0.059 mmol), 4,5-bis(diphenylphosphino)-9,9-dimethylxanthene (69 mg, 0.12 mmol) and N,N-diisopropylethylamine (306 mg, 2.37 mmol) were dissolved in anhydrous 1,4-dioxane (5 mL) under $N_2$, and the reaction mixture was heated to 75° C. and stirred for 16 hours. The reaction solution was concentrated to dryness under reduced pressure. The crude product was purified by column chromatography (dichloromethane/methanol=25:1, v/v) to give 4-(4-chloro-6-((6-(1-methyl-1H-pyrazol-4-yl)-[1,2,4]triazolo[4,3-a]pyridin-3-yl)thio)quinolin-3-yl)-3,5-dimethylisoxazole (140 mg, yield 48%) as a yellow solid.

MS m/z (ESI): 488.1

Step 3: 4-(4-methoxy-6-((6-(1-methyl-1H-pyrazol-4-yl)-[1,2,4]triazolo[4,3-a]pyridin-3-yl)thio)quinolin-3-yl)-3,5-dimethylisoxazole 45

4-(4-chloro-6-((6-(1-methyl-1H-pyrazol-4-yl)-[1,2,4]triazolo[4,3-a]pyridin-3-yl)thio)quinolin-3-yl)-3,5-dimethylisoxazole (140 mg, 0.2869 mmol) and sodium methoxide (77 mg, 1.434 mmol) were dissolved in methanol (5 mL). The reaction mixture was heated to 75° C. and stirred for 16 hours, and then concentrated to dryness under reduced pressure. The residue was dissolved with ethyl acetate, and then washed with sodium chloride aqueous solution, dried, filtered and concentrated to obtain a crude product, and then the crude product was purified by reverse phase column chromatography to give 4-(4-methoxy-6-((6-(1-methyl-1H-pyrazol-4-yl)-[1,2,4]triazolo[4,3-a]pyridin-3-yl)thio)quinolin-3-yl)-3,5-dimethylisoxazole 45 (100 mg, yield 72%) as a white solid.

MS m/z (ESI): 484.0

$^1$H NMR (400 MHz, DMSO-$d_6$, ppm): δ 8.69 (s, 2H), 8.36 (s, 1H), 8.10 (s, 1H), 8.05 (s, 1H), 8.02 (d, J=8.8 Hz, 1H), 8.00 (d, J=8.8 Hz, 1H), 7.83 (d, J=9.6 Hz, 1H), 7.61 (d, J=8.8 Hz, 1H), 3.85 (s, 3H), 3.59 (s, 3H), 2.34 (s, 3H), 2.15 (s, 3H).

Example 46

3-(benzo[d][1,3]dioxol-5-yl)-4-methoxy-6-((6-(1-methyl-1H-pyrazol-4-yl)-[1,2,4]triazolo[4,3-a]pyridin-3-yl)thio)quinoline (46)

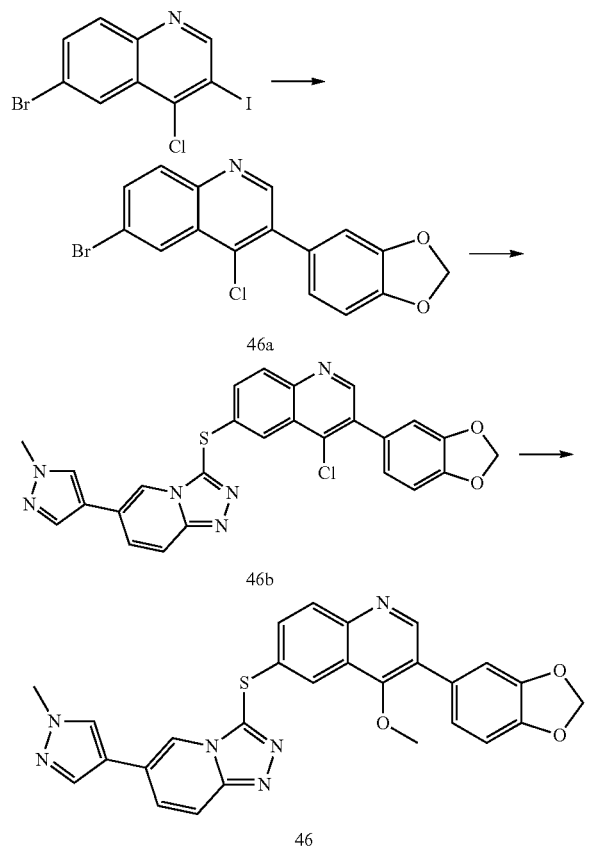

Step 1: 3-(benzo[d][1,3]dioxol-5-yl)-6-bromo-4-chloroquinoline 46a 6-bromo-4-chloro-3-iodoquinoline (300 mg, 0.81 mmol), benzo[d][1,3]dioxazole-5-ylboronic acid (149 mg, 0.90 mmol), [1,1'-bis(diphenylphosphino)ferrocene]dichloropalladium (60 mg, 0.081 mmol) and potassium carbonate (338 mg, 2.44 mmol) were dissolved in a mixed solvent of 1,4-dioxane (4 mL) and water (0.5 mL). The reaction solution was heated to 35° C. for 16 hours. The precipitated solid was collected by filtration and washed with water, and then dried to give 3-(benzo[d][1,3]dioxol-5-yl)-6-bromo-4-chloroquinoline (272 mg, yield 92%) as a white solid.

MS m/z (ESI): 363.9

Step 2: 3-(benzo[d][1,3]dioxol-5-yl)-4-chloro-6-((6-(1-methyl-1H-pyrazol-4-yl)-[1,2,4]triazolo[4,3-a]pyridin-3-yl)thio)quinoline 46b 6-(1-methyl-1H-pyrazol-4-yl)-[1,2,4]triazolo[4,3-a]pyridin-3-thiol (100 mg, 0.43 mmol), 3-(benzo[d][1,3]dioxazol-5-yl)-6-bromine-4-chloroquinoline (157 mg, 0.43 mmol), tris(dibenzylideneacetone)dipalladium (40 mg, 0.043 mmol), 4,5-bis(diphenylphosphino)-9,9-dimethylxanthene (50 mg, 0.086 mmol) and N,N-diisopropylethylamine (223 mg, 1.73 mmol) were dissolved in anhydrous 1,4-dioxane (5 mL) under $N_2$, the reaction mixture was heated to 75° C. and stirred for 16 hours, and then concentrated to dry under reduced pressure. The crude product was purified by column chromatography (dichloromethane/methanol=25:1, v/v) to give 3-(benzo[d][1,3]dioxol-5-yl)-4-chloro-6-((6-(1-methyl-1H-pyrazol-4-yl)-[1,2,4]triazolo[4,3-a]pyridin-3-yl)thio)quinoline (173 mg, yield 78%) as a pale yellow solid.

MS m/z (ESI): 513.1

Step 3: 3-(benzo[d][1,3]dioxol-5-yl)-4-methoxy-6-((6-(1-methyl-1H-pyrazol-4-yl)-[1,2,4]triazolo[4,3-a]pyridin-3-yl)thio)quinoline 46

3-(benzo[d][1,3]dioxol-5-yl)-4-chloro-6-((6-(1-methyl-1H-pyrazol-4-yl)-[1,2,4]triazolo[4,3-a]pyridin-3-yl)thio)quinoline (173 mg, 0.34 mmol) and sodium methoxide (91 mg, 1.69 mmol) were dissolved in methanol (5 mL). The reaction mixture was heated to 75° C. for 16 hours, and then concentrated to dryness under reduced pressure. The crude product was purified by column chromatography (dichloromethane/methanol=25:1, v/v), pulverized, filtered, and dried to give 3-(benzo[d][1,3]dioxol-5-yl)-4-methoxy-6-((6-(1-methyl-1H-pyrazol-4-yl)-[1,2,4]triazolo[4,3-a]pyridin-3-yl)thio)quinoline 46 (100 mg, yield 58%) as a white solid.

MS m/z (ESI): 508.9.

$^1$H NMR (400 MHz, DMSO-$d_6$, ppm): δ 8.77 (s, 1H), 8.67 (s, 1H), 8.35 (s, 1H), 8.06 (d, J=2.0 Hz, 1H), 8.04 (s, 1H), 8.01 (d, J=9.2 Hz, 1H), 7.97 (d, J=8.8 Hz, 1H), 7.82 (d, J=9.2 Hz, 1H), 7.58 (d, J=8.8, 2.0 Hz, 1H), 7.20 (s, 1H), 7.05-7.11 (m, 2H), 6.10 (s, 2H), 3.85 (s, 3H), 3.56 (s, 3H).

Example 47

1-(4-(4-methoxy-6-((6-(1-methyl-1H-pyrazol-4-yl)-[1,2,4]triazolo[4,3-a]pyridin-3-yl)thio)quinolin-3-yl)piperazin-1-yl)ethan-1-one (47)

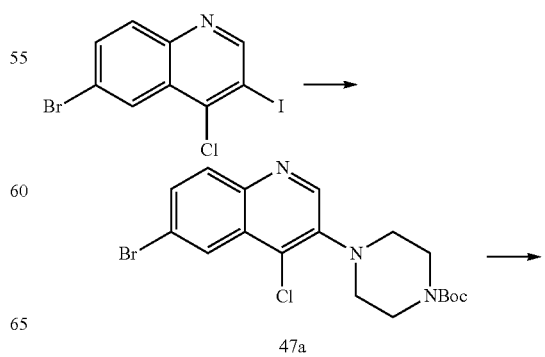

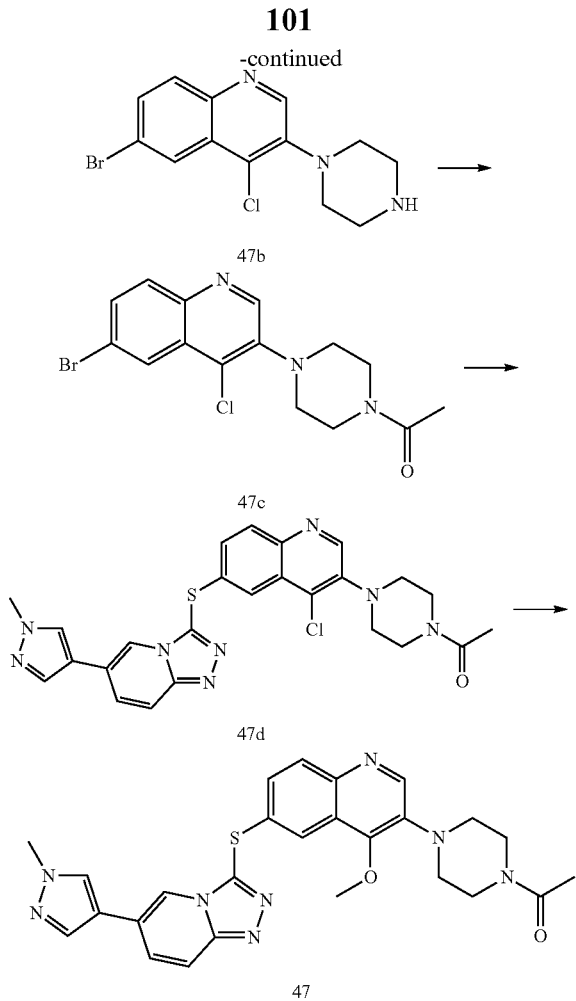

Step 1: tert-butyl 4-(6-bromo-4-chloroquinolin-3-yl)piperazine-1-carboxylate 47a 6-bromo-4-chloro-3-iodoquinoline (1.00 g, 2.714 mmol), tert-butylpiperazine-1-carboxylate (605 mg, 3.26 mmol), tris(dibenzylideneacetone)dipalladium (250 mg, 0.27 mmol) and 4,5-bis(diphenylphosphino)-9,9-dimethylxanthene (315 mg, 0.54 mmol) were dissolved in anhydrous N,N-dimethylformamide (50 mL) under N$_2$, the reaction mixture was heated to 35° C. and stirred for 1 hour, and then sodium tert-butoxide (315 mg, 3.26 mmol) was added. The reaction mixture was kept at this temperature for 16 hours and concentrated to dryness under reduced pressure. The crude product was purified by column chromatography (dichloromethane/methanol=25:1, v/v) to give tert-butyl 4-(6-bromo-4-chloroquinolin-3-yl)piperazine-1-carboxylate (0.98 g, yield 85%) as a brown oil.

MS m/z (ESI): 428.0

Step 2: 6-bromo-4-chloro-3-(piperazin-1-yl)quinoline 47b

Tert-butyl 4-(6-bromo-4-chloroquinolin-3-yl)piperazine-1-carboxylate (0.98 g, 2.30 mmol) was dissolved in dichloromethane (3 mL) and trifluoroacetic acid (1 mL), and the reaction mixture was stirred at room temperature for 30 minutes. The reaction mixture was concentrated to dryness under reduced pressure to give a crude product 6-bromo-4-chloro-3-(piperazin-1-yl)quinolone, which was used directly in the next step.

MS m/z (ESI): 328.0

Step 3: 1-(4-(6-bromo-4-chloroquinolin-3-yl)piperazin-1-yl)ethan-1-one 47c 6-bromo-4-chloro-3-(piperazin-1-yl)quinoline (200 mg, 0.6124 mmol) and triethylamine (186 mg, 1.84 mmol) were added to dichloromethane (2 mL). Acetyl chloride (58 mg, 0.74 mmol) was added dropwise at 0° C. After the addition was completed, the reaction mixture was stirred at room temperature for 1 hour. The reaction solution was concentrated to dryness under reduced pressure, and the crude product was purified by column chromatography (dichloromethane/methanol=25:1, v/v) to give 1-(4-(6-bromo-4-chloroquinolin-3-yl)piperazin-1-yl)ethan-1-one (88 mg, yield 39%) as a pale yellow solid.

MS m/z (ESI): 370.0

Step 4: 1-(4-(4-chloro-6-((6-(1-methyl-1H-pyrazol-4-yl)-[1,2,4]triazolo[4,3-a]pyridin-3-yl)thio)quinolin-3-yl)piperazin-1-yl)ethan-1-one 47d 6-(1-methyl-1H-pyrazol-4-yl)-[1,2,4]triazolo[4,3-a]pyridin-3-thiol (55 mg, 0.24 mmol), 1-(4-(6-bromine-4-chloroquinolin-3-yl)piperazin-1-yl)ethanone (88 mg, 0.24 mmol), tris(dibenzylideneacetone)dipalladium (22 mg, 0.024 mmol), 4,5-bis(diphenylphosphino)-9,9-dimethylxanthene (28 mg, 0.048 mmol) and N,N-diisopropylethylamine (123 mg, 0.95 mmol) were dissolved in anhydrous 1,4-dioxane (2 mL) under N$_2$, the reaction mixture was heated to 75° C. and stirred for 16 h, and then concentrated to dryness under reduced pressure. The crude product was purified by column chromatography (dichloromethane/methanol=25:1, v/v) to give 1-(4-(4-chloro-6-((6-(1-methyl-1H-pyrazol-4-yl)-[1,2,4]triazolo[4,3-a]pyridin-3-yl)thio)quinolin-3-yl)piperazin-1-yl)ethan-1-one (58 mg, yield 47%) as a pale yellow solid.

MS m/z (ESI): 519.1

Step 5: 1-(4-(4-methoxy-6-((6-(1-methyl-1H-pyrazol-4-yl)-[1,2,4]triazolo[4,3-a]pyridin-3-yl)thio)quinolin-3-yl)piperazin-1-yl)ethan-1-one 47

1-(4-(4-chloro-6-((6-(1-methyl-1H-pyrazol-4-yl)-[1,2,4]triazolo[4,3-a]pyridin-3-yl)thio)quinolin-3-yl)piperazin-1-yl)ethan-1-one (58 mg, 0.11 mmol) and sodium methoxide (30 mg, 0.56 mmol) were dissolved in methanol (2 mL). The reaction mixture was heated to 75° C. for 16 hours, and then concentrated to dryness under reduced pressure. The crude product was purified by column chromatography (dichloromethane/methanol=25:1, v/v), pulverized, filtered, and dried to give 1-(4-(4-methoxy-6-((6-(1-methyl-1H-pyrazol-4-yl)-[1,2,4]triazolo[4,3-a]pyridin-3-yl)thio)quinolin-3-yl)piperazin-1-yl)ethan-1-one 47 (10 mg, yield 18%) as a pale yellow solid.

MS m/z (ESI): 515.0

$^1$H NMR (400 MHz, DMSO-d$_6$, ppm): δ 8.70 (s, 1H), 8.64 (s, 1H), 8.34 (s, 1H), 8.03 (s, 1H), 8.01 (d, J=9.6 Hz, 1H), 7.92 (d, J=2.0 Hz, 1H), 7.87 (d, J=8.4 Hz, 1H), 7.82 (d, J=9.6 Hz, 1H), 7.40 (dd, J=8.8 Hz, J=2.4 Hz, 1H), 3.94 (s, 3H), 3.85 (s, 3H), 3.62-3.64 (m, 4H), 3.18-3.20 (m, 2H), 3.12-3.14 (m, 2H), 2.05 (s, 3H).

Example 48

2-(4-(4-methoxy-6-((6-(1-methyl-1H-pyrazol-4-yl)-[1,2,4]triazolo[4,3-a]pyridin-3-yl)thio)quinolin-3-yl)-1H-pyrazol-1-yl)ethan-1-ol (48)

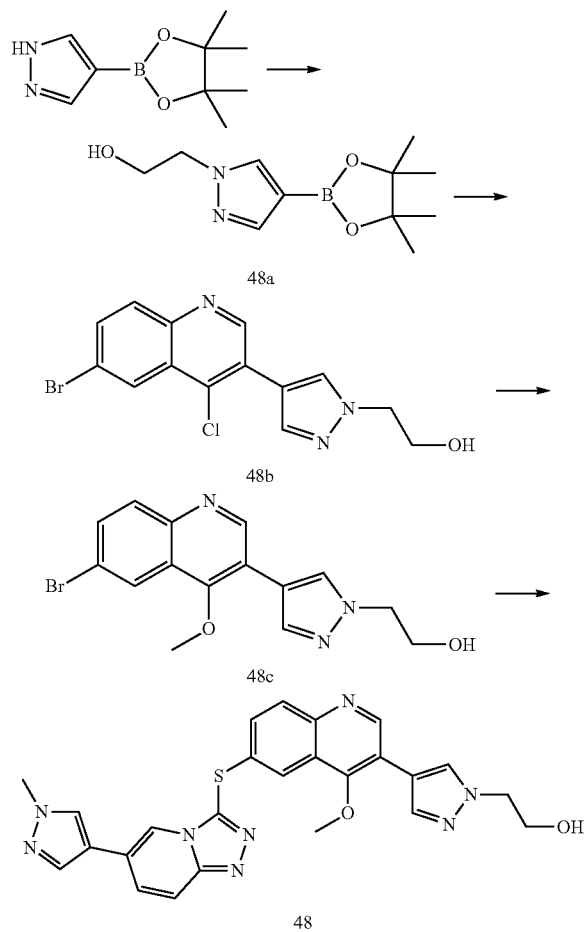

Step 1: 2-(4-(4,4,5,5-tetramethyl-1,3,2-dioxaborolan-2-yl)-1H-pyrazol-1-yl)ethan-1-ol 48a 4-(4,4,5,5-tetramethyl-1,3,2-dioxaborolan-2-yl)-1H-pyrazole (1.00 g, 5.15 mmol), ethylene carbonate (500 mg, 5.670 mmol) and sodium hydride (206 mg, 5.16 mmol) were dissolved in N,N-dimethylformamide (10 mL). The reaction mixture was heated to 160° C. for 2 hours, cooled to room temperature, and then activated carbon was added. The reaction mixture was stirred for another 1 hour, filtered, and washed with N,N-dimethylformamide. The filtrate was concentrated to give a crude product 2-(4-(4,4,5,5-tetramethyl-1,3,2-dioxaborolan-2-yl)-1H-pyrazol-1-yl)ethan-1-ol, which was used directly in the next step.

MS m/z (ESI): 239.1

Step 2: 2-(4-(6-bromo-4-chloroquinolin-3-yl)-1H-pyrazol-1-yl)ethan-1-ol 48b 6-bromo-4-chloro-3-iodoquinoline (155 mg, 0.42 mmol), 2-(4-(4,4,5,5-tetramethyl-1,3,2-dioxaborolan-2-yl)-1H-pyrazol-1-yl)ethan-1-ol (220 mg, 0.46 mmol), [1,1'-bis(diphenylphosphino)ferrocene]dichloropalladium (31 mg, 0.042 mmol) and potassium carbonate (174 mg, 1.26 mmol) were dissolved in a mixture of 1,4-dioxane (4 mL) and water (1 mL). The reaction mixture was heated to 35° C. for 16 hours and then concentrated to dryness under reduced pressure. The residue was purified by column chromatography (dichloromethane/methanol=20:1, v/v) to give 2-(4-(6-bromo-4-chloroquinolin-3-yl)-1H-pyrazol-1-yl)ethan-1-ol (165 mg, yield 89%) as an off-white solid.

MS m/z (ESI): 354.0

Step 3: 2-(4-(6-bromo-4-methoxyquinolin-3-yl)-1H-pyrazol-1-yl)ethan-1-ol 48c 2-(4-(6-bromo-4-chloroquinolin-3-yl)-1H-pyrazol-1-yl)ethan-1-ol (100 mg, 0.2836 mmol) and sodium methoxide (77 mg, 1.418 mmol) were dissolved in methanol (2 mL). The reaction mixture was heated to 65° C. for 16 hours and then concentrated to dryness under reduced pressure. The crude product was purified by column chromatography (dichloromethane/methanol=25:1, v/v) to give 2-(4-(6-bromo-4-methoxyquinolin-3-yl)-1H-pyrazol-1-yl)ethan-1-ol (53 mg, yield 54%) as a white solid.

MS m/z (ESI): 348.0

Step 4: 2-(4-(4-methoxy-6-((6-(1-methyl-1H-pyrazol-4-yl)-[1,2,4]triazolo[4,3-a]pyridin-3-yl)thio)quinolin-3-yl)-1H-pyrazol-1-yl)ethan-1-ol 48

6-(1-methyl-1H-pyrazol-4-yl)-[1,2,4]triazolo[4,3-a]pyridin-3-thiol (35 mg, 0.15 mmol), 2-(4-(6-bromo-4-methoxyquinolin-3-yl)-1H-pyrazol-1-yl)ethan-1-ol (53 mg, 0.15 mmol), tris(dibenzylideneacetone)dipalladium (14 mg, 0.015 mmol), 4,5-bis(diphenylphosphino)-9,9-dimethylxanthene (18 mg, 0.030 mmol) and N,N-diisopropylethylamine (28 mg, 0.61 mmol) were dissolved in anhydrous N,N-dimethylformamide (2 mL) under $N_2$, the reaction mixture was heated to 90° C. and stirred for 16 hours, and then concentrated to dryness under reduced pressure. The crude product was purified by column chromatography (dichloromethane/methanol=25:1, v/v), and then further purified by reverse phase column chromatography to give 2-(4-(4-methoxy-6-((6-(1-methyl-1H-pyrazol-4-yl)-[1,2,4]triazolo[4,3-a]pyridin-3-yl)thio)quinolin-3-yl)-1H-pyrazol-1-yl)ethan-1-ol 48 (30 mg, yield 40%) as a white solid.

MS m/z (ESI): 498.9

$^1$H NMR (400 MHz, DMSO-$d_6$, ppm): δ 9.17 (s, 1H), 8.69 (s, 1H), 8.37 (s, 1H), 8.34 (s, 1H), 8.12 (s, 1H), 8.03 (s, 1H), 8.02 (d, J=9.6 Hz, 1H), 7.96 (d, J=8.8 Hz, 1H), 7.93 (d, J=2.4 Hz, 1H), 7.82 (d, J=9.2 Hz, 1H), 7.51 (dd, J=8.8, 2.0 Hz, 1H), 4.94 (t, J=5.6 Hz, 1H), 4.23 (t, J=5.6 Hz, 2H), 3.84 (s, 3H), 3.76-3.80 (m, 2H), 3.73 (s, 3H).

Biological Evaluation

Experimental Example 1

Experimental Purpose:

The purpose is to study the effect of the compounds on c-MET tyrosine kinase activity at the molecular level. $IC_{50}$ values were calculated from the data of the inhibition rates of the compounds on c-MET tyrosine kinase phosphorylation at various concentrations, thereby evaluating the compounds.

Experimental Method:

1. The positive control and the test compounds were first dissolved in 100% dimethyl sulfoxide to prepare a 20 mM stock solution, which was stored at −20° C. in a freezer.

2. Just before the experiment, the above stock solution was diluted to a final concentration of 4% in dimethyl sulfoxide.

3. 5× kinase buffer was diluted with water to 1.33× kinase buffer.

4. A mixture of 4 μmol/L polypeptide substrate and 2× kinase was prepared in 1.33× kinase buffer.

5. 4 μmol/L phosphorylated peptide substrates were prepared in 1.33× kinase buffer.

6. Appropriate concentration of ATP was prepared in 1.33× kinase buffer.

7. According to the need of dilution ratio, endonuclease was diluted in display buffer B.

8. All of the compounds were diluted within a 96-well plate.

9. The mixture of 4 μmol/L polypeptide substrate and 2× kinase, and the 4× ATP solution were added to a 96-well plate, and the reagents were then transferred to a 384-well plate by a 12 channel pipettor.

10. The plate was incubated at room temperature for 1 hour.

11. 5 μL display buffer were added, and the plate was incubated at room temperature for another 1 hour.

12. Fluorescence was read on a NovoStar microplate reader, with excitation wavelength: 400 nm, and emission wavelength: 445 nm and 520 nm.

13. Using GraphPad software, a non-linear regression curve was generated based on the inhibition ratio as a function of the concentration of the compounds. The IC50 was calculated using a S-shaped dose-effect curve fitting. The inhibition rates of the compounds were calculated according to the following formula.

14. Emission light wave ratio=(Coumarin emission wave 445 nm)÷(Fluorescein emission wave 520 nm)

15. Inhibition percent=1−phosphorylation (absorption) %/phosphorylation (divergence) %

Experimental Results:

The enzyme activity test at the molecular level showed that [1,2,4]triazolo[4,3-a]pyridine compounds of the present invention had a good inhibitory effect on c-MET tyrosine kinase at nanomolar concentration levels, and the results are shown in the following table.

Reference: Neru Munshi, Sébastien Jeay, Youzhi Li, et al. Molecular Cancer Therapeutics. Mol Cancer Ther 2010; 9:1544-1553.

Experimental Example 2

Experimental Purpose:

The purpose is to measure the growth inhibition effect of the compound on hepatocellular carcinoma cell lines HCCLM3, MHCC97-H, MHCC97-L, and stomach cancer cell lines SNU5, MKN-45.

Sample Storage and Preparation:

The positive control and the test compounds were firstly dissolved in 100% dimethyl sulfoxide to prepare a 20 mM stock solution, which was stored at −20° C. in a refrigerator. Before the experiment, the above stock solution was diluted with culture medium containing 0.6% dimethyl sulfoxide to prepare a 20× fold solution for each test concentration.

Experimental Procedure:

(1) To each well of 96-well plate was added 100 μl culture medium containing 2000 cells (HCCLM3/MHCC97-H/MHCC97-L was cultured in DMEM plus 10% FBS; SNU5 was cultured in IMDM plus 10% FBS; and MKN45 was cultured in RPMI1640 plus 10% GFBS). The plate was incubated in a 5% $CO_2$ incubator overnight.

(2) 20 μl diluted positive control or test compounds were added to each well, with two duplicate wells for each dilution. To the blank well and the control well were each added 20 μl culture medium containing 0.6% dimethyl sulfoxide. The final DMSO concentration was kept at 0.1%.

(3) After 72 hours, 60 μl CellTiter-Glo Reagent (Promega) were added each well, and mixed for 2 minutes on a shaker.

(4) The plate was incubated at room temperature for 45 minutes to stabilize the luminescence signal.

(5) BioTek microplate reader was used to measure the luminescence signal of each well.

(6) Using GraphPad software, a non-linear regression curve was generated based on the inhibition ratio as a function of the concentration of the compounds. The $IC_{50}$ was calculated using a S-shaped dose-effect curve fitting.

Reference: Neru Munshi, Sébastien Jeay, Youzhi Li, et al., ARQ 197, a Novel and Selective Inhibitor of the Human c-Met Receptor Tyrosine Kinase with Antitumor Activity. Mol Cancer Ther 2010; 9:1544-1553.

Results from Experimental Examples 1 & 2

| Half inhibitory concentration ($IC_{50}$) of exemplary compounds of the present invention on the receptor tyrosine kinase c-MET | | |
|---|---|---|
| Example No. | enzyme activity (nM) | cell activity (nM) |
| 2 | 4.9 | 1.4 |
| 3 | 3.9 | 4.3 |
| 4 | 11.3 | 123.8 |
| 5 | 3.1 | 11.8 |
| 6 | 3.3 | 598 |
| 7 | 122.7 | 327.1 |
| 8 | 37 | n/a |
| 9 | 17.8 | 14.1 |
| 10 | 8.6 | 1.6 |
| 11 | 308.7 | >1000 |
| 12 | 28.3 | 4.2 |
| 13 | >1000 | >1000 |
| 14 | 12.1 | 11.7 |
| 15 | 42.5 | 12.3 |
| 16 | 12 | 3 |
| 17 | 8.5 | 15.2 |
| 18 | 9.3 | 85.8 |
| 19 | 7.9 | 17.8 |
| 20 | 20.1 | 19.1 |
| 21 | 11.4 | 4.5 |
| 22 | 2.9 | 2 |
| 23 | 13.9 | 18.9 |
| 24 | 15.3 | 24.1 |
| 25 | 56.6 | 428.5 |
| 26 | 5.5 | 0.9 |
| 27 | 608.2 | >1000 |
| 28 | 3.6 | 2.1 |
| 29 | 7.1 | 6.2 |
| 30 | 122.3 | >10000 |
| 31 | 12.1 | 12.5 |
| 32 | 10 | 9.9 |
| 33 | 35.9 | 188.5 |
| 34 | 439.5 | 540.4 |
| 35 | 174.8 | 123.8 |
| 36 | 4.6 | 0.2 |
| 37 | 2.2 | 0.2 |
| 38 | 484.8 | >1000 |
| 39 | 5 | 0.4 |
| 40 | 2.5 | 0.5 |
| 41 | 3.2 | 2.8 |
| 42 | 10.7 | 0.7 |

Half inhibitory concentration (IC$_{50}$) of exemplary compounds of the present invention on the receptor tyrosine kinase c-MET

| Example No. | enzyme activity (nM) | cell activity (nM) |
|---|---|---|
| 43 | 461.7 | >1000 |
| 44 | 4.4 | 0.6 |
| 45 | 210.8 | 333.2 |
| 46 | 43 | 9.5 |
| 47 | 5.7 | 1.8 |
| 48 | 2.4 | 2.6 |

Experimental Example 3

Pharmacokinetic Evaluation

Pharmacokinetic test of the compounds of the invention
1. Abstract
Rats were used as test animals. A LC/MS/MS method was used to determine drug concentration in plasma at different time points after the rats were administered the compounds of Examples 3, 22 and 28 intragastrically. The pharmacokinetic behavior of the compounds of the present invention was studied and evaluated in rats.
2. Protocol
2.1 Test Drugs
Compounds of Example 3, Example 22 and Example 28
2.2 Test Animals
Eight healthy adult Sprague-Dawley (SD) rats, half male and half female, were divided into 2 groups with 4 rats in each group. The animals were purchased from SINO-BRITISH SIPPR/BK LAB. ANIMAL LTD., CO, Certificate No.: SCXK (Shanghai) 2008-0016.
2.3 Preparation of the Test Compounds
A certain amount of test compounds was weighed. 1.0 mL of dimethyl sulfoxide was added to dissolve the compounds. Normal saline was added to prepare a 1.0 mg/mL solution. The concentration of DMSO was kept at 5%.
2.4 Administration
After an overnight fast, the SD rats were administered the compounds intragastrically at a dose of 10.0 mg/kg and an administration volume of 10.0 mL/kg.
3. Procedure
Compounds of Example 3, 22 and 28 were administered intragastrically to rats. Blood samples (0.1 mL) were taken from the orbital sinus before the administration, and at 0.5, 1.0, 2.0, 3.0, 4.0, 6.0, 8.0, 12.0, 24.0, and 36.0 hours after administration. The blood sample was placed in a heparinized tube, and then centrifuged for 10 minutes at 4° C., at 10000 rpm to separate blood plasma. The plasma samples were stored at −20° C. The rats were fed 2 hours after compound administration.

Content determination of the test compounds in rat plasma after intragastrically administering at different concentrations: 50 μL of rat plasma taken at various time points after administration were mixed with 50 μL of internal standard solution and 100 μL of methanol, and mixed for 3 minutes by a vortexer. The mixture was centrifuged for 10 minutes at 13,500 rpm. 10 μL of the supernatant were taken from the plasma sample and analyzed by LC-MS/MS.

4. Results of Pharmacokinetic Parameters
Pharmacokinetic parameters of the compounds of the present invention are as follows:

| | Pharmacokinetic Assay (5 mg/kg) | | | | | |
|---|---|---|---|---|---|---|
| Example No. | Plasma Conc. Cmax (ng/mL) | Area Under Curve AUC (ng/mL*h) | Half life $t_{1/2}$ (h) | Mean Residence Time MRT (h) | Clearance CL/F (mL/min/kg) | Apparent Distribution Volume Vz/F (mL/kg) |
| 3 | 5000 ± 957 | 79255 ± 40707 | 7.54 ± 4.56 | 11.6 ± 5.8 | 1.33 ± 0.76 | 667 ± 87 |
| 22 | 8628 ± 592 | 122487 ± 13875 | 5.55 ± 0.78 | 9.10 ± 0.85 | 0.686 ± 0.071 | 327 ± 37 |
| 28 | 3603 ± 1817 | 30853 ± 25464 | 3.13 ± 0.54 | 5.17 ± 0.95 | 4.06 ± 2.4 | 1130 ± 790 |
| JNJ-38877605 | 2373 ± 1444 | 17325 ± 9505 | 2.97 ± 0.25 | 4.90 ± 0.62 | 5.81 ± 2.54 | 1480 ± 613 |

CONCLUSION

The compounds of the present invention had good pharmacokinetic absorption and significant pharmacokinetic advantages.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:
1. A compound of formula (V) or a pharmaceutically acceptable salt thereof:

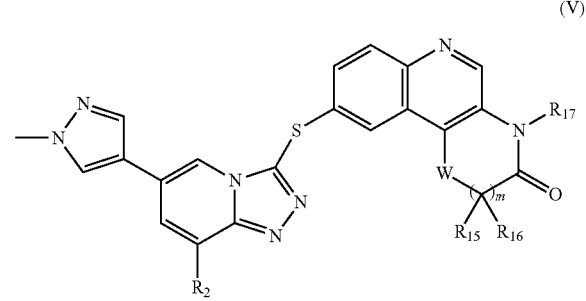

(V)

wherein:
R$_2$ is selected from the group consisting of hydrogen and fluorine;
W is selected from the group consisting of CH$_2$, O, N and S;
R$_{15}$ and R$_{16}$ are each independently selected from the group consisting of hydrogen, halogen, C$_1$-C$_6$ alkyl and alkoxyl;

$R_{17}$ is selected from the group consisting of hydrogen, $C_1$-$C_6$ alkyl, $C_1$-$C_6$ alkoxyl, $C_1$-$C_6$ alkoxylalkyl, —C(O)$R_5$, $C_3$-$C_{10}$ cycloalkyl and 3 to 8-membered heterocyclyl;

$R_5$ is selected from the group of hydrogen, $C_1$-$C_6$ alkyl, $C_3$-$C_{10}$ cycloalkyl, 3 to 8-membered heterocyclyl, $C_2$-$C_6$ alkenyl, $C_2$-$C_6$ alkynyl, aryl and heteroaryl, wherein the alkyl, cycloalkyl, heterocyclyl, aryl and heteroaryl are each optionally substituted by one or more groups independently selected from the group of alkyl, halogen, hydroxy, amino, alkoxyl, cycloalkyl, heterocyclyl, aryl, heteroaryl, —(CH$_2$)$_n$C(O)OR$_8$, —C(O)NR$_9$R$_{10}$, —NHC(O)R$_8$, —NR$_9$R$_{10}$, —NHC(O)NR$_9$R$_{10}$, —NHC(O)OR$_8$ and —NHS(O)$_m$R$_8$; and m=0 or 1.

2. A compound selected from the group consisting of:

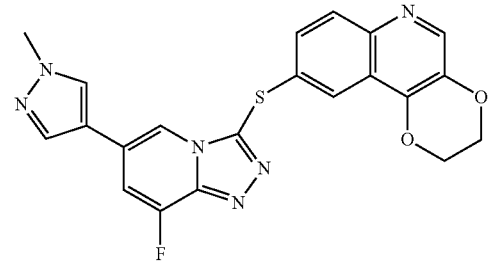

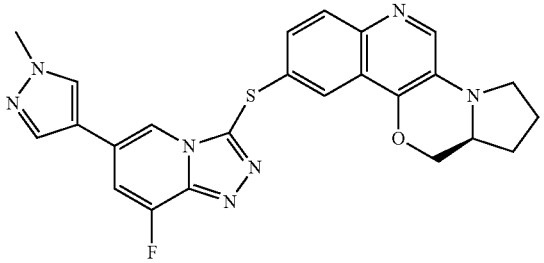

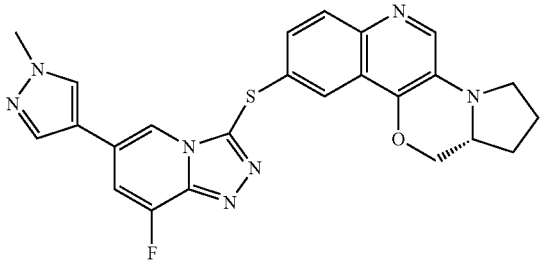

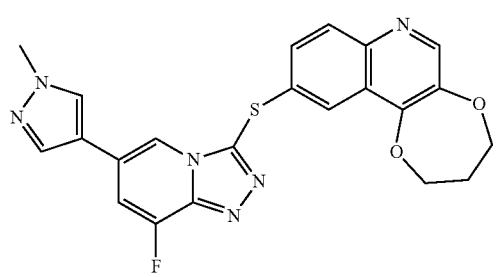

-continued

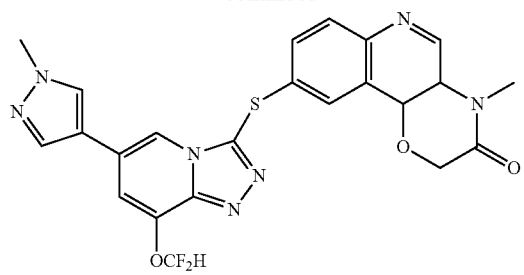

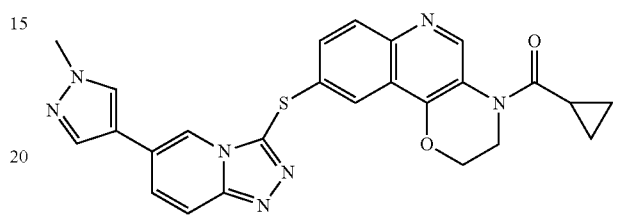

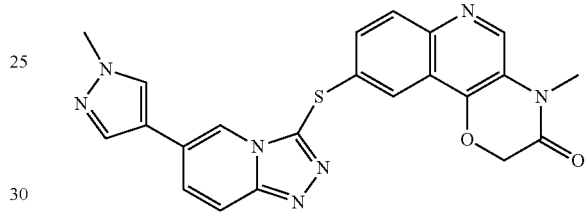

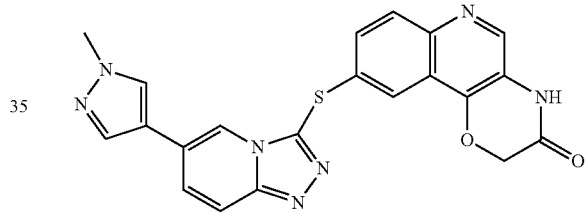

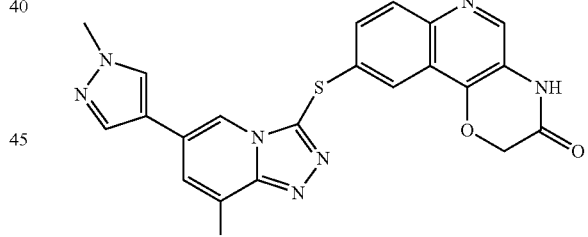

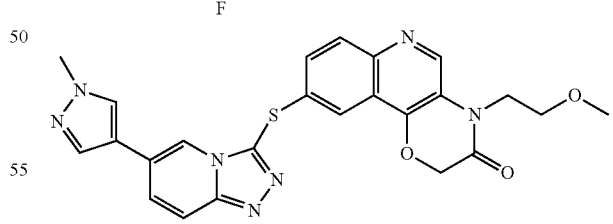

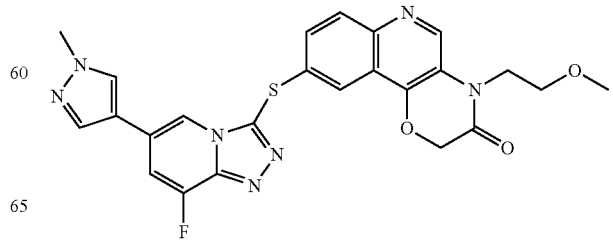

-continued

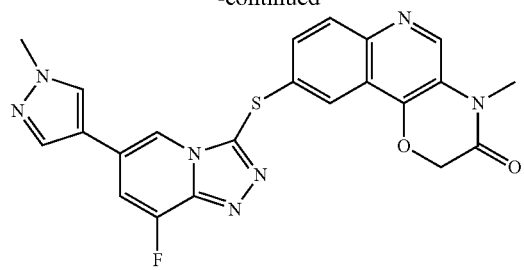

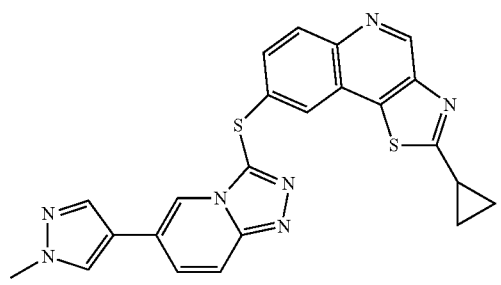

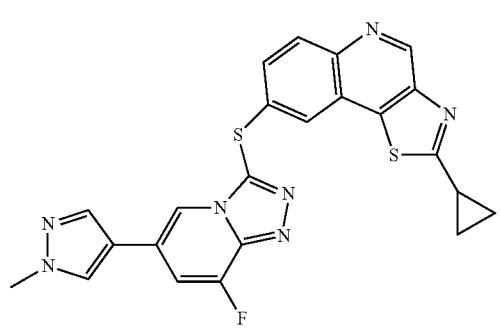

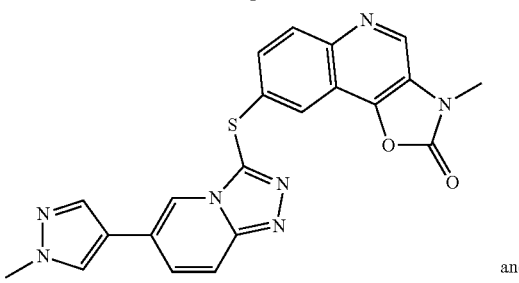

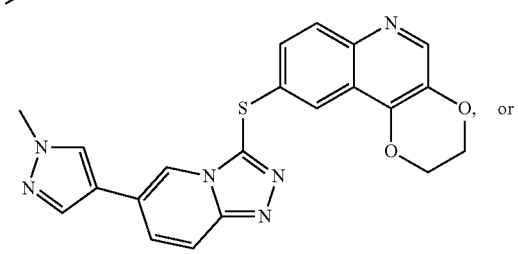 or a pharmaceutically acceptable salt thereof.

3. A process for preparing the compound of formula (I) or the pharmaceutically acceptable salt thereof, wherein the compound of formula (I) or the pharmaceutically acceptable salt thereof is a compound of formula (V) of a pharmaceutically acceptable salt thereof according to claim 1, the process comprising a step of:

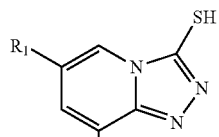 (IA)

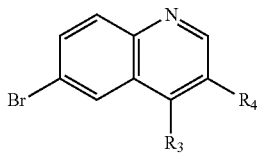 (IB)

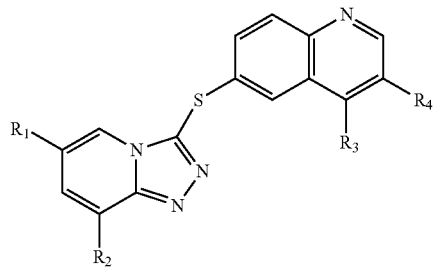 (I)

reacting a compound of formula (IA) with a compound of formula (TB) under an alkaline condition to give the compound of formula (I) or the pharmaceutically acceptable salt thereof, wherein $R_1$ is

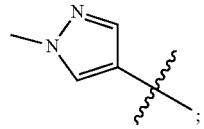 [SMILES: *c1cnn(C)c1];

$R_2$ is selected from group consisting of hydrogen and fluorine;

$R_3$ and $R_4$ are taken together with the attached carbon atoms to form the following structure:

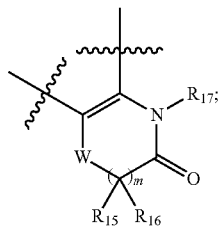

and m, W $R_{15}$, $R_{16}$, and $R_{17}$ are as defined in claim 1.

4. A pharmaceutical composition comprising a therapeutically effective amount of the compound of formula (V) or the pharmaceutically acceptable salt thereof according to claim 1, and a pharmaceutically acceptable carrier or excipient.

5. A method of modulating catalytic activity of a protein kinase, the method comprising a step of contacting the protein kinase with the compound of formula (V) or the pharmaceutically acceptable salt thereof according to claim 1, wherein the protein kinase is selected from the group consisting of c-Met tyrosine kinase.

6. The compound of formula (V) or the pharmaceutically acceptable salt thereof according to claim 1, wherein:
W is O;
$R_{15}$ and $R_{16}$ are each hydrogen;
$R_{17}$ is selected from the group consisting of hydrogen, $C_1$-$C_6$ alkyl, and $C_1$-$C_6$ alkoxylalkyl; and
m is 1.

7. The compound according to claim 2, wherein the compound is selected from the group consisting of:

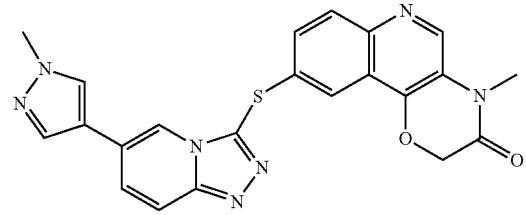

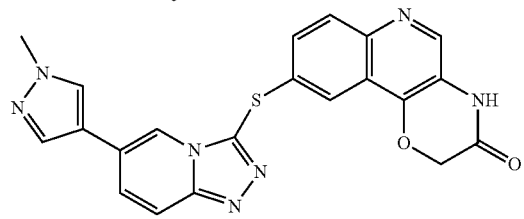

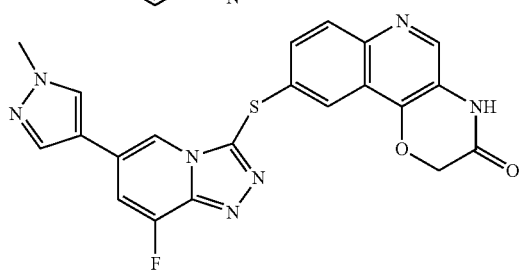

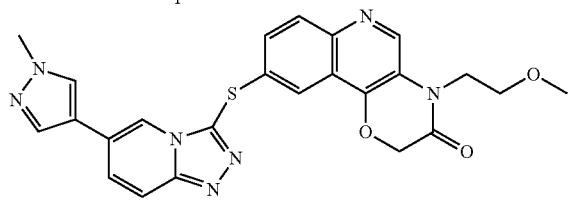

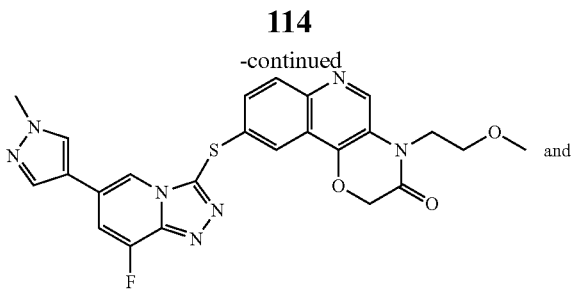
and

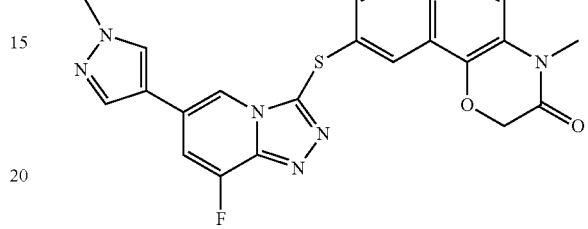

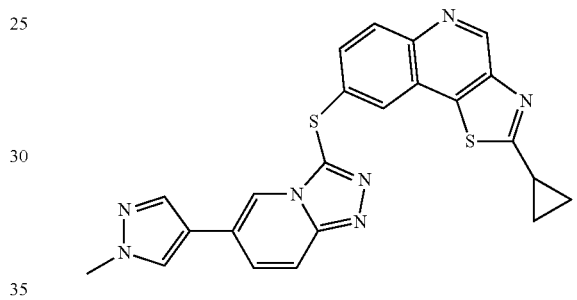

or a pharmaceutically acceptable salt thereof.

8. A pharmaceutical composition comprising a therapeutically effective amount of the compound or the pharmaceutically acceptable salt thereof according to claim 2, and a pharmaceutically acceptable carrier or excipient.

9. A method of modulating catalytic activity of a protein kinase, the method comprising a step of contacting the protein kinase with the compound or the pharmaceutically acceptable salt thereof according to claim 2, wherein the protein kinase is selected from the group consisting of c-Met tyrosine kinase.

* * * * *